United States Patent
Milstein et al.

(10) Patent No.: US 10,600,524 B2
(45) Date of Patent: Mar. 24, 2020

(54) RADIATION PROTECTION DEVICE AND METHODS THEREOF

(71) Applicant: STEMRAD LTD., Tel-Aviv (IL)

(72) Inventors: Oren Milstein, Tel Aviv (IL); Daniel Levitt, Los Altos, CA (US); Yoav Tikochinsky, Tel Aviv (IL); Eyal Zur, Tel Aviv (IL); Eran Zur, Tel Aviv (IL)

(73) Assignee: STEMRAD LTD., Tel Aviv (IL)

( * ) Notice: Subject to any disclaimer, the term of this patent is extended or adjusted under 35 U.S.C. 154(b) by 1195 days.

(21) Appl. No.: 13/676,995

(22) Filed: Nov. 14, 2012

(65) Prior Publication Data

US 2015/0004131 A1 Jan. 1, 2015
US 2018/0174696 A9 Jun. 21, 2018

Related U.S. Application Data

(63) Continuation-in-part of application No. PCT/US2012/037335, filed on May 10, 2012.

(60) Provisional application No. 61/484,916, filed on May 11, 2011.

(51) Int. Cl.
| | |
|---|---|
| *G21F 3/025* | (2006.01) |
| *G21F 3/02* | (2006.01) |
| *A61N 5/10* | (2006.01) |
| *A41F 9/00* | (2006.01) |
| *A62B 17/00* | (2006.01) |
| *G21F 1/02* | (2006.01) |

(52) U.S. Cl.
CPC .............. *G21F 3/025* (2013.01); *G21F 3/02* (2013.01); *A41D 2400/26* (2013.01); *A41D 2400/32* (2013.01); *A41F 9/002* (2013.01); *A61N 2005/1094* (2013.01); *A62B 17/006* (2013.01); *G21F 1/02* (2013.01)

(58) Field of Classification Search
None
See application file for complete search history.

(56) References Cited

U.S. PATENT DOCUMENTS

| | | | |
|---|---|---|---|
| 3,233,248 A | 2/1966 | Bushnell | |
| 3,310,053 A | 3/1967 | Greenwood | |
| 3,463,150 A | 8/1969 | Penfold | |
| 3,465,153 A | 9/1969 | Libby | |
| 3,996,620 A * | 12/1976 | Maine | A41D 13/04 2/455 |

(Continued)

FOREIGN PATENT DOCUMENTS

| | | | |
|---|---|---|---|
| CN | 2678066 Y | 2/2005 | |
| DE | 1918244 U * | 6/1965 | B41F 27/02 |

(Continued)

OTHER PUBLICATIONS

Search Report of Application No. PCT/US2012/037335 dated Nov. 28, 2012.

(Continued)

*Primary Examiner* — Andrew Smyth
(74) *Attorney, Agent, or Firm* — Troutman Sanders LLP

(57) ABSTRACT

A radiation protection device for providing protection of a body part that includes active bone marrow from ionizing radiation may include a radiation protection component configured to be placed adjacent to and externally cover the body part so as to reduce a radiation dose absorbed in that body part.

36 Claims, 13 Drawing Sheets

(56) References Cited

U.S. PATENT DOCUMENTS

| | | | |
|---|---|---|---|
| 4,196,355 A * | 4/1980 | Maine | A61B 6/107 250/516.1 |
| 4,386,277 A | 5/1983 | Forshee | |
| 5,028,796 A | 7/1991 | Swartz | |
| 5,103,504 A | 4/1992 | Dordevic | |
| 5,621,188 A | 4/1997 | Lee et al. | |
| 5,745,925 A * | 5/1998 | Ghilardi | G21F 3/02 2/338 |
| 6,101,711 A * | 8/2000 | Kobayashi | H05K 9/0018 29/825 |
| 6,531,086 B1 * | 3/2003 | Larsson | B29C 64/153 264/497 |
| 6,841,791 B2 * | 1/2005 | DeMeo | B32B 5/26 250/515.1 |
| 8,586,090 B2 * | 11/2013 | Dadachova | A61K 9/0019 424/195.15 |
| 2005/0211930 A1 * | 9/2005 | DeMeo | G01V 5/0008 250/516.1 |
| 2007/0237829 A1 * | 10/2007 | Dadachova | A61K 9/0019 424/489 |
| 2008/0272318 A1 * | 11/2008 | Cadwalader | G06Q 30/0215 250/516.1 |
| 2009/0000007 A1 * | 1/2009 | DeMeo | A41D 13/1209 2/83 |
| 2009/0156982 A1 * | 6/2009 | Petrie | A61K 9/0014 604/22 |
| 2013/0112924 A1 | 5/2013 | Eckhoff et al. | |
| 2013/0240763 A1 | 9/2013 | Khandkar et al. | |
| 2014/0021377 A1 | 1/2014 | Ashok et al. | |

FOREIGN PATENT DOCUMENTS

| | | | |
|---|---|---|---|
| DE | 1918244 U * | 6/1965 | B41F 27/02 |
| DE | 1918244 A1 * | 11/1970 | A62B 17/006 |
| DE | 1918244 A1 * | 11/1970 | A62B 17/009 |
| DE | 4132925 A1 * | 4/1993 | A61K 51/1279 |
| DE | 4132925 A1 * | 4/1993 | A61K 51/1279 |
| EA | 003918 | 10/2003 | |
| EP | 0173757 A1 | 3/1986 | |
| EP | 1052652 A2 | 11/2000 | |
| JP | 55-32463 | 3/1980 | |
| JP | 02-091599 | 3/1990 | |
| JP | H02-501769 | 6/1990 | |
| JP | H02-124600 | 10/1990 | |
| JP | 2001-242288 | 9/2001 | |
| JP | 2001242288 A * | 9/2001 | |
| JP | 2002131475 A * | 5/2002 | |
| JP | 2002131475 A * | 5/2002 | |
| JP | 2002-267793 | 9/2002 | |
| JP | 2005-538356 | 12/2005 | |
| JP | 2010-133772 | 6/2010 | |
| JP | 2010133772 A * | 6/2010 | |
| JP | 201376693 A | 4/2013 | |
| KR | 10-2001-0095618 | 11/2001 | |
| WO | 2012154962 A2 | 11/2012 | |
| WO | 2014163574 A1 | 10/2014 | |
| WO | 2016147193 A1 | 9/2016 | |

OTHER PUBLICATIONS

J. S. Senn et al. "Blood", Jan. 1, 1970, pp. 56-60 vol. 35, No. 1.
Written Opinion of the International Searching Authority for International App. No. PCT/US2012/037335 dated Nov. 21, 2013.
European Search Report for European Application No. EP 12782620, dated Sep. 12, 2014.
European Office Action of European Application No. 12 782 620.4, dated Nov. 17, 2015.
Japanese Office Action for JP Application No. 2014-510468 dated Mar. 22, 2016.
Office Action for EA Application No. 201391671 dated Nov. 2, 2016.
Japanese Office Action for JP application No. 2014-510468 dated Feb. 7, 2017.
European Communication (Extended European Search Report) for European Application No. EP 18187144.3, dated Dec. 20, 2018, 11 pages total.
Communication (Chinese First Office Action) issued by the State Intellectual Property Office of the People's Republic of China in Chinese Patent Application No. 201280034481.7, dated May 5, 2015, 16 pages total.
Communication (Chinese Second Office Action) issued by the State Intellectual Property Office of the People's Republic of China in Chinese Patent Application No. 201280034481.7, dated Mar. 11, 2016, 8 pages total.
Communication (Chinese Third Office Action) issued by the State Intellectual Property Office of the People's Republic of China in Chinese Patent Application No. 201280034481.7, dated Oct. 8, 2016, 8 pages total.
Communication (Chinese Fourth Office Action) issued by the State Intellectual Property Office of the People's Republic of China in Chinese Patent Application No. 201280034481.7, dated Apr. 6, 2017, 8 pages total.
Dillard, M.A., "Radiation Shielding Garment Technologies" (2015) accessed from: https://www.nasa.gov/sites/default/files/atoms/files/radiationshieldinggarmenttechnologies.docx, 2 pages total.
European Communication (Extended European Search Report) for European Application No. EP 16764351.9, dated Oct. 9, 2018, 10 pages total.
International Preliminary Report of Patentability of the International Searching Authority for International Application No. PCT/US2012/037335, dated Nov. 12, 2013, 7 pages total.
International Preliminary Report on Patentability for PCT Application No. PCT/IL2016/050298 dated Sep. 19, 2017, 9 pages total.
International Search Report for PCT Application No. PCT/IL2016/050298 dated Jul. 11, 2016, 5 pages total.
Ware, J. et al., "Design and Testing of Improved Spacesuit Shielding Components" Lawrence Berkeley National Laboratory (2002).
Wilson, J.W. et al., "Spacesuit Radiation Shield Design Methods" (1997) accessed from: https://ntrs.nasa.gov/archive/nasa/casi.ntrs.nasa.gov/20060046504.pdf, 16 pages total.
Written Opinion for PCT Application No. PCT/IL2016/050298 dated Jul. 11, 2016, 8 pages total.
Communication issued by Canada Patent Application by the Canadian Intellectual Property Office in Canadian Patent Application No. 2,825,601, dated May 14, 2018.

* cited by examiner

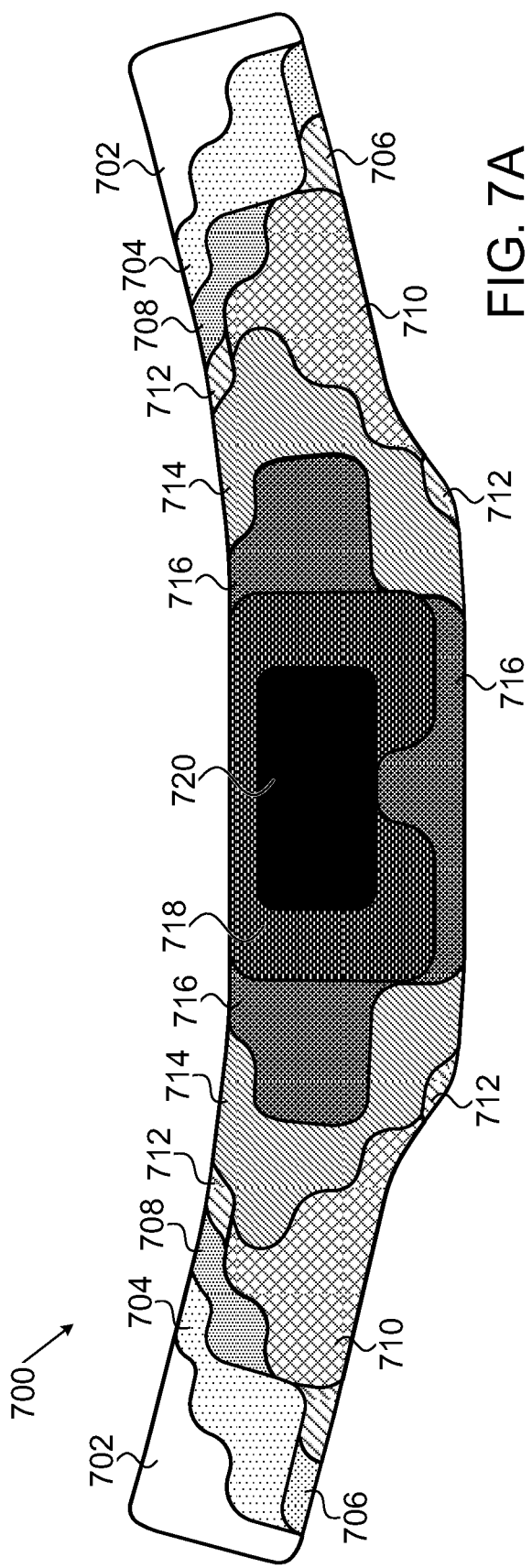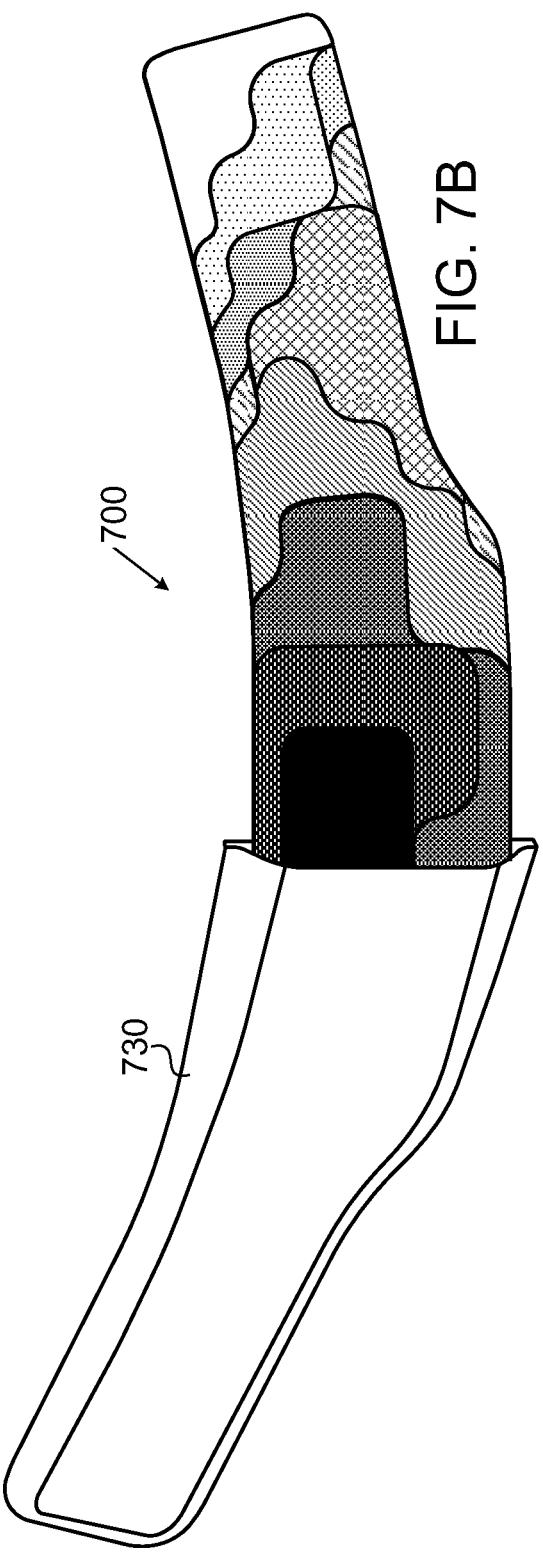
FIG. 7A
FIG. 7B

RADIATION PROTECTION DEVICE AND METHODS THEREOF

CROSS-REFERENCE TO RELATED APPLICATIONS

This patent application is a Continuation-In-Part application of International patent application PCT/US2012/037335 filed on May 10, 2012, which claimed the priority benefit of U.S. provisional patent application Ser. No. 61/484,916, filed on May 11, 2011, all incorporated herein in their entirety by reference.

FIELD OF THE INVENTION

The present invention relates to personal protection against ionizing radiation. More particularly it relates to a gamma radiation protection device and methods thereof.

BACKGROUND OF THE INVENTION

The use of radioactive material for both energy generation and military purposes has become internationally prevalent over the past few decades. While being inherently dangerous, the destructive potential of radioactive material only becomes apparent when it is taken out of a controlled environment, as a result of nuclear power plant malfunctions, acts of nature or when radioactive material falls into the hands of unauthorized parties. When any of the above occurs, scenarios of a nuclear reactor breach (i.e. Chernobyl and Fukushima), a radioactive 'dirty' bomb in the hands of terrorists or even a nuclear bomb attack, become disturbingly realistic (Department of Homeland Security, National Planning Scenarios, March 2006). These risks are further fueled by the increasing number of nuclear power plants that are being built by the newly developing economies of China and South Korea, and the ongoing race of unstable regimes to obtain nuclear arms. Thus, there is an ever-growing risk of nuclear catastrophe:

"Two decades after the end of the Cold War, we face a cruel irony of history. The risk of a nuclear confrontation between nations has gone down, but the risk of nuclear attack has gone up."—President Barack Obama Apr. 13, 2010

The fundamental danger of radioactive material is the ionizing radiation that it emits. Ionizing radiation damages living tissue by transferring energy to the atoms and molecules in the cellular structure, causing them to become ionized or excited. This which are responsible for vital cell processes.

Cells are able to repair damage in cases where low doses are received, such as from daily background radiation. At higher levels of radiation, cell death results. At exceedingly high doses, functional cells that are lost as part of normal tissue turnover are not replaced because of damage to the stem-cell compartment, leading to tissue failure. Radiation damage is most prominent in tissues with rapidly proliferating cells, as DNA damage from radiation commonly leads to the death of cells in the first cell division after irradiation, or within the first few divisions [.

Acute Radiation Syndrome (ARS), also known as Radiation Sickness, is a serious illness that manifests itself when the human body receives a high dose of ionizing radiation over a short period of time (usually several hours). Many survivors of the Hiroshima and Nagasaki atomic bomb detonations in 1945, and many of the firefighters who first responded to the Chernobyl nuclear power plant accident in 1986, became ill with ARS according to the Centers for Disease Control and Prevention (CDC).

The probability of survival of those inflicted with ARS decreases with escalating radiation dose. Most of the people who do not recover from ARS will die within a few weeks to a few months after exposure, with the primary cause of death being the destruction of the person's bone marrow.

Bone marrow is comprised of hematopoietic stem cells (HSCs) which are ultimately responsible for the constant renewal of blood, giving rise to billions of new blood cells each day. Due to their high rate of proliferation, HSCs are especially vulnerable to ionizing radiation]. Owing to their central role in blood production, lethal irradiation of HSCs may lead to death from severe anemia, infection and internal bleeding. This cause and effect relationship between high doses of radiation and HSC apoptosis, has led to the use of HSC transplantation (i.e. bone marrow transplantation) as a life-saving intervention in cases of exposure to high doses of radiation.

People inflicted with ARS can benefit from bone marrow transplantation post-exposure in an effort to restore their body's cell production, however, this is a challenging procedure. There are two methods of HSC transplantation. In the first, bone marrow is harvested from the individual prior to irradiation, stored and later transplanted. This form of transplantation does not require tissue matching and is thus coined autologous transplantation. However, very few individuals have preemptively stored their bone marrow, making this method common only in myeloablative cancer therapy. The second method is allogeneic bone marrow transplantation, wherein the source of bone marrow is from a donor. Allogeneic transplantation requires that the donor and recipient be of matched tissue types (i.e. human leukocyte antigen types). If mismatched bone marrow transplantation is attempted, graft rejection is likely to ensue. There is also a high likelihood of Graft vs. Host Disease (GVHD), an often fatal condition resulting from an assault of the donor immune cells embedded in the graft on the recipient's bodily tissues. Unfortunately, matched donors are a scarcity due to the tremendous polymorphism in the human leukocyte antigen locus. Moreover, transplantation must take place in the immediate days following exposure to radiation, further increasing the challenge in locating a matched donor. In the event of a catastrophe with a large number of victims, the time-frame imposed is not likely to enable isolation of matched donors.

Based on previous nuclear disasters, such as the atomic bombings of Japan and the Chernobyl meltdown, the median lethal dose (LD50) of radiation in the human population has been established to be around 400 rad (4 Gray or Gy). For those few individuals who are able to obtain matched or otherwise engraftable bone marrow transplants, the LD50 (dose at which 50% of the population perishes) increases to at least 1,000 rad, a fact that is readily demonstrable in medical practice, where thousands of individuals to date have undergone supra-lethal Total Body Irradiation (TBI) for purposes of cancer therapy, and were subsequently rescued by bone marrow transplantation. Thus, life-threatening damage may be reversed by bone marrow transplantation in individuals receiving radiation doses as high as 1,000 rad. Indeed, according to the CDC, at doses between 200 and 1,000 rad, the only significant life-endangering threat is bone marrow damage. At doses in excess of 1,000 rad, damage to gastrointestinal (GI) tissue may become a limiting factor in survival.

According to official estimates of the US Department of Homeland Security (DHS), the majority of deaths resulting from a possible nuclear detonation in an urban area would be from exposure to high doses of external radiation. According to these estimates, most of these deaths would result from doses inside the 200-1,000 rad range, the range in which bone marrow is the only body tissue likely to sustain irreversible damage (see Appendix)

In the Chernobyl disaster, the vast majority of firefighters who were first on the scene, received radiation doses that ranged between 80 and 1,000 rad, according to the United Nations Scientific Committee on the Effects of Atomic Radiation (UNSCEAR) final report on the disaster. Thus, in marked resemblance to the DHS estimates of exposure in a detonation, most exposures in Chernobyl were within a dose range whereby bone marrow was the only seriously damaged tissue. Indeed, UNSCEAR reports have repeatedly concluded that the underlying cause of death among the 28 firefighters who succumbed to ARS in Chernobyl was bone marrow failure [21, 22].

First-responders (firefighters, medics, technicians, etc.) are relied on to perform their life-saving duties, and to stem the exacerbation of the already dire circumstances. The extremely volatile nature of nuclear reactor incidents, such as Chernobyl or Fukushima, requires that first-responders have at their disposal the optimal protection from radiation, so that an already catastrophic scenario does not escalate further.

Ionizing radiation can be classified into two categories: photons (gamma radiation and x-rays) and particles (alpha and beta particles). Shielding the human body from gamma rays requires large amounts of high-mass material, in stark contrast to alpha particles that can be blocked by paper or skin, and beta particles that can be blocked by foil. Gamma rays are best blocked using materials possessing high atomic numbers and high density. For this reason, a lead shield is significantly better (by 20-30%) as a gamma ray blocker, when compared to an equal mass of an alternative shielding material such as aluminum, steel, concrete, water or soil. The higher the energy of the gamma rays, the thicker the shielding that is required.

In nuclear disasters, radioactive materials are commonly presented in the form of nuclear fallout. Fallout consists of radiation-emitting particles ranging in sizes, together creating a cloud of radioactive dust. The closer to ground an atomic bomb is detonated, the more dust and debris is thrown into the air, resulting in greater amounts of nuclear fallout. Whenever individuals remain in an area contaminated with fallout, such contamination leads to immediate external radiation exposure as well as possible later internal hazard from inhalation and ingestion of radiocontaminants. The radioactive dust emanating from nuclear accidents or from radiological bomb (dirty bomb) detonations poses dangers similar to that of fallout.

Protective clothing can protect from the alpha and beta radiation emitted from fallout, but offers no protection from gamma radiation. Facemasks, eye-goggles and respirators can protect from inhalation and ingestion of fallout particles, but again provide no protection from gamma radiation. Gamma radiation attenuating devices and garments have been described in the past, but most were developed to offer either whole-body protection, or to cover as much of the body as possible. Moreover, due to the significant weight of radiation-attenuating materials, existing shielding solutions are made using only a thin layer of radiation-attenuating material, so as to remain bearable by their wearers. These thin layers attenuate radiation transmission in a manner that may be beneficial for reducing the incidence of long-term health effects from low-energy radiation, but are insufficient for preventing the acute health effects that result from exposure to high doses of radiation (i.e. Acute Radiation Syndrome). The resultant loss of active bone marrow in individuals with ARS has dire health consequences. Thus, there is an urgent need for measures that may be taken to protect bone marrow from gamma radiation.

BRIEF DESCRIPTION OF THE INVENTION

There is thus provided, in accordance with some embodiments of the present invention, a radiation protection device comprising a radiation attenuation component that may be configured to provide varying radiation attenuation levels across the radiation attenuating component and to be placed adjacent to and externally cover a body part that includes active bone marrow so as to reduce a radiation dose absorbed by the bone marrow in that body part.

Furthermore, in accordance with some embodiments, the body part that includes active bone marrow may include a bone selected from the group of bones consisting of: lumbar vertebrae, sacrum, pelvis, ilium, pubis and femur.

Furthermore, in accordance with some embodiments, the varying radiation attenuation levels across the radiation attenuating component may be substantially inversely related to radiation attenuation levels of tissue present between a given point of the radiation attenuating component and the active bone marrow.

Furthermore, in accordance with some embodiments, the varying radiation attenuation levels may be determined by the formula $$A_R(x, y, z) = \frac{A_D}{A_T},$$

where $A_R$ is a required radiation attenuation at point x,y,z on the radiation attenuating component, $A_D$ is a radiation attenuation level needed to reduce the radiation dose absorbed in the active bone marrow contained within the body part to a desired level, and $A_T$ is the tissue radiation attenuation level between the point x,y,z and the active bone marrow contained within the body part.

Furthermore, in accordance with some embodiments, the radiation attenuating component may comprise radiation attenuating material of varying thickness or varying radiodensity.

Furthermore, in accordance with some embodiments, the radiation attenuating component may comprise layers of radiation attenuating material.

Furthermore, in accordance with some embodiments, friction minimizing material may be provided between the layers of radiation attenuating material.

Furthermore, in accordance with some embodiments, the friction minimizing material provided between the layers of radiation attenuating material may be selected from the group of materials consisting of Polytetrafluoroethylene (PTFE, Teflon), polyamide-imide (PAI), Nylon 6-6, Nylon 4-6, graphite, graphite powder, acetal homopolymer or carbon fiber, and a lubricant.

Furthermore, in accordance with some embodiments, the layers of radiation attenuating material when compiled may define a topography related to tissue radiation attenuation levels between points on the radiation attenuating component and the active bone marrow contained within the body part.

Furthermore, in accordance with some embodiments, the layers of radiation attenuating material may be interconnected so as to allow relative movement between the layers when subjected to bending Furthermore, in accordance with some embodiments, the radiation attenuating component of the radiation protection device may be supported by a support structure.

Furthermore, in accordance with some embodiments, the support structure supporting the radiation attenuating component may be resilient.

Furthermore, in accordance with some embodiments, the support structure supporting the radiation attenuating component may be configured to prevent buckling of the radiation attenuation component when the radiation attenuation component is subjected to bending.

Furthermore, in accordance with some embodiments, the radiation attenuating component may comprise one or more materials selected from the group of materials consisting of barium compounds, barium sulfate, barium chloride, tungsten compounds, tungsten carbide, tungsten oxide, tungsten, bismuth compounds, bismuth, lead, tantalum compounds, titanium, titanium compounds, diatrizoate meglumine, acetrizoate sodium, boron, boric acid, boron oxide, boron salts, other boron compounds, beryllium, beryllium compounds, bunamiodyl sodium, diatrizoate sodium, ethiodized oil, gold, lobenzamic acid, locarmic acid, locetamic acid, Iodipamide, Iodixanol, Iodized oil, Iodoalphionic acid, o-Iodohippurate sodium, Iodophthalein sodium, Iodopyracet, loglycamic acid, Iohexol, lomeglamic acid, Iopamidol, lopanoic acid, Iopentol, Iophendylate, lophenoxic acid, water, Iopromide, lopronic acid, lopydol, lopydone, lothalamic acid, Iotrolan, Ioversol, loxaglic acid, Ioxilan, Ipodate, meglumine acetrizoate, meglumine ditrizoate methiodal sodium, metrizamide, metrizoic acid, phenobutiodil, phentetiothalein sodium, propryliodone, silver, sodium Iodomethamate, sozoiodolic acid, thorium oxide, trypanoate sodium, uranium and depleted uranium.

Furthermore, in accordance with some embodiments, the radiation attenuating component may be incorporated in a wearable item selected from the groups of items consisting of a helmet, a bifurcated garment and a belt.

Furthermore, in accordance with some embodiments, the radiation protection device may further comprise a sealable opening for intraosseous injection of a substance into an underlying bone within the body part containing active bone marrow.

Furthermore, in accordance with some embodiments, there is provided a method for protecting bone marrow of a subject from ionizing radiation, the method comprising: placing a radiation protection device that includes a radiation attenuation component configured to provide varying radiation attenuation levels across the radiation attenuating component, adjacent to and externally covering a body part that includes active bone marrow so as to reduce a radiation dose absorbed by the bone marrow in that body part.

Furthermore, in accordance with some embodiments, the method may further includes designing the varying attenuation levels of the radiation attenuation component to be inversely related to radiation attenuation levels of tissue present between a given point of the radiation attenuating component and the active bone marrow.

Furthermore, in accordance with some embodiments, the varying radiation attenuation levels may be determined by the formula $$A_R(x, y, z) = \frac{A_D}{A_T},$$

where $A_R$ is a required radiation attenuation at point x,y,z on the radiation attenuating component, $A_D$ is a radiation attenuation level needed to reduce the radiation dose absorbed in the active bone marrow contained within the body part to a desired level, and $A_T$ is the tissue radiation attenuation level between the point x,y,z and the active bone marrow contained within the body part.

Furthermore, in accordance with some embodiments, the radiation attenuating component may be comprised of layers of radiation attenuating material.

Furthermore, in accordance with some embodiments, the method may further include administering a substance to the subject for enhancing hematopoietic reconstitution or inducing proliferation of hematopoietic stem cells or progenitors.

Furthermore, in accordance with some embodiments, the substance may be selected from the group of substances consisting of G-CSF, PEGylated G-CSF, GM-CSF, M-CSF (CSF-1), AMD3100, Filgrastim (Neupogen), Pegfilgrastim, Stem cell factor (c-kit ligand or Steel Factor), Interleukin 11, Interleukin 3, Interleukin 7, Interleukin 6, Interleukin 12, Interleukin 1, Interleukin 2, Interleukin 4, Interleukin 8, Interleukin 9 Interleukin 15, Erythropoietin (EPO), Epoetin alfa (Epogen), Darbepoetin alfa (Aranesp), Omontys (peginesatide), SDF-1, friend of GATA-1 (FOG-1), PTH and active PTH fragments or PTH/PTHrP receptor agonists, leukemia inhibitory factor (LIF), Platelet-derived growth factor (PDGF), Angiotensin-(1-7), Leridistimor, Flt3-ligand, thrombopoietin, Keratinocyte growth factor (KGF), TGFβ, MPL receptor agonists, Promegapoietin-1α (PMP-1α), hyaluronic acid and K-7/D-6.

Furthermore, in accordance with some embodiments, the method may further include administering a substance to the subject for inhibiting apoptosis of hematopoietic stem cells or progenitors.

Furthermore, in accordance with some embodiments, the substance may be selected from the group of substances consisting of G-CSF, PEGylated G-CSF, GM-CSF, M-CSF (CSF-1), AMD3100, Filgrastim (Neupogen), Pegfilgrastim, Stem cell factor (c-kit ligand or Steel Factor), Interleukin 11, Interleukin 3, Interleukin 7, Interleukin 6, Interleukin 12, Interleukin 1, Interleukin 2, Interleukin 4, Interleukin 8, Interleukin 9 Interleukin 15, Erythropoietin (EPO), Epoetin alfa (Epogen), Darbepoetin alfa (Aranesp), Omontys (peginesatide), SDF-1, friend of GATA-1 (FOG-1), PTH and active PTH fragments or PTH/PTHrP receptor agonists, leukemia inhibitory factor (LIF), Platelet-derived growth factor (PDGF), Angiotensin-(1-7), Leridistimor, Flt3-ligand, thrombopoietin, Keratinocyte growth factor (KGF), TGFβ, MPL receptor agonists, Promegapoietin-1α (PMP-1α), hyaluronic acid and K-7/D-6, δ-Tocotrienol (DT3), Angiotensin-(1-7), Inducers of nuclear factor-Kappa B, Flagellin, vitamin C, WR-2721 and WR-1065, CBLB502.

Furthermore, in accordance with some embodiments, the method may further includes administering a substance to the subject to prevent hematopoietic stem cells or progenitors within the active bone marrow from leaving the protected active bone marrow and circulating.

Furthermore, in accordance with some embodiments, the substance may be selected from the group of substances consisting of SDF-1 (CXCL12) or an analog, fusion protein, variant, functional derivative or fragment thereof having the activity of SDF-1 and/or an agent capable of inducing expression of said chemokine SDF-1, PDGF, Somatostatin, c-kit, Hepatocyte growth factor (HGF), anti MMP-9 (anti matrix metalloproteinase-9) antibody, neutrophil elastase (NE) inhibitor, Migrastatin or its analogues including but not limited to core macroketone and core macrolactam, TGF-β, IL-8 inhibitors, anti Groβγ antibody, anti Gr1 antibody, anti LFA-1 antibody, anti Mac-1 (CD11b) antibody, cathapsin G inhibitors, anti SDF-1 blocking antibody, soluble CXCR4, soluble CCR2, MCP-1 (CCL2) and MCP-3 (CCL7) inhibitors, G-CSF inhibitors, GM-CSF inhibitors, soluble VLA-4, anti MMP-2 antibody CB2 agonists including but not limited to AM1241.

Furthermore, in accordance with some embodiments, the method may further include administering a substance to the subject to attract hematopoietic stem cells or progenitors into the protected active bone marrow.

Furthermore, in accordance with some embodiments, the substance may be selected from the group of substances consisting of SDF-1 (CXCL12) or an analog, fusion protein, variant, functional derivative or fragment thereof having the activity of SDF-1 and/or an agent capable of inducing expression of said chemokine SDF-1. agonists or partial agonists of CXCR4 and/or CXCR7, CCR2 ligands including but not limited to MCP-1 (CCL2) and MCP-3 (CCL7), CB2 agonists including but not limited to AM1241, PDGF, Somatostatin, c-kit, Hepatocyte growth factor (HGF).

Furthermore, in accordance with some embodiments, the method may further include administering a substance to the subject before, during or after the exposure to ionizing radiation

BRIEF DESCRIPTION OF THE DRAWINGS

Examples are described in the following detailed description and illustrated in the accompanying drawings in which:

FIG. 7A illustrates the layer assembly of a radiation attenuating component for a radiation protection device in accordance with embodiments of the present invention;

FIG. 7B illustrates the layer assembly of the radiation attenuating component shown in FIG. 7A with a protective sheath, according to embodiments of the present invention;

DETAILED DESCRIPTION OF THE INVENTION

Figure 1:
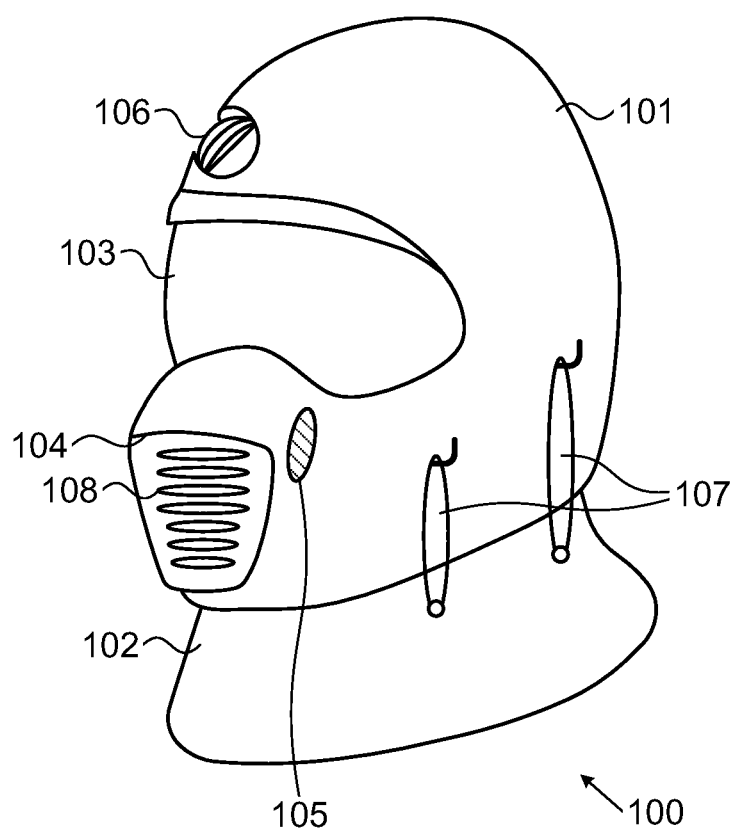
FIG. 1 illustrates a perspective view of a radiation protection device embodied as a helmet in accordance with an embodiment of the present invention.

Although examples are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method examples described herein are not constrained to a particular order or sequence. Additionally, some of the described method examples or elements thereof can occur or be performed at the same point in time.

According to embodiments of the present invention, a radiation protection device may be designed to protect the wellbeing or the viability of a living subject by providing radiation protection to one or a plurality of portions of said subject's body. The radiation protection device may typically include a radiation protection component. The radiation protection component may be comprised of a radiation attenuating component that includes radiation attenuating material. The radiation protection component may be comprised of a blower that blows away radioactive particles.

"Attenuation", in the context of the present invention, is meant to refer to reducing radiation passing through and also to fully blocking radiation from passing through.

"Blowing away", in the context of the present invention, is meant to refer to the act of distancing radioactive particles from the protected subject so as to reduce the dose received from those particles.

"Radiation" in the context of the present invention may include ionizing radiation.

"Radiation" in the context of the present invention may include alpha radiation, beta radiation, gamma radiation, neutron radiation, x-ray radiation or a combination thereof.

"Radiation", in the context of the present invention is meant to refer to radiation that is external radiation that has the potential to induce Acute Radiation Syndrome (ARS).

External radiation that has the potential to induce ARS is any radiation that is of an energy sufficient to penetrate the outer layer of a living body.

Upon exposure to radiation levels of up to 1,000 rad (10 Gy), most of the bodily damage sustained is to the bone marrow tissue. The radiation exposure levels in a nuclear catastrophe such as in an atomic bomb detonation or following a nuclear reactor meltdown are largely within this range. Thus, we conclude that a great number of the casualties resulting from exposure to radiation in a nuclear event may be avoided by shielding bone marrow from radiation. Thus, in accordance with embodiments of the current invention, rather than resorting to the nearly impossible task of bone marrow transplantation following a catastrophic event to rescue lethally-exposed individuals, in-situ radiation protection of bone marrow is provided.

Radiation attenuating materials are typically of high densities and therefore potentially impose heavy weight on their bearer. It is impractical to provide whole body protection from high energy gamma radiation (e.g. greater than 100 KEV) while affording mobility. The tissue that is first to sustain irreversible damage upon exposure to radiation is the bone marrow tissue. The capacity of bone marrow tissue to produce blood components is dictated by the number of viable hematopoietic stem cells (HSCs) embedded within it. In humans, HSCs are marked by the CD34 glycoprotein and denoted CD34+. In accordance with embodiments of the current invention selective radiation protection to strategic concentrations of HSCs is provided.

Bone marrow tissue has dramatic regenerative potential. Thirty bone marrow-derived HSCs are sufficient to save 50 percent of lethally irradiated mice, and to reconstitute all blood cell types in the survivors. In the common procedure of bone marrow transplantation, the quantity of hematopoietic stem cells extracted from a single active marrow site is sufficient to support the complete reconstitution of the hematopoietic stem cell compartment in a lethally irradiated human recipient. In contrast to mature blood cells, which are dispersed throughout the body, hematopoietic stem cells are confined to the bones. Thus, in accordance with embodiments of the current invention a radiation protection device which is capable of preserving the viability of a number of HSCs sufficient to spare hematopoietic functions and allow for the survival of a subject receiving otherwise full-body irradiation is provided.

A radiation protection device, which is intended to specifically protect bone marrow concentrations rather than the entire body or large portions of the body, allows using thick layers of radiation-attenuating materials that offer substantial radiation shielding for body parts in which bone marrow is concentrated, while leaving other body parts generally unshielded or lightly shielded. Thus in accordance with embodiments of the current invention, the radiation protection device as described herein is able to substantially attenuate gamma radiation penetration into a protected marrow while allowing mobility to the wearer.

HSC concentrations are present in several bone marrow locations in the human body, the foremost of which are the hip, sternum, ribs, vertebrae and skull. The iliac bones of the hip have high active bone marrow content, serve as the source for bone marrow in bone marrow transplantation and they lie in the pelvic girdle, the human body's center of gravity. Thus in some embodiments of the current invention the iliac bones of the hip may be an attractive target for protection in adults.

In some embodiments of the current invention, in children up to the age of ten the bone marrow residing in the skull may serve as the target for protection, being the foremost concentration of active bone marrow in early life.

In some embodiments of the current invention, the type, thickness and the distribution of the radiation attenuating materials used in the manufacture of the radiation protection device as described herein may be selected so as to protect a critical volume of active bone marrow to allow for recovery post-irradiation.

In some embodiments of the current invention, the type, thickness and the distribution of the radiation attenuating materials used in the manufacture of the radiation protection device as described herein may be selected so that HSCs having their viability secured by the radiation protection device as described herein are at least as effective as transplanted HSCs in reconstituting the hematopoietic system of an irradiated subject.

In some embodiments of the current invention, the type, thickness and the distribution of the radiation attenuating materials used in the manufacture of the radiation protection device as described herein may be selected so as that HSCs having their viability secured by the radiation protection device as described herein are more effective than transplanted HSCs in reconstituting the hematopoietic system of an irradiated subject.

In some embodiments of the current invention, the type, thickness and the distribution of the radiation attenuating materials used in the manufacture of the radiation protection device as described herein may be selected so as that HSCs having their viability secured by the radiation protection device as described herein are not as effective as transplanted HSCs in reconstituting the hematopoietic system of an irradiated subject.

In some embodiments of the current invention, the type, thickness and the distribution of the radiation attenuating materials used in the manufacture of the radiation protection device as described herein may be selected so as that the quantity of bone marrow the radiation protection device described herein protects from the effects of gamma radiation in a subject is at least equivalent to 25% of the bone marrow quantity used in the current practice of transplantation of irradiated human recipients. In some embodiments of the current invention, the type, thickness and the distribution of the radiation attenuating materials used in the manufacture of the radiation protection device as described herein may be selected so as that the quantity of bone marrow the radiation protection device described herein protects from the effects of gamma radiation in a subject is at least equivalent to 50% of the bone marrow quantity used in the current practice of transplantation of irradiated human recipients. In some embodiments of the current invention, the type, thickness and the distribution of the radiation attenuating materials used in the manufacture of the radiation protection device as described herein may be selected so as that the quantity of bone marrow the radiation protection device described herein protects from the effects of gamma radiation in a subject is at least equivalent to 75% of the bone marrow quantity used in the current practice of transplantation of irradiated human recipients. In some embodiments of the current invention, the type, thickness and the distribution of the radiation attenuating materials used in the manufacture of the radiation protection device as described herein may be selected so as that the quantity of bone marrow the radiation protection device described herein protects from the effects of gamma radiation in a subject is at least equivalent to 100% of the bone marrow quantity used in the current practice of transplantation of irradiated human recipients.

In some embodiments of the current invention, the type, thickness and the distribution of the radiation attenuating materials used in the manufacture of the radiation protection device as described herein may be selected so as that the number of viable HSCs the radiation protection device described herein protects from death due to gamma radiation is at least equivalent to 25% of the number of HSCs used in the current practice of transplantation of irradiated human recipients. In some embodiments of the current invention, the type, thickness and the distribution of the radiation attenuating materials used in the manufacture of the radiation protection device as described herein may be selected so as that the number of viable HSCs the radiation protection device described herein protects from death due to gamma radiation is at least equivalent to 50% of the number of HSCs used in the current practice of transplantation of irradiated human recipients. In some embodiments of the current invention, the type, thickness and the distribution of the radiation attenuating materials used in the manufacture of the radiation protection device as described herein may be selected so as that the number of viable HSCs the radiation protection device described herein protects from death due to gamma radiation is at least equivalent to 75% of the number of HSCs used in the current practice of transplantation of irradiated human recipients. In some embodiments of the current invention, the type, thickness and the distribution of the radiation attenuating materials used in the manufacture of the radiation protection device as described herein may be selected so as that the number of viable HSCs the radiation protection device described herein protects from death due to gamma radiation is at least equivalent to 100% of the number of HSCs used in the current practice of transplantation of irradiated human recipients.

In some embodiments of the current invention, the type, thickness and the distribution of the radiation attenuating materials used in the manufacture of the radiation protection device as described herein may be selected so that the number of HSCs the radiation protection device described herein protects from death due to gamma radiation is dependent on the weight of the protected subject.

In some embodiments of the current invention, the type, thickness and the distribution of the radiation attenuating materials used in the manufacture of the radiation protection device as described herein may be selected so that the number of HSCs the radiation protection device described herein protects from death due to gamma radiation is at least $0.25 \times 10^6$/kg. In some embodiments of the current invention the type, thickness and the distribution of the radiation attenuating materials used in the manufacture of the radiation protection device as described herein may be selected so that the number of HSCs the radiation protection device described herein protects from death due to gamma radiation is at least $0.5 \times 10^6$/kg. In some embodiments of the current invention, the type, thickness and the distribution of the radiation attenuating materials used in the manufacture of the radiation protection device as described herein may be selected so that the number of HSCs the radiation protection device described herein protects from death due to gamma radiation is at least $0.75 \times 10^6$/kg. In some embodiments of the current invention the type, thickness and the distribution of the radiation attenuating materials used in the manufacture of the radiation protection device as described herein may be selected so that the number of HSCs the radiation protection device described herein protects from death due to gamma radiation is at least $1 \times 10^6$/kg. In some embodiments of the current invention, the type, thickness and the distribution of the radiation attenuating materials used in the manufacture of the radiation protection device as described herein may be selected so that the number of HSCs the radiation protection device described herein protects from death due to gamma radiation is at least $1.5 \times 10^6$/kg. In some embodiments of the current invention, the type, thickness and the distribution of the radiation attenuating materials used in the manufacture of the radiation protection device as described herein may be selected so that the number of HSCs the radiation protection device described herein protects from death due to gamma radiation is at least $2 \times 10^6$/kg. In some embodiments of the current invention the type, thickness and the distribution of the radiation attenuating materials used in the manufacture of the radiation protection device as described herein may be selected so that the number of HSCs the radiation protection device described herein protects from death due to gamma radiation is at least $3 \times 10^6$/kg. In some embodiments of the current invention, the type, thickness and the distribution of the radiation attenuating materials used in the manufacture of the radiation protection device as described herein may be selected so that the number of HSCs the radiation protection device described herein protects from death due to gamma radiation is at least $4 \times 10^6$/kg. In some embodiments of the current invention, the type, thickness and the distribution of the radiation attenuating materials used in the manufacture of the radiation protection device as described herein may be selected so that the number of HSCs the radiation protection device described herein protects from death due to gamma radiation is at least $5 \times 10^6$/kg.

In some embodiments of the current invention, the type, thickness and the distribution of the radiation attenuating materials used in the manufacture of the radiation protection device as described herein may be selected so that the quantity of red marrow the radiation protection device described herein protects from death due to gamma radiation is dependent on the weight of the protected subject.

In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 500 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 400 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 300 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 250 grams.

In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 200 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 150 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 100 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 80 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 60 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 50 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 40 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 30 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 25 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 20 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 15 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 5 and 10 grams.

In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 10 and 500 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 15 and 300 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 20 and 200 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 22 and 150 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 23 and 100 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 24 and 80 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 25 and 70 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 26 and 60 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 27 and 50 grams. In some embodiments of the current invention, the type, thickness and the distribution of the radiation attenuating materials used in the manufacture of the radiation protection device as described herein may be selected so that the quantity of net active marrow the radiation protection device described herein protects from death due to gamma radiation is between 28 and 40 grams.

In some embodiments of the current invention, the radiation protection device is configured to protect a bone or bones that have a high content of active bone marrow. In another embodiment of the current invention, the bone or bones selected for protection by the radiation protection device described herein have a high content of active marrow.

In some embodiments of the current invention the radiation protection device may be configured to protect a bone or bones that have a relatively small surface area to volume ratio, requiring that the radiation protection device be of a minimal surface area. In another embodiment of the current invention, the radiation protection device may be configured so that the smaller the surface area of the radiation protection device as described herein, the greater its thickness may be. It is another embodiment of the current invention of the radiation protection device as described herein that the radiation protection device may be configured to have the smallest surface area possible without compromising protection of the protected marrow.

In some embodiments of the current invention, the radiation protection device may be configured to protect a bone or bones that lie as close as possible to the center of gravity of the body to be protected. In another embodiment of the current invention, the radiation protection device as described herein may be configured to be placed as close as possible to the center of gravity of the body to be protected. In another embodiment of the current invention, the radiation protection device as described herein may be configured to be placed as close as possible to the body's center of gravity, so as to have minimal impact on the protected subject's maneuverability. In an embodiment of the current invention, the radiation protection device may be configured to protect a bone or bones that lie in the pelvic girdle. In an embodiment of the current invention, the radiation protection device may be configured to protect a bone or bones that comprise the iliac bones. In an embodiment of the current invention the radiation protection device may be configured to protect a bone or bones that comprise the sacral bone. In an embodiment of the current invention, the radiation protection device may be configured to protect a bone or bones that comprise the pubic bone. In an embodiment of the current invention, the radiation protection device may be configured to protect a bone or bones that comprise the lumber vertebrae.

In nuclear disasters, radioactive materials may appear in the form of nuclear fallout. Thus, in an embodiment of the current invention the radiation protection device as described herein may be configured to protect a selected marrow from radioactive fallout. In another embodiment of the current invention, the radiation protection device may be configured to protect a body part from fallout in the form of a cloud of radioactive particles surrounding the wearer. In another embodiment of the current invention, the radiation protection device may be configured to protect a selected marrow from radiation emanating from several directions. In another embodiment of the current invention, the radiation protection device may be configured to attenuate radiation emanating from several directions. In another embodiment of the current invention the radiation protection device may be configured to provide spherical protection to a selected marrow. In another embodiment of the current invention the radiation protection device may be configured to provide sphere-like protection to a selected marrow. In another embodiment of the current invention the radiation protection device may be configured to provide circumferential protection to a selected marrow. In another embodiment of the current invention, the radiation protection device may be configured to complement the natural radiation-attenuating properties of the tissue surrounding the selected marrow to provide spherical protection to the selected marrow. In another embodiment of the current invention, the radiation protection device may be configured to complement the natural radiation-attenuating properties of the tissue surrounding the selected marrow to provide sphere-like protection to the selected marrow. In another embodiment of the current invention, the radiation protection device may be configured to complement the natural radiation-attenuating properties of the tissue surrounding the selected marrow to provide circumferential protection to the selected marrow.

In some embodiments of the current invention, the radiation protection device may be configured to cover body surfaces which are adjacent to the protected bone marrow in order to sufficiently attenuate any radiation approaching the bone marrow through the body of the protected subject.

In some embodiments, the radiation protection device may be configured to selectively shield an active marrow to provide an effective means of dramatically reducing the weight of the radiation protection device compared to non-selective strategies.

In some embodiments, THE radiation protection device may have a circumferential arrangement. In some embodiments, a radiation protection device may be configured to wrap around the area of the body containing the bone marrow selected for protection. In some embodiments, a radiation protection device may be configured to hermetically wrap around the area of the body containing the bone marrow selected for protection. In some embodiments, a radiation protection device may be configured to wrap around the area of the body containing the bone marrow selected for protection while providing unbroken attenuation throughout the surface of the device. In some embodiments, a radiation protection device may be configured to wrap around the area of the body containing the bone marrow selected for protection in the absence of hinges, axes or pivots.

In some embodiments of the present invention, a radiation protection device may be configured to cover body surfaces which are adjacent to the protected bone marrow in order to sufficiently attenuate any radiation approaching the bone marrow through the body of the wearer.

In some embodiments of the present invention, the radiation protection device may include one or a plurality of layers of a shielding material. In some embodiments, the radiation protection device may be designed to be placed on a body organ of a subject, which includes a concentration of active bone marrow.

According to some embodiments of the present invention, a radiation protection device for providing a selective protection of a specific body part that includes an active (i.e. red) bone marrow from radiation is provided. The device may include a radiation attenuating material designed to be placed adjacent to and externally cover only a portion of the body that includes the body part.

In some embodiments, the radiation protection device may incorporate into its design the natural radiation-blocking ability of the underlying tissue. In the hip, for example, the bone marrow is present mostly in the posterior area. Thus, the anterior abdominal area may serve to naturally attenuate radiation entry from frontal sources. In addition, different tissues (bone, muscle, adipose) may have different radiodensity. A radiation protection device according to embodiments of the invention may bring into account the natural shielding properties of human tissue by being non-uniform in the distribution of radiation attenuating material. This may be embodied in a radiation protection device employing a radiation attenuating material in varying thicknesses or conversely by employing materials of different attenuation ability while maintaining the same thickness throughout. The radiation attenuation level of a specific section of the device herein would be inversely related to the radiation attenuation levels of the underlying tissue around the target for protection. The radiation attenuation levels of the underlying tissue around the target for protection are typically determined by the thickness and radiodensity of that tissue. This characteristic may effectively minimize the overall weight of the device to make it bearable to carry.

In some embodiments, the design of the radiation protection device may take into account the natural shielding properties of human tissue by having a varying thickness. In some embodiments, the radiation protection device may have a varying thickness which is inversely related to the thickness and radiodensity of the underlying tissue at each location surrounding the target for protection. In some embodiments, at any given location on the radiation protection device, radiation attenuation may be different, to accommodate the variation in tissue thickness and radiodensity in the circumference of the protected marrow. In some embodiments, the radiation protection device may be designed by taking into account the natural radiation attenuating properties of the tissue surrounding the protected marrow and thus reduce shield weight substantially without compromising protection. In some embodiments, incorporating the natural radiation attenuating properties of the tissue surrounding the protected marrow in the design considerations of the radiation protection device may ensure that the total attenuation provided by the device in combination with the underlying tissue is substantially uniform in all directions.

In some embodiments, an individual using a radiation protection device according to embodiments of the invention may withstand radiation levels up to the point where tissues other than bone marrow are likely to sustain major damage. Since the second most radiosensitive tissue is the gut, and the gut sustains irreversible damage at about 1100 rad (11 Gy), embodiments of the radiation protection device may be designed to confer protection to bone marrow at least up to a dose of 1100 rads (11 Gy).

According to current practice between 23 and 58 grams of red bone marrow may be harvested on average for bone marrow transplants (mass reflecting net bone marrow not including blood and other infiltrates). According to some embodiments of the current invention, the radiation protection device as described herein may protect from death by irradiation at least 23-58 grams of red bone marrow, depending on body size. In some embodiments of the current invention, the amount and distribution of radiation attenuating material needed may be determined using the following formula:

$$A_R(x, y, z) = \frac{A_D}{A_T}, \qquad (1)$$

where $A_R$ is the required radiation attenuation at point x,y,z, $A_D$ is the total desired radiation attenuation and $A_T$ is the tissue radiation attenuation between point x,y,z and the bone marrow concentration.

According to some embodiments of the present invention, the radiation attenuating material may comprise sections of different radiation attenuation levels.

According to embodiments of the present invention, the radiation protection device has varying radiodensity in a manner accommodating the natural attenuation properties of the underlying various body organs and tissues.

According to some embodiments of the present invention, the radiation protection device may be of varying radiodensity in a manner accommodating the natural attenuation properties of the underlying various body organs and tissues.

Bone marrow concentrations are known in humans.

FIG. 1 illustrates a perspective view of a radiation protection device embodied as a helmet assembly 100 in accordance with an embodiment of the present invention. Radiation protection helmet assembly 100 is designed for protecting the head of a user against radiation. Helmet assembly 100 may include a base 102 surrounding the neck of the user. Helmet assembly 100 may include radiation shielding material. Helmet assembly 100 may include helmet 101 which includes a transparent visor 103, an air filtration device 108 with an air filter that includes intake 104 and outtake apertures 105, a sealable opening 106 allowing for the intraosseous injection of chemical or biological agents into the underlying skull marrow and a closure mechanism 107 for the fastening of the helmet 101 to the base 102.

Figure 2:
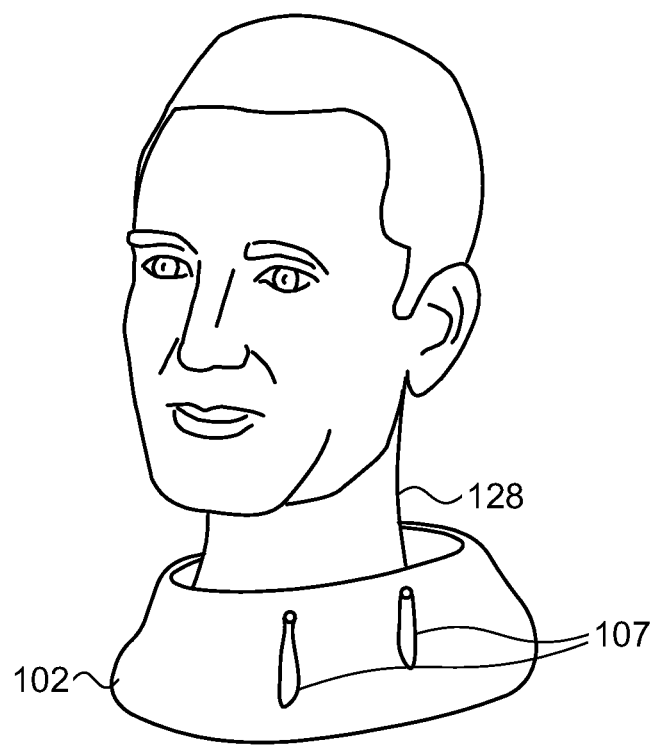
FIG. 2 is a perspective view of the base 102, shown in FIG. 1, upon which the helmet 101 (also shown in FIG. 1) may be mounted.

FIG. 2 is a perspective view of the base 102, shown in FIG. 1, upon which the helmet 101 (also shown in FIG. 1) may be mounted. Base 102 may comprise radiation attenuating material that is of flexible nature such that it accommodates a mounted helmet. It may be placed on the neck of the user 128 so that the cervical vertebrae of the user are protected from radiation. Base 102 may include a fastening mechanism 107 for fastening it to the helmet 101. The base 102 is helpful in supporting the weight of the helmet 101 (see FIG. 1).

Figure 3:
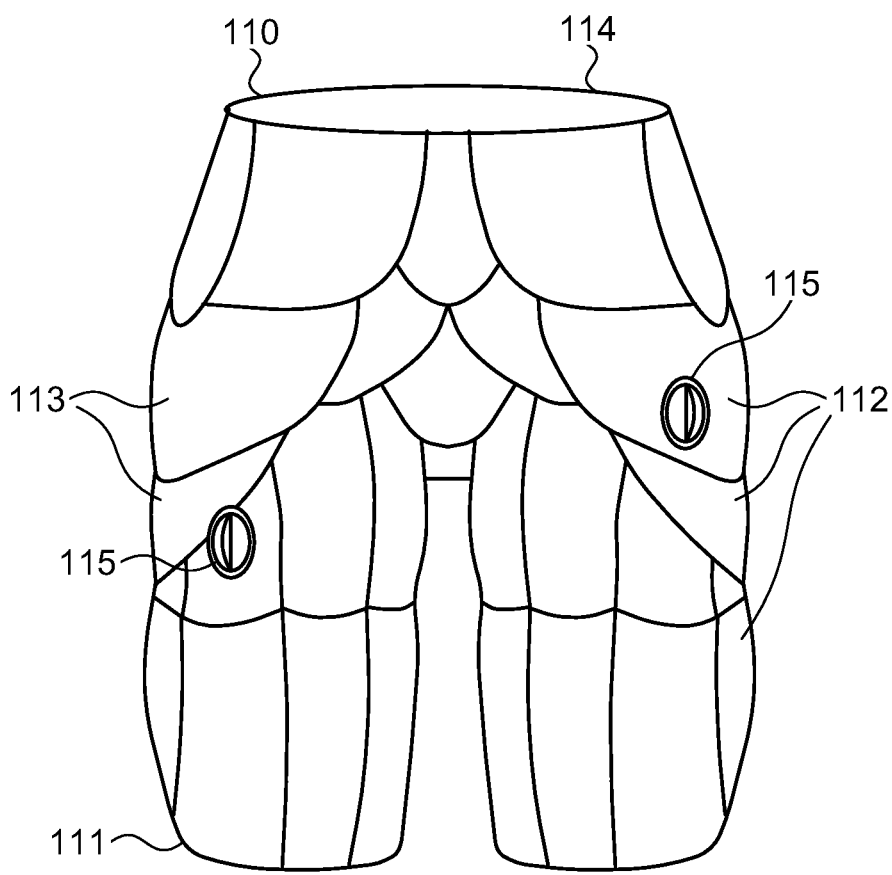
FIG. 3 is a perspective view of a radiation protection device 109 embodied as a bifurcated garment, in accordance with an embodiment of the present invention.

FIG. 3 is a perspective view of a radiation protection device 109 formed as a bifurcated garment, in accordance with an embodiment of the present invention. Device 109 is designed to protect the pelvic area by engulfing the waist 110, and extending down to the knee 111 of the user to protect the whole femur bone 112. It consists of several intercalating pieces (resembling a roof-tile or fish scale arrangement) of radiation shielding material 113 allowing for easy accommodation to individuals of different sizes and designed to be flexible enough so that it practically does not affect locomotion. The upper portion of the radiation protection device may include elastic fabric 114 that may be tightened around the waist to fix the device to the hips of the user. Device 109 may include sealable openings 115 allowing for the intraosseous injection of chemical or biological agents into the underlying femur bones.

In accordance with some embodiments of the present invention, a radiation protection device may have a varying radiation attenuation capability throughout its surface area. In one such an example, the radiation protection device may be made of radiation-attenuating material of a single density, but distributed in different thicknesses throughout the area of the device. In another example, the radiation protection device may be comprised of multiple radiation-attenuating materials having different densities but distributed in a similar thickness throughout the area of the device.

In some embodiments of the present invention, a radiation protection device may include radiation-attenuating material in particulate form which is distributed in a varying manner so as to provide varying protection levels throughout the area of the device.

Figure 4:
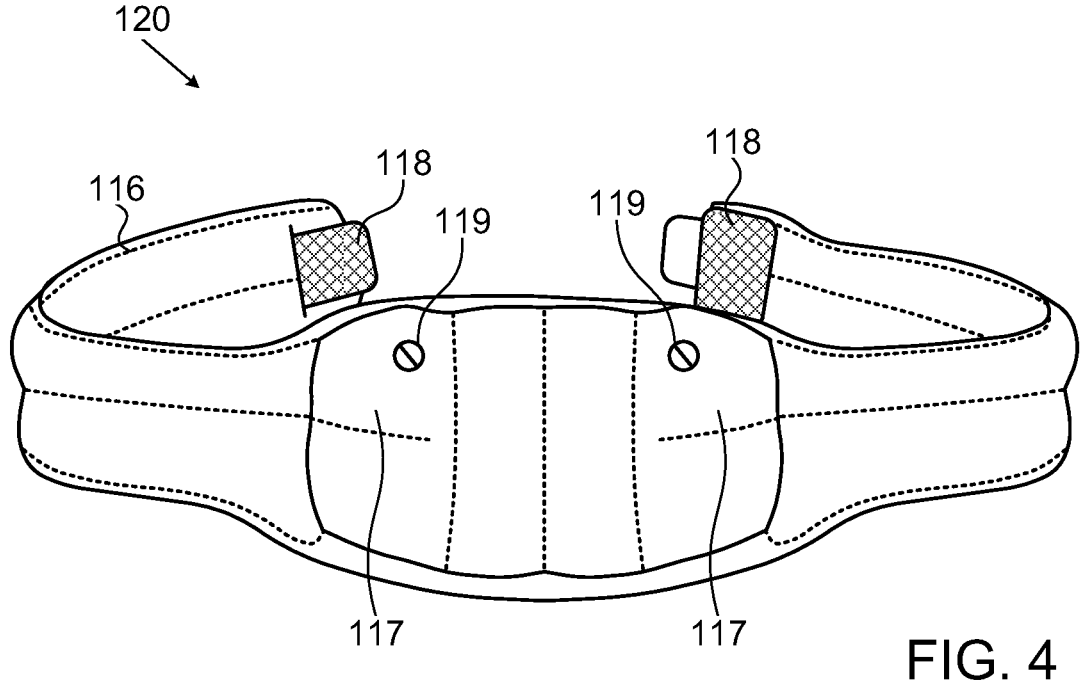
FIG. 4 is a perspective view of a radiation protection device in accordance with an embodiment of the present invention embodied as a belt.

FIG. 4 is a perspective view of a radiation protection device 120 in accordance with an embodiment of the present invention in the form of a belt 116 for placing around the waist of an individual for protecting the hip bones (including sections of the ilium, ischium, and pubis), the sacrum and the coccyx. Radiation protection device 116 may include elastic fabric (e.g neoprene) knitted around large numbers of small particles (e.g. spherical particles having a diameter of 1-6 mm) made from a radiation shielding material (e.g lead shot). The number of spherical particles contained within the fabric may vary. For example, the number of the spherical particles may be increased in sections covering areas that are rich in bone marrow such as the iliac crest 117. The belt may be provided with a fastening mechanism (e.g. Velcro fasteners 118). The radiation protection device 120 may include sealable openings 119 allowing for the intraosseous injection of chemical or biological agents into the underlying hip bones.

Figure 5:
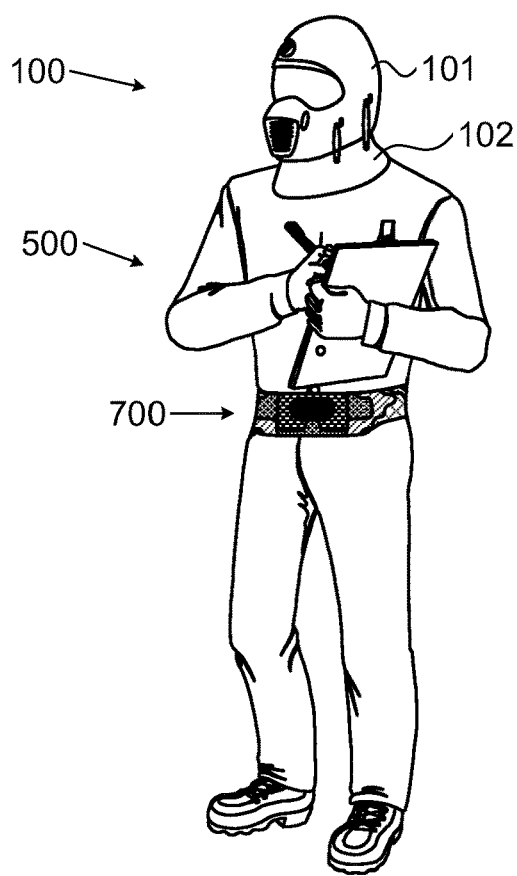
FIG. 5 illustrates the use of two radiation protection devices—embodied in the forms a helmet and a belt—by a person facing ionizing radiation, in accordance with embodiments of the present invention.

FIG. 5 illustrates the use of two radiation protection devices—embodied in the forms a helmet 100 and a belt 700—by a person 500 facing ionizing radiation, in accordance with embodiments of the present invention. It may be prudent to aim at increasing the protection coverage of body parts which include high concentrations of active bone marrow, by providing a plurality of radiation protection devices, according to embodiments of the invention, for protecting different such body parts.

In some embodiments of the invention, using a plurality of radiation protection devices, according to embodiments of the invention, to protect different such body parts may lend itself to reducing radiation attenuation level of each such device. This is because if more active bone marrow is provided with protection it may be possible to reduce the level of protection given to each body part. This could mean providing radiation attenuating material which is thinner and therefore lighter, thus reducing the weight of each radiation protection device, and facilitating greater maneuverability to the user.

In some embodiments of the invention using a plurality of radiation protection devices, according to embodiments of the invention, to protect multiple body parts could lend itself to securing the viability of a critical volume of active bone marrow to allow for recovery post-irradiation.

Figure 6:
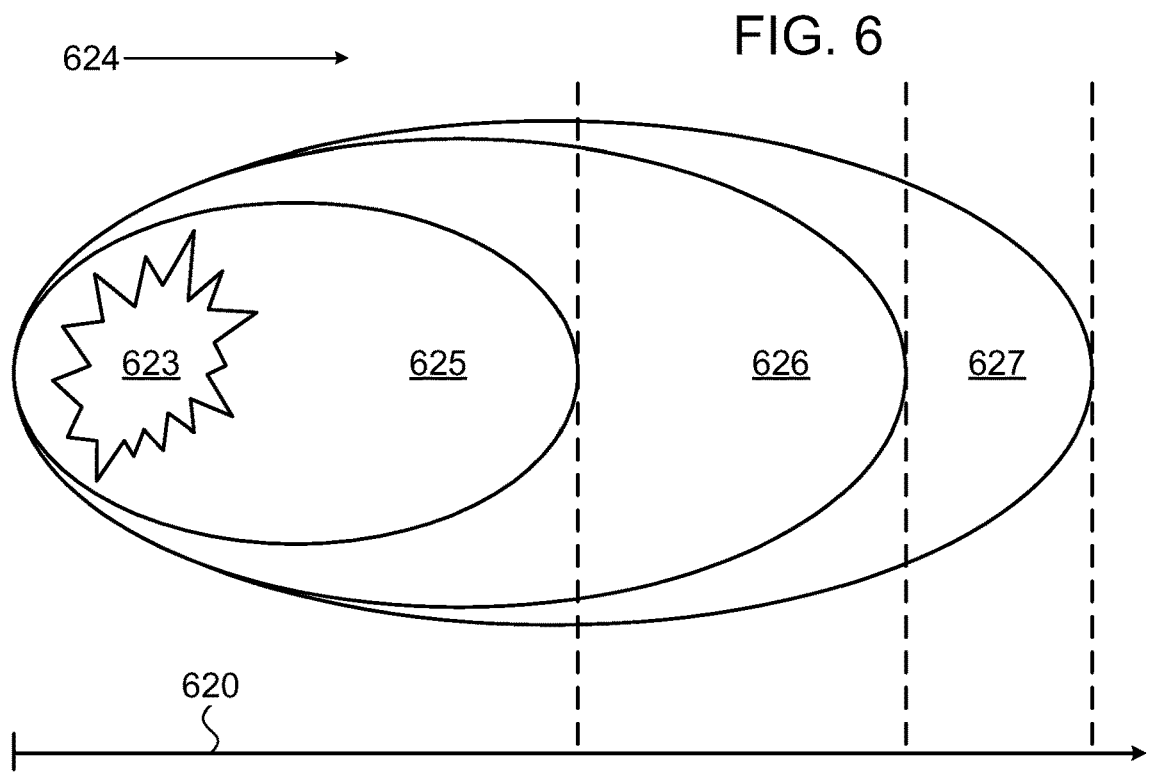
FIG. 6 illustrates impact zones of a nuclear explosion or a radiation leak.

FIG. 6 illustrates the impact zones of a nuclear explosion or radiation leak. An individual utilizing a radiation protection device in accordance with embodiments of the present invention may enjoy increased chances of survival in any event of exposure to ionizing radiation. Under the influence of a wind blowing in a certain direction 624, an immediate danger zone 625 is formed around the location of the nuclear explosion or radiation leak site (also referred to as "ground zero"). The wind direction 624 dictates shaping the immediate danger zone 625 in oval form. All inhabitants within the immediate danger zone 625 (e.g., flora and fauna, and any other objects) are most likely to be subjected to lethal radiation exposure, an electromagnetic pulse, a shock wave, firestorms, and super-strong winds. The chances of survival in the immediate danger zone 625 are practically none. A secondary danger zone 626, which surrounds the immediate danger zone 625 would still contain very high radiation levels which is a result of nuclear fallout being spread downwind. Living creatures (humans, animals) found in the secondary danger zone 626 would normally be subjected to lethal radiation and consequently die, but those protected by a radiation protection device in accordance with embodiments of the present invention would stand a chance of surviving due to the shielding effect of the device. A further safety zone 627 indicates the zone in which the radiation levels are below a danger level. Thus, individuals equipped with a radiation protection device in accordance with embodiments of the present invention can safely exit the danger zone or be safely evacuated.

The hematopoietic system (of humans and animals) is highly sensitive to ionizing radiation. Doses of 70 rad (0.7 Gy) and above are likely to cause decreased hematocrit, neutropenia and lymphopenia leading to anemia and immune suppression. A radiation protection device in accordance with some embodiments of the present invention may provide protection to erythroid, myeloid or lymphoid progenitors residing in the protected marrow preventing anemia and immune suppression resulting from decreased hematopoiesis under doses of 0.7 Gy and above. A radiation protection device according to some embodiments of the present invention may be designed to provide protection to pelvic parts of the body where both bone marrow concentrations and adjacent lymph nodes (e.g inguinal, mesenteric) are found.

For children, a radiation protection device according to some embodiments of the present invention may be designed to provide protection to the skull marrow and to the adjacent mandibular lymph nodes so as to both preserve a sufficient number of HSCs for effective hematopoiesis and enough lymphocytes to maintain immunity to pathogens.

In some embodiments, a radiation protection device may be designed to protect a bone marrow to prevent decreased lymphocyte counts and immune suppression under doses of 150 rad (1.5 Gy) and above.

In some embodiments, a radiation protection device may be designed to protect a bone marrow so as to prevent bone marrow aplasia under doses of 70 rad (0.7 Gy) and above.

In another embodiment, a radiation protection device may be designed to protect a bone marrow so as to prevent bone marrow aplasia under doses of 150 rad (1.5 Gy) and above.

In another embodiment, a radiation protection device may be designed to protect a bone marrow so as to prevent major bone marrow cell loss under doses of 70 rad (0.7 Gy) and above.

In another embodiment, a radiation protection device may be designed to protect a bone marrow so as to prevent major bone marrow cell loss under doses of 150 rad (1.5 Gy) and above. A radiation protection device according to embodiments of the present invention may be designed to block or greatly attenuate the amount of radiation that can pass through it. In some embodiments, a radiation protection device is radiopaque. In some embodiments, a radiation protection device may comprise a radiation-attenuating compound. In some embodiments, a radiation protection device may comprise a radiation-attenuating material. In some embodiments, a radiation protection device may comprise layers of a radiation attenuating compound or material.

FIG. 7A illustrates a radiation attenuating component of a radiation protection device in the form of a layered sheet assembly 700, which is designed to be worn by a human over the low back and about the waist. Radiation attenuating material is provided in the form of multiple uniquely shaped sheets of radiation attenuating material which when layered upon each other form a radiation protection device of a topography inversely related to the thickness and density of the tissue present between the device and the protected bone marrow. Layered sheet assembly 700 has a varying radiation attenuation capability throughout its surface area being made of radiation-attenuating material of a single density, but distributed in different thicknesses throughout the area of the device. The layered sheet assembly generally seeks to provide the highest level of radiation protection to the posterior pelvis (including the iliac crest) where high concentrations of bone marrow exist.

The layered sheet assembly 700 is substantially symmetrical with respect to its middle portion which is designed to be placed adjacent to the posterior pelvis, having two similar arms extending along opposite sides of the hips. Portion 720 of the layered sheet assembly, which is to be placed directly over the posterior pelvis and is in closest proximity to the bone marrow targeted for protection, is comprised of the largest number of layers. Other portions of the plate assembly 700 are comprised of decreasing numbers of layers as the distance from the bone marrow targeted for protection increases—generally the more distant the plate portion is from the posterior pelvis the thinner it is. Albeit, some local spots about the layered sheet assembly are given a higher number of layers in order to conform with the radiation attenuation properties of tissues of different internal organs and parts within the protected body area. Thus, for example, the thickness at point 702 of the assembly may be 2 mm, at point 704 the thickness may be 3 mm, at point 706 the thickness may be 4 mm. The thickness at point 708 may be 5 mm, at point 712 it may be 6 mm and at point 710 it may be 7 mm. The thickness at point 714 may be 8 mm, at point 716 it may be 9 mm, at point 718 it may be 10 mm and at point 720 it may be 11 mm (all these measurements are given as an example and in no way limit the scope of the invention to cover other embodiments having other measurements). Thicknesses may vary with the anatomy of the subjected to be protected; for example, in an obese individual the distance between a given point on the radiation attenuation component and the center of active marrow chosen for selection may be larger than in a less obese individual due to the presence of a larger thickness of tissue. As the radiation attenuation of tissue is determined, among other factors, by its thickness, a larger distance between a point on the radiation attenuation component and the center of the necessitating less radiation attenuation at that point on the radiation attenuation component and hence less thickness.

The varying attenuation levels throughout layered sheet assembly 700 may also be accomplished by using multiple materials with different levels of radiation attenuation. Moreover, layered sheet assembly 700 may come in an array of sizes, to accommodate the distribution of waist sizes in the population targeted for protection. Layered sheet assembly may change in size in linear fashion but also in non-linear fashion if it is determined that soft tissue and bone marrow-containing tissue contribute differentially to observed changes in waist size.

Layered sheet assembly 700 may be adopted for any body part containing a quantity of active bone marrow sufficient to allow for hematopoietic reconstitution following radiation exposure.

In some embodiments, layered sheet assembly 700, or any radiation protection device aimed at protecting the pelvic bone marrow, may contain specialized extrusions for covering and protecting the adjacent inguinal lymph nodes for lymphocyte preservation and faster immune reconstitution following radiation exposure.

In some embodiments, the radiation attenuation component may include radiation attenuating material, for example metals and alloys comprising; lead, gold, silver, tungsten, etc. or any combination thereof. The radiation attenuating material may have several mechanical characteristics. The radiation attenuating material may be ductile (e.g., lead, gold silver and their alloys) may have high density (e.g., lead, tungsten and their alloys) may undergo plastic deformation (e.g., lead, gold, silver and their alloys). The radiation attenuation component may include layers comprising the radiation attenuating material, thus the radiation attenuation material may exhibit the ability to be rolled into sheets. The sheets may have thickness of for example: 1 mm, 2 mm, 4 mm, 6 mm, 8 mm, 10 mm, 11 mm or more. In some embodiments the radiation attenuation material may be chemically stable and/or corrosive resistant under electromagnetic ionizing radiation.

In some embodiments the radiation attenuation material layers (first type layers) may have the ability to slide one on top of the other to allow flexibility of the radiation protecting device. The layers may be worked and finished to have a surface roughness and minimal hardness that may allow ductile material to slide. Alternatively additional layers (second type layers) may be placed between at least some of the first type layers (i.e., the attenuation material layers). The second type layers may include material configured to allow sliding of the first type layers. For example, the second type layers may include a polymer. In some embodiments the second type layers may include a powder, for example carbon powder.

In some embodiments, the radiation attenuating material included in the radiation attenuation component may be held, supported, warped, included and/or encased in a support structure (e.g., frame). The support structure may be designed to hold the radiation attenuating material and allow bending of the radiation attenuation component to allow wrapping of the radiation protecting device over a human body and unwrapping the device from the human body. The support structure may include: rigid materials (e.g., steels, stainless steels, nickel alloys, cobalt alloys, aluminium alloys, etc), flexible materials (stainless steels, spring steels, nickel alloys, etc.), all may also have high strength. The support structure may include chemically stable and/or corrosive resistant materials under electromagnetic ionizing radiation. The support structure may be fabricated from such material (e.g., stainless steels) or may be fabricated from one material (e.g., carbon steel) and coated by a protective coating that may be chemically stable and/or corrosive resistant under electromagnetic ionizing radiation.

In some embodiments of the present invention, the radiation attenuating component of the radiation protection device described herein may be supported by a support structure. In some embodiments of the present invention, the radiation attenuating component of the radiation protection device described herein may be supported by a support structure which protects it from plastic deformation. In some embodiments of the present invention, the radiation attenuating component of the radiation protection device described herein may be supported by a support structure which improves its elasticity. In some embodiments of the present invention, the radiation attenuating component of the radiation protection device described herein may be supported by a support structure which allows it to elasticity deform. In some embodiments of the present invention, the radiation attenuating component of the radiation protection device described herein may be supported by a support structure which allows the radiation protection device to elasticity deform.

In some embodiments of the present invention, the radiation attenuating component of the radiation protection device described herein may be supported by a support structure which limits its bending radius when a subject wraps the radiation protection device around a body part containing active marrow. In some embodiments of the present invention, the radiation attenuating component of the radiation protection device described herein may be supported by a support structure which reduces its fatigue upon repetitive wrapping and unwrapping. In some embodiments of the present invention, the radiation attenuating component of the radiation protection device described herein may be supported by a support structure which prevents it from reaching its breakage point upon bending when a subject wraps the radiation protection device around a body part containing active marrow.

In some embodiments of the present invention, the radiation attenuating component of the radiation protection device described herein may be supported by a support structure which renders it reversibly bendable. In some embodiments of the present invention, the radiation attenuating component of the radiation protection device described herein may be supported by a support structure which allows the radiation protection device to elasticity deform. In some embodiments of the present invention, the radiation attenuating component of the radiation protection device described herein may be supported by a support structure which allows the radiation protection device to wrap around a protected subject or body part thereof and unwrap when not in use. In some embodiments of the present invention, the radiation attenuating component of the radiation protection device described herein may be supported by a support structure which increases the tendency of the radiation protection device to unwrap from around a protected subject or body part thereof when not fastened or unfastened. In some embodiments of the present invention, the radiation attenuating component of the radiation protection device described herein may be supported by a support structure which increases the tendency of the radiation protection device to bounce back when not fastened or unfastened.

In some embodiments of the present invention, the radiation attenuating component of the radiation protection device described herein may be supported by a support structure which is of high tensile strength. In some embodiments of the present invention, the radiation attenuating component of the radiation protection device described herein may be supported by a support structure which is resilient. In another embodiment of the present invention, the radiation attenuating component of the radiation protection device described herein may be supported by a support structure which is durable. In another embodiment of the present invention, the radiation attenuating component of the radiation protection device described herein may be supported by a support structure which is elastic. In another embodiment of the present invention, the radiation attenuating component of the radiation protection device described herein may be supported by a support structure which has mechanical properties similar to stainless steel.

In some embodiments of the present invention, the support structure supporting the radiation attenuating component of the radiation protection device described herein may be of a higher tensile strength than the radiation attenuating component it encases. In some embodiments of the present invention, the, the support structure supporting the radiation attenuating component of the radiation protection device described herein may be of a higher resilience than the radiation attenuating component it encases. In some embodiments of the present invention, the, the support structure supporting the radiation attenuating component of the radiation protection device described herein may be of a higher durability than the radiation attenuating component it encases. In some embodiments of the present invention, the, the support structure supporting the radiation attenuating component of the radiation protection device described herein may be of a higher rigidity than the radiation attenuating component it encases. In some embodiments of the present invention, the support structure supporting the radiation attenuating component of the radiation protection device described herein may be of a higher elasticity than the radiation attenuating component it encases.

In some embodiments of the present invention, the radiation attenuating component of the radiation protection device described herein may be malleable. In some embodiments of the present invention, the radiation attenuating component of the radiation protection device described herein may be ductile. In some embodiments of the present invention, the radiation attenuating component of the radiation protection device described herein may be both malleable and ductile.

In some embodiments of the present invention, the radiation attenuating component of the radiation protection device described herein may be more malleable than the support structure supporting it. In some embodiments of the present invention, the radiation attenuating component of the radiation protection device described herein may be more ductile than the support structure supporting it. In some embodiments of the present invention, the radiation attenuating component of the radiation protection device described herein may be more ductile and more malleable than the support structure supporting it.

In some embodiments of the present invention, the radiation attenuating component of the radiation protection device described herein may be both dense and malleable. In some embodiments of the present invention, the radiation attenuating component of the radiation protection device described herein may be both dense and ductile. In some embodiments of the present invention, the radiation attenuating component of the radiation protection device described herein may be dense, ductile and malleable.

In some embodiments of the present invention, the radiation attenuating component of the radiation protection device described herein may be denser than the support structure supporting it. In some embodiments of the present invention, the radiation attenuating component of the radiation protection device described herein may be denser and more malleable than the support structure supporting. In some embodiments of the present invention, the radiation attenuating component of the radiation protection device described herein may be denser and more ductile than the support structure supporting it. In some embodiments of the present invention, the radiation attenuating component of the radiation protection device described herein may be denser, more ductile and more malleable than the support structure supporting it.

In some embodiments of the present invention, the radiation attenuating component of the radiation protection device described herein may be soft. In some embodiments of the present invention, the radiation attenuating component of the radiation protection device described herein may be both soft and dense. In some embodiments of the present invention, the radiation attenuating component of the radiation protection device described herein may be both soft and ductile. In some embodiments of the present invention, the radiation attenuating component of the radiation protection device described herein may be soft, dense and ductile.

In some embodiments of the present invention, the radiation attenuating component of the radiation protection device described herein may be softer than the support structure supporting it. In some embodiments of the present invention, the radiation attenuating component of the radiation protection device described herein may be softer and denser than the support structure supporting it. In some embodiments of the present invention, the radiation attenuating component of the radiation protection device described herein may be softer and more ductile than the support structure supporting it. In some embodiments of the present invention, the radiation attenuating component of the radiation protection device described herein may be softer, denser and more ductile than the support structure supporting it.

In another embodiment of the present invention, the radiation attenuating component of the radiation protection device together with the support structure (e.g. a frame) supporting it comprises a core assembly of a radiation protection device. In another embodiment of the present invention, the core assembly of the radiation protection device comprises also components which aid in holding the core assembly together such as rivets and/or fastening bands and also components which protect the core assembly extremities and edges such as rigid pockets and elastomer-based linings, respectively.

In some embodiments of the present invention, the radiation protection device may comprise a sealing pouch. In some embodiments of the present invention, the radiation protection device may comprise a sealing pouch-encased core covered in a composite fabric. In some embodiments composite fabric may be presented in the form of a garment. In some embodiments composite fabric may be presented in the form of a belt. In some embodiments composite fabric may be presented in the form of a belt suspended by shoulder straps.

In some embodiments of the present invention, the radiation attenuating component of the radiation protection device may be encased in a frame comprising sheets of resilient material such as steel or stainless steel. In some embodiments of the present invention, the radiation attenuating component of the radiation protection device may be presented in the form of layers of radiation attenuating material such as lead and is encased in a frame comprised of sheets of resilient material. In some embodiments of the present invention, the radiation attenuating component of the radiation protection device may be interposed between sheets of resilient material. In some embodiments of the present invention, the radiation attenuating component of the radiation protection device may be interposed between sheets of resilient material of a length corresponding to the full length of the radiation attenuating component. In some embodiments of the present invention, the assembly of the radiation attenuating component of the radiation protection device and the sheets of resilient material which surround it may be held together in a manner that does not interfere with the wrapping and unwrapping of the radiation protection device from around a body part containing active marrow. In some embodiments of the present invention, the assembly of the radiation attenuating component of the radiation protection device and the sheets of resilient material which surround it may be held together in a manner that does not interfere with the relative movement of said sheets or any layers of the radiation attenuation component when wrapping and unwrapping the radiation protection device from around a body part containing active marrow. In some embodiments of the present invention, the assembly of the radiation attenuating component of the radiation protection device and the sheets of resilient material which surround it may be held together by straps. In some embodiments of the present invention, the assembly of the radiation attenuating component of the radiation protection device and the sheets of resilient material which surround it may be held together by bands or fastening bands. In some embodiments of the present invention, the assembly of the radiation attenuating component of the radiation protection device and the sheets of resilient material which surround it may be held together at predetermined discrete points along the sheets of high tensile strength material. In some embodiments of the present invention, the assembly of the radiation attenuating component of the radiation protection device and the sheets of resilient material which surround it may be held together at predetermined discrete points along the sheets of high tensile strength material by anchoring straps or bands to only one side of the encasing frame. In some embodiments of the present invention, the extremities of the assembly of the radiation attenuating component of the radiation protection device and the sheets of resilient material which surround it may be inserted into protective pockets which prevent bending of the extremities and blunt the sharpness of the sheets of resilient material.

In some embodiments of the present invention, the extremities of the assembly of the radiation attenuating component of the radiation protection device described herein and the frame of high tensile strength material which surrounds it may be inserted into protective pockets which have a depth corresponding with the maximal displacement of sheets of the assembly. Pockets may be manufactured by injection molding of polymers such as nylon and reinforced by glass fiber to obtain rigidity. In some embodiments, protective (rigid) pockets may attach only to the inner-most layer of the high tensile strength frame. In instances where the frame is comprised of high tensile strength sheets such as steel, the protective pockets may attach to inner-most sheet, closest to the protected subject. In some embodiments, when the radiation attenuating component is comprised of layers, rigid pockets allow the relative movement of more exterior layers when wrapping and unwrapping of radiation protection device.

In some embodiments of the present invention, the radiation attenuating component of the radiation protection device described herein may encase a frame. In another embodiment of the present invention, the radiation attenuating component of the radiation protection device described herein may encase a frame which protects it from plastic deformation. In another embodiment of the present invention, the radiation attenuating component of the radiation protection device described herein may encase a frame which improves its elasticity. In another embodiment of the present invention, the radiation attenuating component of the radiation protection device described herein may encase a frame which allows it to elasticity deform. In another embodiment of the present invention, the radiation attenuating component of the radiation protection device described herein may encase a high tensile strength frame. In another embodiment of the present invention, the radiation attenuating component of the radiation protection device described herein may encase a highly resilient frame. In another embodiment of the present invention, the radiation attenuating component of the radiation protection device described herein may encase a highly durable frame. In another embodiment of the present invention, the radiation attenuating component of the radiation protection device described herein may encase a highly elastic frame.

In some embodiments of the present invention, the frame encased by the radiation attenuating component of the radiation protection device described herein may be of a higher tensile strength than the radiation attenuating component it encasing it. In some embodiments of the present invention, the frame encased by the radiation attenuating component of the radiation protection device described herein may be of a higher resilience than the radiation attenuating component encasing it. In some embodiments of the present invention, the frame encased by the radiation attenuating component of the radiation protection device described herein may be of a higher durability than the radiation attenuating component it encasing it. In some embodiments of the present invention, the frame encased by the radiation attenuating component of the radiation protection device described herein may be of a higher rigidity than the radiation attenuating component encasing it. In some embodiments of the present invention, the frame encased by the radiation attenuating component of the radiation protection device described herein may be of a higher elasticity than the radiation attenuating component encasing it.

In some embodiments of the present invention, the radiation attenuating component of the radiation protection device described herein may be supported by a frame. In another embodiment of the present invention, the radiation attenuating component of the radiation protection device described herein may be supported by a frame which protects it from plastic deformation. In another embodiment of the present invention, the radiation attenuating component of the radiation protection device described herein may be supported by a frame which improves its elasticity. In another embodiment of the present invention, the radiation attenuating component of the radiation protection device described herein may be supported by a frame which allows it to elastically deform. In another embodiment of the present invention, the radiation attenuating component of the radiation protection device described herein may be supported by a high tensile strength frame. In another embodiment of the present invention, the radiation attenuating component of the radiation protection device described herein may be supported by a highly resilient frame. In another embodiment of the present invention, the radiation attenuating component of the radiation protection device described herein may be supported by a highly durable frame. In another embodiment of the present invention, the radiation attenuating component of the radiation protection device described herein may be supported by a highly elastic frame. In another embodiment of the present invention, the radiation attenuating component of the radiation protection device described herein may be supported by a highly elastic frame which influences the device to unwrap from around a body part containing active marrow when removing said device.

In one embodiment of the present invention, the radiation attenuating component of the radiation protection device described herein may be supported by a 0.1-3 mm steel frame. In another embodiment of the present invention, the radiation attenuating component of the radiation protection device described herein may be supported by a 0.1-3 mm stainless steel frame. In a further embodiment of the present invention, the radiation attenuating component of the radiation protection device described herein may be supported by a carbon fiber frame. In a still further embodiment of the present invention, the radiation attenuating component of the radiation protection device described herein may be supported by a poly-carbonate frame.

In some embodiments of the present invention, the frame supporting the radiation attenuating component of the radiation protection device described herein may be of a higher tensile strength than the radiation attenuating component it supports. In some embodiments of the present invention, the frame supporting the radiation attenuating component of the radiation protection device described herein may be of a higher resilience than the radiation attenuating component it supports. In some embodiments of the present invention, the frame supporting the radiation attenuating component of the radiation protection device described herein may be of a higher durability than the radiation attenuating component it supports. In some embodiments of the present invention, the frame supporting the radiation attenuating component of the radiation protection device described herein may be of a higher rigidity than the radiation attenuating component it supports. In some embodiments of the present invention, the frame supporting the radiation attenuating component of the radiation protection device described herein may be of a higher elasticity than the radiation attenuating component it supports.

In some embodiments of the present invention, the radiation attenuating component of the radiation protection device described herein may be made of a material which provides for easy wrapping of the device around a body part containing active marrow. In another embodiment of the present invention, the radiation attenuating component of the radiation protection device described herein may be supported by a frame which provides for easy unwrapping of the device from around a body part containing active marrow. In another embodiment of the present invention, the radiation attenuating component of the radiation protection device described herein may plastically deform when wrapping the device around a body part containing active marrow. In another embodiment of the present invention, the radiation attenuating component of the radiation protection device described herein may be supported by a frame which elastically deforms when wrapping the device around a body part containing active marrow. In another embodiment of the present invention, the radiation attenuating component of the radiation protection device described herein may plastically deform while the frame supporting it elastically deforms when wrapping the device around a body part containing active marrow. In another embodiment of the present invention, the plastic deformability of the radiation attenuating component of the radiation protection device described herein may be outweighed by the elasticity of the frame supporting it. In another embodiment of the present invention, the plastic deformation of the radiation attenuating component of the radiation protection device described herein may be reversed by the elasticity of frame supporting it when unwrapping the device from around a body part containing active marrow. In another embodiment of the present invention, the radiation protection device described herein may be elastically deformed when wrapping the device around a body part containing active marrow.

In accordance with some embodiments, the radiation attenuating component may be presented in the form of layers of radiation attenuating material. In another embodiment, the radiation attenuating component may be presented in the form of layers of radiation attenuating material which are bound together at their axis of symmetry. In another embodiment, the radiation attenuating component may be presented in the form of layers of radiation attenuating material which are bound together only at their axis of symmetry. In another embodiment, the axis of symmetry of the layers of radiation attenuating material comprising the radiation attenuating component may run along the spinal column of the protected subject. In another embodiment, the radiation attenuating component may be presented in the form of layers of radiation attenuating material which are bound together in a way which allows relative movement between said layers when said component is wrapped around a body part containing active marrow.

In some embodiments, the radiation attenuating component may be presented in the form of layers of radiation attenuating material which are bound together by use of rivets. In another embodiment, the radiation attenuating component may be presented in the form of layers of radiation attenuating material which are bound together by use of lead rivets. In another embodiment, the radiation attenuating component may be presented in the form of layers of radiation attenuating material which are bound together by use of bands. In another embodiment, the radiation attenuating component may be presented in the form of layers of radiation attenuating material which are bound together in any fashion that allows relative movement of said layers when wrapping and unwrapping the radiation protection device from around a body part containing active marrow.

In some embodiments, the radiation attenuating component may be presented in the form of layers of radiation attenuating material which are coated with a material which reduces the coefficient of friction between them. In another embodiment, the radiation attenuating component may be presented in the form of layers of radiation attenuating material which are separated from each other by sheets of a material which reduces the coefficient of friction between them. In another embodiment, the radiation attenuating component may be presented in the form of layers of radiation attenuating material which are separated from each other by a powder of a material which reduces the coefficient of friction between them. In another embodiment, the radiation attenuating component may be presented in the form of layers of radiation attenuating material which are separated from each other by a solution of a material which reduces the coefficient of friction between them. In another embodiment, the material which reduces the coefficient of friction between the layers of radiation attenuating material comprising the radiation attenuating component may be Polytetrafluoroethylene (PTFE, Teflon), polyamide-imide (PAI), Nylon 6-6, Nylon 4-6, graphite, graphite powder, acetal homopolymer or carbon fiber.

In some embodiments, the radiation attenuating component may be presented in the form of layers of radiation attenuating material which are coated with a material which facilitates relative movement of said layers when wrapping and unwrapping the radiation protection device from around a body part containing active marrow. In another embodiment, the radiation attenuating component may be presented in the form of layers of radiation attenuating material which are separated from each other by sheets of a material which facilitates relative movement of said layers when wrapping and unwrapping the radiation protection device from around a body part containing active marrow. In another embodiment, the radiation attenuating component may be presented in the form of layers of radiation attenuating material which are separated from each other by a powder of a material which facilitates relative movement of said layers when wrapping and unwrapping the radiation protection device from around a body part containing active marrow. In another embodiment, the radiation attenuating component may be presented in the form of layers of radiation attenuating material which are separated from each other by a solution of a material which facilitates relative movement of said layers when wrapping and unwrapping the radiation protection device from around a body part containing active marrow. In another embodiment, the material which facilitates relative movement of said layers when wrapping and unwrapping the radiation protection device from around a body part containing active marrow may be Polytetrafluoroethylene (PTFE, Teflon), polyamide-imide (PAI), Nylon 6-6, Nylon 4-6, graphite, graphite powder, acetal homopolymer, carbon fiber or a lubricant.

In some embodiments, the radiation protection device as described herein may serve as a harness or part of a harness for supporting a self-contained breathing apparatus (SCBA). In another embodiment, the radiation attenuation component of the radiation protection device as described herein may be removed. In one embodiment removal may occur when radiation levels subside. In another embodiment removal may occur when it is disadvantageous for the protected subject to bear the weight of the radiation attenuation component.

In some embodiments, the fabric encasement of the radiation protection device as described herein may serve as a harness or part of a harness for supporting a self-contained breathing apparatus (SCBA). In another embodiment, a radiation attenuation component of the radiation protection device as described herein may be inserted into the fabric encasement. In another embodiment, a radiation attenuation component of the radiation protection device as described herein may be attached to the fabric encasement. In one embodiment, insertion or attachment of the radiation attenuation component may occur when certain radiation levels are detected. In another embodiment insertion or attachment of the radiation attenuation component may occur when certain radiation levels are anticipated. In another embodiment, the SCBA-supporting fabric encasement of the radiation protection device as described herein may include a blower for dispersal of radioactive fallout. In another embodiment, the SCBA-supporting encasement of the radiation protection device as described herein may be attached to a blower when certain levels of radiation are detected. In another embodiment, the SCBA-supporting encasement of the radiation protection device as described herein may be attached to a blower when certain levels of radiation are anticipated. In another embodiment, the SCBA-supporting encasement of the radiation protection device as described herein may be attached to a blower which receives its pressurized gas from the SCBA gas tank or tanks.

In some embodiments a method for protecting a subject from both external radiation and internal contamination with radioactive particles is described. In one embodiment, a method for protecting a subject from both external radiation and internal contamination with radioactive particles may include the step of adorning a radiation protection device as described herein. In another embodiment, a method for protecting a subject from both external radiation and internal contamination with radioactive particles may include the step of adorning a respirator. In another embodiment, a method for protecting a subject from both external radiation and internal contamination with radioactive particles may include the step of adorning a self-contained breathing apparatus (SCBA). In another embodiment, a method for protecting a subject from both external radiation and internal contamination with radioactive particles may include the step of adorning a SCBA-supporting radiation protection device as described herein with a SCBA connected to it.

FIG. 7B illustrates the layer assembly of the radiation attenuating component 700 shown in FIG. 7A with a protective cover 730, according to embodiments of the present invention. Protective cover 730 may be needed to prevent damages from being incurred to the radiation attenuating material. Lead, for example, is a good radiation attenuating material but may easily deform as a result of an inadvertent blow or an external force being exerted upon it. A protective cover 730 may be made of a hard and durable yet relatively light material, such as for example, plastic. A protective cover 730 may further be made of a radiation attenuating fabric. Protective cover 730 may also serve as a harness or a component in a harness for carrying a self-contained breathing apparatus (SBCA). Layered sheet assembly 700 may be quickly removed from protective cover 730. Removal of layered assembly 700 may occur once radiation levels subside. Protective cover 730 may also serve as a harness or a component in a harness for carrying a self-contained breathing apparatus (SBCA) in the absence of a radiation attenuation component. Layered sheet assembly 700 may be quickly added into protective cover 730. Adding in of layered assembly 700 may occur once dangerous levels of radiation are detected.

Figure 7C:
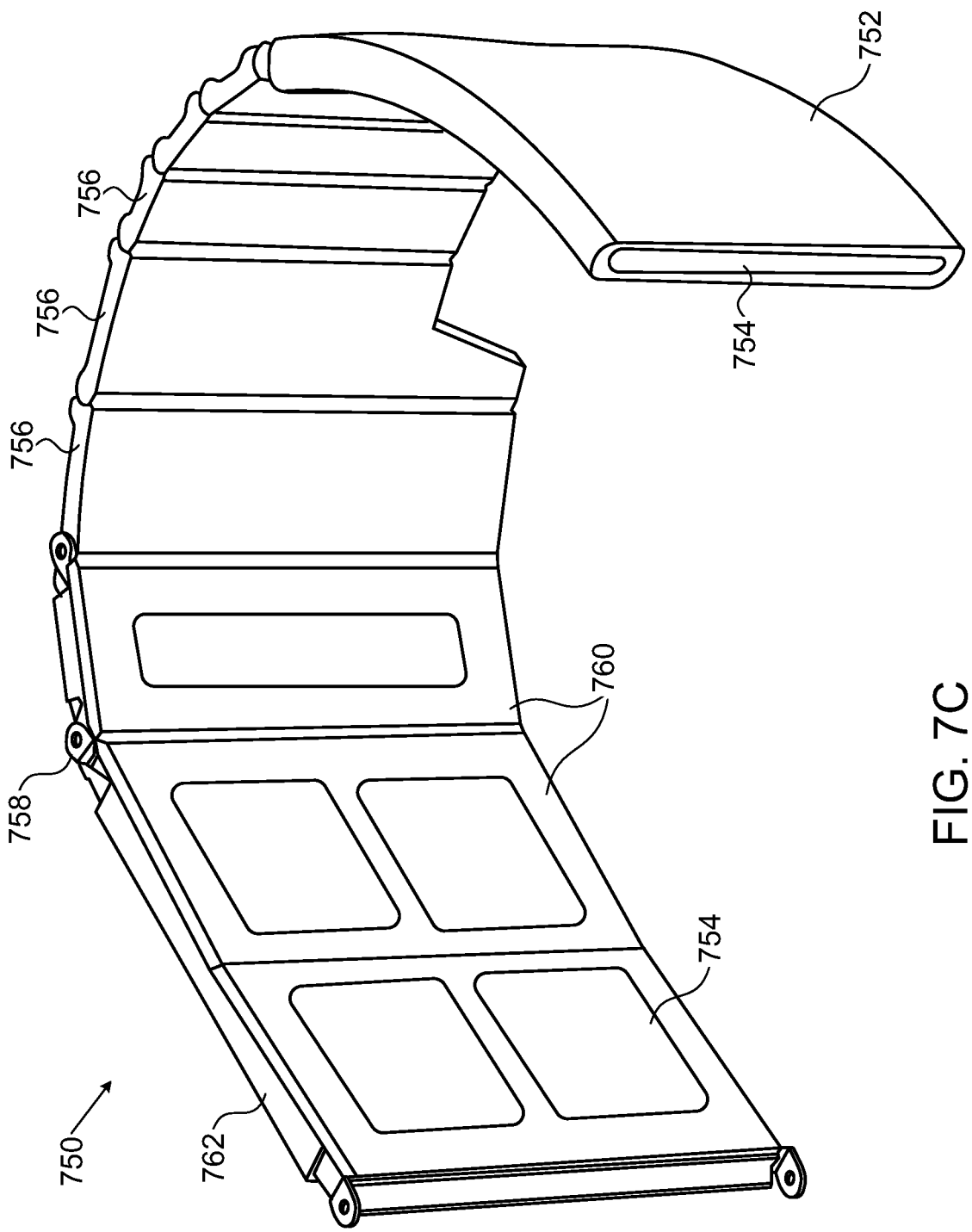
FIG. 7C illustrates a plate assembly for a radiation attenuating component for a radiation protection device in accordance with other embodiments of the present invention.

FIG. 7C illustrates a plate assembly 750 for radiation attenuating material of a radiation protection device in accordance with other embodiments of the present invention. Plate assembly 750 comprises a plurality of hinged sections 756, connected one to the other by hinges 758. Each section comprises radiation attenuating material distributed in varying thickness inversely related to the thickness and density of the tissue present between a particular point in the section and the protected bone marrow. Sections interface with on another in a manner that there is no interval in radiation attenuating material continuity. The radiation attenuating material may be provided in the form of plates 754. The radiation attenuating material may be placed in an external sheath 752. Some or all sections may include frames 760 which hold the radiation attenuating material (e.g. hold thicker radiation attenuating plates). Housing 762 may be provided for some or all sections for additional structural strength.

Embodiments of the radiation protection device may include radiation attenuating material in many forms, such as, for example plates, blocks, sheets, particles, solution, fibers. In some embodiments, a radiation protection device may be formed as a garment. In some embodiments, fibers comprising a radiation attenuating material are woven into a garment or interwoven with conventional garment material, such as cloth, to provide both the flexibility of a cloth garment and the radiation protection of metallic lead garment.

In some embodiments, the radiation attenuating material is in the form of small particles. The particles may be of any size, such as, for example, millimeter sizes, micron sizes or/and submicron sizes.

In some embodiments, the radiation protection device comprises lining. The lining may include an elastic material and may be made of cloth comprising an elastic material. In some embodiments, the lining may include neoprene. In some embodiments, the lining may be made of fibers comprising radiation attenuating compound or material that are woven into the lining or interwoven with conventional lining material.

In some embodiments the radiation protection device may include an outer lining and/or an inner lining.

In some embodiments outer and inner linings are provided, joined together. In some embodiments, the outer and inner linings are stitched together. In some embodiments, one or a plurality of layers of radiation attenuating material is sandwiched between the inner and outer linings. The lining may be pliable, woven. It may be made of polymeric fabric, such as polychloroprene (e.g. Neoprene), polypropylene, polyethylene, aramid fabric, rayon, nylon or any mixture of these. In some embodiments, a lining is a woven fabric, such as cloth, or can be another flat, pliable material, such as paper or film.

A radiation protection device according to embodiments of the present invention may be worn over clothes or directly on the body of the wearer. In some embodiments, a radiation protection device may be worn under a protective suit such as a HaZMaT suit. In another embodiment, a radiation protection device may be worn over a protective suit such as a HazMaT suit. In another embodiment, a radiation protection device may be encased in a fire retardant casing. In another embodiment, a radiation protection device may be encased in a fallout-repellant casing. In another embodiment, a radiation protection device m encased in a casing which is both fallout-repellant and fire retardant.

In some embodiments, the radiation attenuating component of the radiation protection device described herein may be comprised of radiation attenuating material in the form of particles (e.g. lead shot) that is sandwiched between sheets of a polymeric fabric, such as polychloroprene (Neoprene), polypropylene, polyethylene, aramid fabric, rayon, nylon or any mixture of these to afford protection while allowing flexibility.

In some embodiments, radiation attenuating materials may be embedded in a polymeric mixture. In some embodiments, such a polymeric mixture may include a polymer, one or more radiation attenuating materials and one or more additives. In some embodiments, the polymer may be selected from a broad range of plastics including, but not limited to, polyurethane, polyamide, polyvinyl chloride, polyvinyl alcohol, natural latex, polyethylene, polypropylene, ethylene vinyl acetate (EVA), polyester, or any combination thereof. In some embodiments, an additive (typically a chemical) may be added to improve the flexibility, strength, durability or other properties of the radiation protection device or to ensure that the polymeric mixture has an appropriate uniformity and consistency. In some embodiments, an additive may comprise a plasticizer (e.g., epoxy soybean oil, ethylene glycol, propylene glycol, etc.), an emulsifier, a surfactant, a suspension agent, a leveling agent, a drying promoter, a flow enhancer etc. Those skilled in the plastic processing arts are familiar with the selection and use of such additives.

In some embodiments, a radiation attenuating material may comprise barium compounds, barium sulfate, barium chloride, tungsten compounds, tungsten carbide, tungsten oxide, tungsten, bismuth compounds, bismuth, lead, virgin lead, recycled lead, lead compounds, lead alloys, tantalum compounds, titanium, titanium compounds, diatrizoate meglumine, acetrizoate sodium, boron, boric acid, boron oxide, boron salts, other boron compounds, beryllium, beryllium compounds, bunamiodyl sodium, diatrizoate sodium, ethiodized oil, gold, lobenzamic acid, locarmic acid, locetamic acid, Iodipamide, Iodixanol, Iodized oil, Iodoalphionic acid, o-Iodohippurate sodium, demron, Iodophthalein sodium, Iodopyracet, loglycamic acid, Iohexol, lomeglamic acid, Iopamidol, lopanoic acid, Iopentol, Iophendylate, lophenoxic acid, water, Iopromide, lopronic acid, lopydol, lopydone, lothalamic acid, Iotrolan, Ioversol, loxaglic acid, Ioxilan, Ipodate, meglumine acetrizoate, meglumine ditrizoate methiodal sodium, metrizamide, metrizoic acid, phenobutiodil, phentetiothalein sodium, platinum, propryliodone, silver, sodium Iodomethamate, sozoiodolic acid, thorium oxide, trypanoate sodium, or any combination thereof, uranium and depleted uranium.

In some embodiments, a radiation attenuating component may comprise any material which attenuates gamma radiation better than human tissue. In some embodiments, a radiation attenuating component may comprise any material which attenuates gamma radiation better than tap water. In some embodiments, a radiation attenuating component may comprise any material which is denser than 1 gram per cubic centimeter.

In some embodiments, the radiation protection device may be comprised of materials soaked or dipped in a premade solution containing radiation attenuating material. The radiation attenuating material of the present invention can also be impregnated into a fabric using alternative techniques. In some embodiments, the fabric may include pores that are smaller in size than the particles of radiopaque material, but larger in size than the solvent (e.g., water or alcohol) used for the radiopaque solution. In some embodiments, the radiopaque solution may be passed through the fabric in a manner where the fabric acts as a filter to filter out the radiopaque particles while allowing the solvent to pass through.

A transmission attenuation factor of the radiation protection device may vary. In some embodiments, the radiation protection device may have a transmission attenuation factor of at least 20% of a primary 100 kVp x-ray beam. In some embodiments, the radiation protection device may have a transmission attenuation factor of at least 30% of a primary 100 kVp x-ray beam. In some embodiments, the radiation protection device may have a transmission attenuation factor of at least 40% of a primary 100 kVp x-ray beam. In some embodiments, the radiation protection device may have a transmission attenuation factor of at least 50% of a primary 100 kVp x-ray beam. In some embodiments, the radiation protection device may have a transmission attenuation factor of at least 60% of a primary 100 kVp x-ray beam. In some embodiments, the radiation protection device may have a transmission attenuation factor of at least 70% of a primary 100 kVp x-ray beam. In some embodiments, the radiation protection device may have a transmission attenuation factor of at least 75% of a primary 100 kVp x-ray beam Total attenuation of radiation transmission into a bone marrow is comprised of the attenuation factor of the radiation protection device at a given point multiplied with the attenuation factor of the underlying tissue. Total attenuation of radiation transmission may vary. In some embodiments, the Total attenuation of radiation transmission may be at least 40% of a primary 100 kVp x-ray beam. In some embodiments, the total attenuation of radiation transmission may be at least 50% of a primary 100 kVp x-ray beam. In some embodiments, total attenuation of radiation transmission may be at least 60% of a primary 100 kVp x-ray beam. In some embodiments, total attenuation of radiation transmission may be at least 70% of a primary 100 kVp x-ray beam. In some embodiments, total attenuation of radiation transmission may be at least 80% of a primary 100 kVp x-ray beam. In some embodiments, total attenuation of radiation transmission may be at least 90% of a primary 100 kVp x-ray beam. In some embodiments, total attenuation of radiation transmission may be at least 95% of a primary 100 kVp x-ray beam. In some embodiments, total attenuation of radiation transmission may be at least 97% of a primary 100 kVp x-ray beam.

In some embodiments, the total attenuation of transmission into a protected bone marrow of gamma radiation of an energy of 0.66 MeV may be at least 20%. In some embodiments, the total attenuation of transmission of gamma radiation of an energy of 0.66 MeV may be at least 30%. In some embodiments, the total attenuation of transmission of gamma radiation of an energy of 0.66 MeV may be at least 40%. In some embodiments, the total attenuation of transmission of gamma radiation of an energy of 0.66 MeV may be at least 50%. In some embodiments, the total attenuation of transmission of gamma radiation of an energy of 0.66 MeV may be at least 70%. In some embodiments, the total attenuation of transmission of gamma radiation of an energy of 0.66 MeV may be at least 80%. In some embodiments, the total attenuation of transmission of gamma radiation of an energy of 0.66 MeV may be at least 85%.

In some embodiments, the radiation protection device may attenuate transmission of gamma radiation of energy of 0.66 MeV to varying degrees throughout its surface area. In some embodiments the device may attenuate transmission of gamma radiation of an energy of 0.66 MeV by as little as 2% at the least protective point in the device and as much as 90% at the most protective point in the device.

Total attenuation of radiation transmission into a bone marrow is an outcome of the attenuation factor of the radiation protection device in combination with that of the underlying tissue. Total attenuation of radiation transmission may vary. In some embodiments, the total attenuation may be at least 10% of radiation. In some embodiments, the total attenuation may be at least 20% of radiation. In some embodiments, the total attenuation may be at least 50% of radiation. In some embodiments, the total attenuation may be at least 60% of radiation. In some embodiments, the total attenuation may be at least 70% of radiation. In some embodiments, the total attenuation may be at least 80% of radiation. In some embodiments, the total attenuation may be at least 90% of radiation. In some embodiments, the total attenuation may be at least 95% of radiation In some embodiments, the total attenuation may be at least 97% of radiation.

In some embodiments, the device may maintain the viability of at least 60% of the cells in 100 cm$^3$ of active marrow. In another embodiment, the device may maintain the viability of at least 50% of the cells in 120 cm$^3$ of active marrow. In another embodiment, the device may maintain the viability of at least 25% of the cells in 240 cm$^3$ of active marrow. In another the device may maintain the viability of at least 20% of the cells in 300 cm$^3$ of active marrow.

In some embodiments, the device may maintain the viability of at least 60% of the hematopoietic stem cells and progenitors in 100 cm$^3$ of active marrow. In another embodiment, the device may maintain the viability of at least 50% of the hematopoietic stem cells and progenitors in 120 cm$^3$ of active marrow. In another embodiment, the device may maintain the viability of at least 25% of the hematopoietic stem cells and progenitors in 240 cm$^3$ of active marrow. In another the device may maintain the viability of at least 20% of the hematopoietic stem cells and progenitors in 300 cm$^3$ of active marrow.

In some embodiments, the device as described herein may be placed on a body organ to protect it. In another embodiment, the device as described herein may protect a body organ comprising an active bone marrow. In another embodiment, an active bone marrow may comprise red marrow. In another embodiment, an active bone marrow may be found in flat bones. In another embodiment, the device as described may protect a body organ comprising a flat bone. In another embodiment, the device as described herein may protect a hip bone (Os coxae) comprised of the ilium and its crest, ischium and pubis. In another embodiment, the device as described herein may protect the pelvis comprised of the two hip bones, the sacrum and the coccyx. In another embodiment, the device as described herein may protect a breast bone. In another embodiment, the device as described herein may protect the skull. In another embodiment, the device as described herein may protect a skull bone. In another embodiment, the device as described herein may protect a rib or ribs. In another embodiment, the device as described herein may protect a shoulder.

In some embodiments, the device as described herein may protect a femur. In another embodiment, the device as described herein may protect the proximal end of the femur. In another embodiment, the device as described herein may protect the head of the femur and the acetabulum area. In another embodiment, a device protecting a femur may be placed around the thigh in a location which minimizes penetration of radiation to an active bone marrow within the femur. In another embodiment, a device may be placed around the thigh protecting at least the proximal end of the femur. In another embodiment, a device may be placed around the upper arm protecting at least the proximal end of the humerus. In another embodiment, a device protecting a hip bone may be placed around the thigh in a location which minimizes penetration of radiation to an active bone marrow within the hip bone. In another embodiment, a device protecting a femur and a hip bone may be placed around the thigh and hip area in a location which minimizes penetration of radiation to an active bone marrow within the femur and the hip bone. In another embodiment, a device protecting a pelvis may be placed around the hip area in a location which minimizes penetration of radiation to an active bone marrow within the pelvis.

In some embodiments, the device as described herein may protect the hip bones. In another embodiment, the device as described herein may protect the pelvic bones. In another embodiment, the device as described herein may protect the ilium. In another embodiment, the device as described herein may protect the iliac crest. In another embodiment, a device protecting the hip bones may be placed around the waist in a location which minimizes penetration of radiation to an active bone marrow within the hip bones.

In some embodiments, the device as described herein may protect the skull. In another embodiment, the device as described herein protects the cervical vertebrae. In another embodiment, the device as described herein may protect the skull and the cervical vertebrae. In another embodiment, the device as described herein may protect the skull and contains a respirator to allow breathing. In another embodiment, the device as described herein may protect the skull and contains a respirator to allow breathing of clean air. In another embodiment, the device as described herein may protect the skull and contains a respirator capable of filtering out fine particulate matter such that is present in fallout. In another embodiment, a device protecting the skull may contain transparent radiation attenuating material such as leaded glass to allow vision in the form of a visor. In another embodiment, a radiation protection device may be placed around the skull protecting it from radiation while allowing intake of clean air and unhindered vision.

In some embodiments, the radiation protection device may comprise a sleeve structure. In another embodiment, the device comprises a sleeve structure adapted for placement around a circumference of a thigh of a subject. In another embodiment, the device comprises a sleeve structure adapted for placement around a circumference of an upper arm of a subject. In another embodiment, the device comprises a cuff structure. In another embodiment, the device comprises a cuff structure with adjustable shapes for superior fit and performance on contoured adult limbs. In another embodiment, the device provides an excellent fit on a wide range of tapered limb shapes. In another embodiment, the device is a system that protects both thighs, around the groin. In another embodiment, the device is a system that protects both thighs, around the groin and the lower abdomen. In another embodiment, the device is a system that protects the hip-bone as well as the both upper thighs. In another embodiment, the device is a system that protects the hip-bone as well as the both upper thighs and part of the buttocks. In another embodiment, the device is a lower body protector rather than a simple thigh guard. In another embodiment, the device comprises an underwear structure.

In some embodiments, the device may comprise a fastening means for securing the device onto an organ. In another embodiment, the device may comprise a swivel straps. In another embodiment, the device may comprise adjustable swivel straps. In another embodiment, the device may comprise snap-on fastening connectors. In another embodiment, the device may comprise Velcro fastening connectors. In another embodiment, the device may comprise security anchors. In another embodiment, fastening means may be in the form of an elasticised section that fits around a limb or a portion of a limb. In another embodiment, fastening means may include a loop with a hook. In another embodiment, the circumferential stretchability of the device may allow for elasticity but still does not restrict blood flow. In another embodiment, a fabric may provide for added strength thus preventing tearing of the device.

In some embodiments, the device may minimize damages caused by radiation. In another embodiment, the device may minimize damages affecting hematopoiesis caused by radiation. In another embodiment, the device may lower the exposure of cells contained within the bone marrow, to radiation. In another embodiment, the device may lower the subjection of cells contained within the bone marrow to damages affecting hematopoiesis that are caused by radiation. In another embodiment, the device may lower the subjection of cells contained within the bone marrow to no more than 100 rad. In another embodiment, the device may lower the subjection of cells contained within the bone marrow to no more than 200 rad. In another embodiment, the device may lower the subjection of cells contained within the bone marrow to no more than 300 rad.

In some embodiments, the device may secure the viability of cells contained within the bone marrow under radiation conditions of above 300 rad/hour lasting for at least 10 minutes. In another embodiment, the device may secure the viability of cells contained within the bone marrow under radiation conditions of above 500 rad/hour lasting for at least 10 minutes. In another embodiment, the device may secure the viability of cells contained within the bone marrow under radiation conditions of above 700 rad/hour lasting for at least 10 minutes. In another embodiment, the device may secure the viability of cells contained within the bone marrow under radiation conditions of above 1000 rad/hour lasting for at least 10 minutes. In another embodiment, the device may secure the viability of cells contained within the bone marrow under radiation conditions of above 1500 rad/hour lasting for at least 10 minutes. In another embodiment, the device may secure the viability of cells contained within the bone marrow under radiation conditions of above 2000 rad/hour lasting for at least 10 minutes. In another embodiment, the device may secure the viability of cells contained within the bone marrow under radiation conditions of above 2000 rad/hour lasting for at least 20 minutes. In another embodiment, the device may secure the viability of cells contained within the bone marrow under radiation conditions of above 2000 rad/hour lasting for at least 25 minutes.

In some embodiments, the device as described herein may protect cells against radiation damage, reduce radiation damage to cells, promote cell viability under radiation doses of above 4 Gy, or any combination thereof. In some embodiments, the device as described herein may promote the integrity of an active bone marrow under radiation doses of above 4 Gy. In another embodiment, the device as described herein may protect bone marrow cells against radiation damages, reduces radiation damages to bone marrow cells, promotes bone marrow cell viability under radiation doses of above 5 Gy, promotes the integrity of an active bone marrow under radiation doses of above 5 Gy, or any combination thereof.

In some embodiments, bone marrow cells may be fibroblasts, macrophages, adipocytes, osteoblasts, endothelial cells, or mesenchymal stem cells (also called marrow stromal cells). In another embodiment, bone marrow cells may be hematopoietic stem cells, hematopoietic progenitor cells, erythrocytes, macrophages, granulocytes, leukocytes, erythrocytes, thrombocytes, or mesenchymal stem cells.

In some embodiments, a device as described herein may provide protection against a radioactive environment. In another embodiment, a radioactive environment may comprise an environment contaminated with radioisotopes. In another embodiment, a radioactive environment may comprise an environment contaminated with radioactive materials. In another embodiment, a radioactive environment may be an environment exposing a subject to radiation. In another embodiment, a radioactive environment may be an environment exposed to radiation during clinical therapy. In another embodiment, a radioactive environment may be an environment exposed to radiation accidents. In another embodiment, a radioactive environment may be an environment exposed to radiological attacks.

In some embodiments, a radioactive environment may be a nuclear power plant. In another embodiment, a radioactive environment may be a nuclear power plant and its vicinity following a reactor meltdown or accident leading to breach of the reactor containment building. In another embodiment, a radioactive environment may be an environment comprising radioactive chemical elements. In another embodiment, a radioactive environment may be an environment comprising nuclear fuel. In another embodiment, a radioactive environment may be an environment comprising nuclear weapon reprocessing. In another embodiment, a radioactive environment may be an environment comprising a nuclear weapon. In another embodiment, a radioactive environment may be an environment comprising the aftermath of a detonated nuclear weapon. In another embodiment, a radioactive environment may be a nuclear reactor and its vicinity following a reactor meltdown or accident leading to breach of the reactor containment building. In another embodiment, a radioactive environment may be an environment comprising the aftermath of a detonated "dirty bomb". In another embodiment, a radioactive environment may be an environment comprising radioisotopes for medical and/or research purposes. In another embodiment, a radioactive environment may be an environment comprising naturally occurring radioactive materials (NORM) that can be concentrated as a result of the processing or consumption of coal, oil and gas, and some minerals.

In some embodiments, a radioactive environment may contain fission products that emit beta and gamma radiation, and actinides that emit alpha particles, such as uranium-234, neptunium-237, plutonium-238 and americium-241, and even sometimes some neutron emitters such as californium (Cf). In another embodiment, a radioactive environment may comprise uranium. In another embodiment, a radioactive environment may comprise U-235. In another embodiment, a radioactive environment may comprise U-238. In another embodiment, a radioactive environment may comprise alpha-emitting Np-236. In another embodiment, a radioactive environment may comprise Am-241. In another embodiment, a radioactive environment may comprise alpha, beta, neutron and/or gamma emitters. In another embodiment, a radioactive environment may comprise technetium-99m. In another embodiment, a radioactive environment may comprise Y-90. In another embodiment, a radioactive environment may comprise I-131. In another embodiment, a radioactive environment may comprise Sr-89. In another embodiment, a radioactive environment may comprise Ir-192. In another embodiment, a radioactive environment may comprise Co-60. In another embodiment, a radioactive environment may comprise Cs-137. In another embodiment, a radioactive environment may comprise Au-198. In another embodiment, a radioactive environment may comprise Cf-252. In another embodiment, a radioactive environment may comprise Cm-244. In another embodiment, a radioactive environment may comprise Gd-153. In another embodiment, a radioactive environment comprises Ge-68. In another embodiment, a radioactive environment may comprise H-3. In another embodiment, a radioactive environment may comprise I-125. In another embodiment, a radioactive environment may comprise Kr-85. In another embodiment, a radioactive environment may comprise Strontium-90.

In some embodiments, a radioactive environment may comprise a Radioisotopic thermoelectric generator (RTG). In another embodiment, a radioactive environment may comprise a ruptured Radioisotopic thermoelectric generator (RTG). In another embodiment, a radioactive environment may comprise an irradiator. In another embodiment, a radioactive environment may comprise a ruptured irradiator. In another embodiment, a radioactive environment may comprise a multi-beam teletherapy (gamma knife). In another embodiment, a radioactive environment may comprise a nuclear reactor. In another embodiment, a radioactive environment may comprise a centrifuge comprising a radioactive material. In another embodiment, a radioactive environment may comprise a centrifuge comprising an isotopic generator. In another embodiment, a radioactive environment may comprise a nuclear energy production facility. In another embodiment, a radioactive environment may comprise a breached nuclear energy production facility. In another embodiment, a radioactive environment may comprise a medical facility comprising a diagnostic radiology facility, nuclear medicine, and/or radiotherapy. In another embodiment, a radioactive environment may comprise facilities using a nuclear food irradiation technique. In another embodiment, a radioactive environment has a surface dose rate greater than 200 mrem per hour (2 mSv/h).

In some embodiments, the device as described herein may prevent diseases induced by radiation. In another embodiment, the device as described herein may reduce the risk of acquiring a disease induced by radiation. In another embodiment, the device as described herein may reduce the risk of acquiring a bone marrow disease induced by radiation. In another embodiment, the device as described herein may reduce the risk of acquiring a bone marrow disease as described hereinbelow. In another embodiment, the device as described herein may prevent bone marrow diseases that are induced by radiation. In another embodiment, the device as described herein may prevent acute radiation syndrome. In another embodiment, the device as described herein may attenuate acute radiation syndrome. In another embodiment, the device as described herein may prevent displaced bone marrow architecture. In another embodiment, the device as described herein may reduce the likelihood of malignancies. In another embodiment, the device as described herein may reduce the likelihood cancers of the hematologic progenitor cells. In another embodiment, the device as described herein may reduce the likelihood leukemias. In another embodiment, the device as described herein may reduce the likelihood depressed immune system. In another embodiment, the device as described herein may prevent radiation sickness.

In some embodiments, the device may comprise a sealable opening or openings allowing for the intraosseous injection of substances into the underlying bones shielded by the device described herein. In another embodiment, the device may comprise a sealable opening or openings allowing for the introsseous injection of chemical agents into the underlying bones shielded by the device described herein. In another embodiment, the device may comprise a sealable opening or openings allowing for the introsseous injection of drugs into the underlying bones shielded by the device described herein. In another embodiment, the device may comprise a sealable opening allowing for the introsseous injection of bioactive agents into the underlying bones shielded by the device described herein. In another embodiment, the sealable opening or openings described herein may comprise a seal made of radiation attenuating material that when opened allows access to an underlying aperture.

In some embodiments, the radiation protection device described herein may comprise a component for real-time measurement of radiation attached to an external surface of the device. In another embodiment, the device may comprise a component for real-time measurement of radiation attached to an internal surface of the device. In another embodiment, the device may comprise a component for real-time measurement of radiation attached to an external surface of the device and to an internal surface of the device. In another embodiment, the device may comprise a dosimeter attached to an external surface of the device. In another embodiment, the device may comprise a dosimeter attached to an internal surface of the device. In another embodiment, the device may comprise a dosimeter attached to an external surface of the device and to an internal surface of the device.

In some embodiments, the device may comprise a dosimeter placed on an internal surface of the device (i.e facing the protected body part) for the estimation of the actual cumulative radiation dose received in a protected marrow.

In some embodiments, the dosimeter may be an electronic dosimeter. In another embodiment, the dosimeter may be a film dosimeter. In another embodiment, the dosimeter may be a Thermoluminescent Dosimeter (TLD). In another embodiment, a component for real-time measurement of radiation may be a Geiger counter. In another embodiment, a component for real-time measurement of radiation may be a scintillation counter.

In some embodiments, the radiation protection device may include a layer which is resistant to projectile penetration (e.g. bullet proof). In another embodiment, the device may be fire resistant and protects a user against radiation. In another embodiment, the device may be fire retardant and protects a user against radiation. In another embodiment, fire resistant or retardant materials that can be used with the present device are known to one of average skill in the art. In another embodiment, the device may protect a user against both radiation and fire hazards.

In some embodiments, the device may be waterproof and protects a user against radiation. In another embodiment, waterproof materials that can be used with the present device are known to one of average skill in the art. In another embodiment, the device may be organic solvent proof and protects a user against radiation. In another embodiment, organic solvent proof materials that can be used with the present device are known to one of average skill in the art.

In some embodiments, the radiation protection device may be used to increase survival chances of a subject facing exposure to gamma radiation emanating from radioisotopes present in the aftermath of a nuclear reactor meltdown. In another embodiment, the device as described herein may be used to increase survival chances of a subject facing exposure to gamma radiation emanating from radioisotopes present in the aftermath of a nuclear bomb explosion. In another embodiment, the device as described herein may be used to increase survival chances of a subject facing exposure to gamma radiation emanating from radioisotopes present in the aftermath of a radiological weapon explosion.

In some embodiments, the radiation protection device may be used to increase the time a subject may be present in the aftermath of a nuclear reactor meltdown without receiving a lethal radiation dose. In another embodiment, the device as described herein may be used to increase the time a subject may be present in the aftermath of a nuclear bomb explosion without receiving a lethal radiation dose. In another embodiment, the device as described herein may be used to increase the time a subject may be present in the aftermath of a radiological weapon explosion without receiving a lethal radiation dose.

In some embodiments, the radiation protection device may be used to reduce the radiation dose received in an active marrow from gamma radiation emanating from radioisotopes present in the aftermath of a nuclear reactor meltdown, a radiological weapon explosion or a nuclear bomb explosion by at least 10%. In another embodiment, the device as described herein may be used to reduce the radiation dose received in an active marrow from gamma radiation emanating from radioisotopes present in the aftermath of a nuclear reactor meltdown, radiological weapon explosion or a nuclear bomb explosion by at least 20%. In another embodiment, the device as described herein may be used to reduce the radiation dose received in an active marrow from gamma radiation emanating from radioisotopes present in the aftermath of a nuclear reactor meltdown, a radiological weapon explosion or a nuclear bomb explosion by at least 30%. In another embodiment, the device as described herein may be used to reduce the radiation dose received in an active marrow from gamma radiation emanating from radioisotopes present in the aftermath of a nuclear reactor meltdown, a radiological weapon explosion or a nuclear explosion by at least 40%. In another embodiment, the device as described herein may be used to reduce the radiation dose received in an active marrow from gamma radiation emanating from radioisotopes present in the aftermath of a nuclear reactor meltdown, a radiological weapon explosion or a nuclear bomb explosion by at least 50%. In another embodiment, the device as described herein may be used to reduce the radiation dose received in an active marrow from gamma radiation emanating from radioisotopes present in the aftermath of a nuclear reactor meltdown, radiological weapon explosion or a nuclear bomb explosion by at least 60%. In another embodiment, the device as described herein may be used to reduce the radiation dose received in an active marrow from gamma radiation emanating from radioisotopes present in the aftermath of a nuclear reactor meltdown, radiological weapon explosion or a nuclear bomb explosion by at least 70%.

In some embodiments, the radiation protection device may weigh no more than 5 Kg. In another embodiment, the device as described herein may weigh no more than 6 Kg. In another embodiment, the device as described herein may weigh no more than 7 Kg. In another embodiment, the device as described herein may weigh no more than 8 Kg. In another embodiment, the device as described herein may weigh no more than 9 Kg. In another embodiment, the device as described herein may weigh no more than 10 Kg. In another embodiment, the device as described herein may weigh no more than 11 Kg. In another embodiment, the device as described herein may weigh no more than 12 Kg. In another embodiment, the device as described herein may weigh no more than 13 Kg. In another embodiment, the device as described herein may weigh no more than 14 Kg. In another embodiment, the device as described herein may weigh no more than 15 Kg. In another embodiment, the device as described herein may weigh no more than 16 Kg. In another embodiment, the device as described herein may weigh no more than 17 Kg. In another embodiment, the device as described herein may weigh no more than 18 Kg. In another embodiment, the device as described herein may weigh no more than 19 Kg. In another embodiment, the device as described herein may weigh no more than 20 Kg.

In some embodiments, the device as described herein may have a distribution of radiation attenuating material so as to be comprised of no more than 5 mm solid lead equivalent at its least protective point. In another embodiment, the device as described herein may have a distribution of radiation attenuating material so as to be comprised of no more than 4 mm solid lead equivalent at its least protective point. In another embodiment, the device as described herein may have a distribution of radiation attenuating material so as to be comprised of no more than 3 mm solid lead equivalent at its least protective point. In another embodiment, the device as described herein may have a distribution of radiation attenuating material so as to be comprised of no more than 2 mm solid lead equivalent at its least protective point. In another embodiment, the device as described herein may have a distribution of radiation attenuating material so as to be comprised of no more than 1 mm solid lead equivalent at its least protective point. In another embodiment, the device as described herein may have a distribution of radiation attenuating material so as to be comprised of no more than 0.1 mm solid lead equivalent at its least protective point.

In some embodiments, the device as described herein may have a distribution of radiation attenuating material so as to be comprised of no less than 6 mm solid lead equivalent at its most protective point. In some embodiments, the device as described herein may have a distribution of radiation attenuating material so as to be comprised of no less than 7 mm solid lead equivalent at its most protective point. In some embodiments, the device as described herein may have a distribution of radiation attenuating material so as to be comprised of no less than 8 mm solid lead equivalent at its most protective point. In some embodiments, the device as described herein may have a distribution of radiation attenuating material so as to be comprised of no less than 9 mm solid lead equivalent at its most protective point. In another embodiment, the device as described herein may have a distribution of radiation attenuating material so as to be comprised of no less than 10 mm solid lead equivalent at its most protective point. In another embodiment, the device as described herein may have a distribution of radiation attenuating material so as to be comprised of no less than 11 mm solid lead equivalent at its most protective point. In another embodiment, the device as described herein may have a distribution of radiation attenuating material so as to be comprised of no less than 12 mm solid lead equivalent at its most protective point. In another embodiment, the device as described herein may have a distribution of radiation attenuating material so as to be comprised of no less than 13 mm solid lead equivalent at its most protective point. In another embodiment, the device as described herein may have a distribution of radiation attenuating material so as to be comprised of no less than 14 mm solid lead equivalent at its most protective point. In another embodiment, the device as described herein may have a distribution of radiation attenuating material so as to be comprised of no less than 15 mm solid lead equivalent at its most protective point. In another embodiment, the device as described herein may have a distribution of radiation attenuating material so as to be comprised of no less than 16 mm solid lead equivalent at its most protective point. In another embodiment, the device as described herein may have a distribution of radiation attenuating material so as to be comprised of no less than 17 mm solid lead equivalent at its most protective point. In another embodiment, the device as described herein may have a distribution of radiation attenuating material so as to be comprised of no less than 18 mm solid lead equivalent at its most protective point. In another embodiment, the device as described herein may have a distribution of radiation attenuating material so as to be comprised of no less than 19 mm solid lead equivalent at its most protective point. In another embodiment, the device as described herein may have a distribution of radiation attenuating material so as to be comprised of no less than 20 mm solid lead equivalent at its most protective point. In another embodiment, the device as described herein may have a distribution of radiation attenuating material so as to be comprised of no less than 21 mm solid lead equivalent at its most protective point. In another embodiment, the device as described herein may have a distribution of radiation attenuating material so as to be comprised of no less than 22 mm solid lead equivalent at its most protective point. In another embodiment, the device as described herein may have a distribution of radiation attenuating material so as to be comprised of no less than 23 mm solid lead equivalent at its most protective point. In another embodiment, the device as described herein may have a distribution of radiation attenuating material so as to be comprised of no less than 24 mm solid lead equivalent at its most protective point.

In Another embodiment, the device as described herein does not limit the movement of the wearers limbs.

Figure 8:
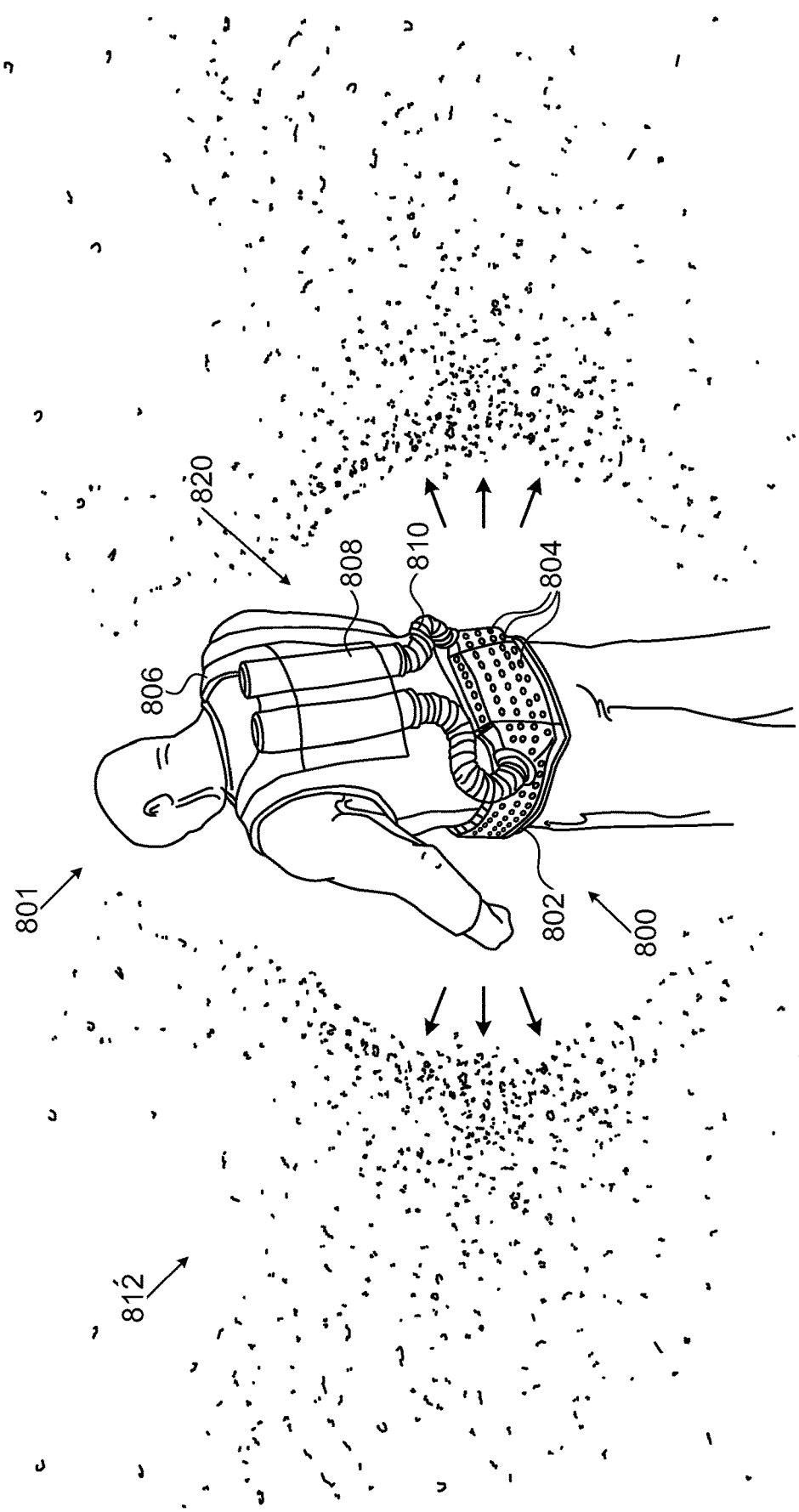
FIG. 8 illustrates a radiation protection device with a blower for dispersal of radioactive particles in accordance with an embodiment of the present invention.

FIG. 8 illustrates a radiation protection device 800 with fallout dispersal ability in accordance with an embodiment of the present invention. Radiation protection device 800 may include a vest 806 for supporting a radiation attenuating component, for example in the form of a belt 802 around the waist. The radiation attenuation component inside belt 802 may be removed or attached according to need. The belt 802 may include a blower 820. Blower 820 may include a manifold (not shown in this figure) connected to balloons of compressed gas 808 (e.g. air) supported on vest 806 so that the compressed air may be released from the balloons through pipes 810 and through the manifold and exit through nozzles 804. Nozzles 804 may be located on the belt. When operating the device, the compressed gas is forced through the nozzles and radioactive particles, such as, for example, nuclear fallout 812 may be blown away from the waist of the user 801 who wears and uses the radiation protection device, thus greatly reducing the dose rate absorbed in the active bone marrow located in the pelvis of the user.

In some embodiments, the radiation protection device 800 would not include both a radiation attenuating component and the blower 820.

In some embodiments, the radiation protection device comprising a blower as described herein may blow away at least 50% of radioactive particles from a protected active marrow to a distance of no less than 10 cm. In another embodiment, the radiation protection device comprising a blower as described herein may blow away at least 50% of radioactive particles from a protected active marrow by no less than 20 cm. In another embodiment, the radiation protection device comprising a blower as described herein may blow away at least 50% of radioactive particles from a protected active marrow by no less than 30 cm. In another embodiment, the radiation protection device comprising a blower as described herein may blow away at least 50% of radioactive particles from a protected active marrow by no less than 40 cm. In another embodiment, the radiation protection device comprising a blower as described herein may blow away at least 50% of radioactive particles from a protected active marrow by no less than 50 cm. In another embodiment, the radiation protection device comprising a blower as described herein may blow away at least 50% of radioactive particles from a protected active marrow by no less than 60 cm. In another embodiment, the radiation protection device comprising a blower as described herein may blow away at least 50% of radioactive particles from a protected active marrow by no less than 70 cm. In another embodiment, the radiation protection device comprising a blower as described herein may blow away at least 50% of radioactive particles from a protected active marrow by no less than 80 cm. In another embodiment, the radiation protection device comprising a blower as described herein may blow away at least 50% of radioactive particles from a protected active marrow by no less than 90 cm. In another embodiment, the radiation protection device comprising a blower as described herein may blow away at least 50% of radioactive particles from a protected active marrow by no less than 100 cm. In another embodiment, the radiation protection device comprising a blower as described herein may blow away at least 50% of radioactive particles from a protected active marrow by no less than 110 cm. In another embodiment, the radiation protection device comprising a blower as described herein may blow away at least 50% of radioactive particles from a protected active marrow by no less than 120 cm. In another embodiment, the radiation protection device comprising a blower as described herein may blow away at least 50% of radioactive particles from a protected active marrow by no less than 130 cm. In another embodiment, the radiation protection device comprising a blower as described herein may blow away at least 50% of radioactive particles from a protected active marrow by no less than 140 cm. In another embodiment, the radiation protection device comprising a blower as described herein may blow away at least 50% of radioactive particles from a protected active marrow by no less than 150 cm. In another embodiment, the radiation protection device comprising a blower as described herein may blow away at least 50% of radioactive particles from a protected active marrow by no less than 160 cm. In another embodiment, the radiation protection device comprising a blower as described herein may blow away at least 50% of radioactive particles from a protected active marrow by no less than 170 cm. In another embodiment, the radiation protection device comprising a blower as described herein may blow away at least 50% of radioactive particles from a protected active marrow by no less than 180 cm. In another embodiment, the radiation protection device comprising a blower as described herein may blow away at least 50% of radioactive particles from a protected active marrow by no less than 190 cm. In another embodiment, the radiation protection device comprising a blower as described herein may blow away at least 50% of radioactive particles from a protected active marrow by no less than 200 cm.

Furthermore, in accordance with some embodiments, the blower may blow radioactive particles to a varying distance across the radiation protection device, the distance being inversely related to radiation attenuation levels of tissue present between a given point of the radiation protection device and the active bone marrow.

Furthermore, in accordance with some embodiments, the varying distances to which the blower blows away radioactive particles are determined by the formula $$D_R(x, y, z) = \sqrt{\frac{A_D}{A_T}},$$

where $D_R$ is a required fold increase in radioactive particle distance from point x,y,z on the radiation protection device, $A_D$ is a radiation attenuation level needed to reduce the radiation dose absorbed in the active bone marrow contained within the body part to a desired level, and $A_T$ is the tissue radiation attenuation level between the point x,y,z and the active bone marrow contained in the body part.

Furthermore, in accordance with some embodiments, the radiation protection device comprising a blower may be configured to provide a substantially uniform radiation protection to the active marrow. Furthermore, in accordance with some embodiments, the radiation protection device comprising a blower may incorporate also a radiation attenuation component. Furthermore, in accordance with some embodiments, the radiation protection device comprising a blower may incorporate also a radiation attenuation component which is removable. Furthermore, in accordance with some embodiments, the radiation protection device comprising a blower may serve also as a supporting harness or part of a supporting harness for a self-contained breathing apparatus. Furthermore, in accordance with some embodiments, the radiation protection device comprising a blower may draw the pressurized gas needed for dispersal of fallout from the gas canister or canisters feeding a self-contained breathing apparatus.

Figure 9:
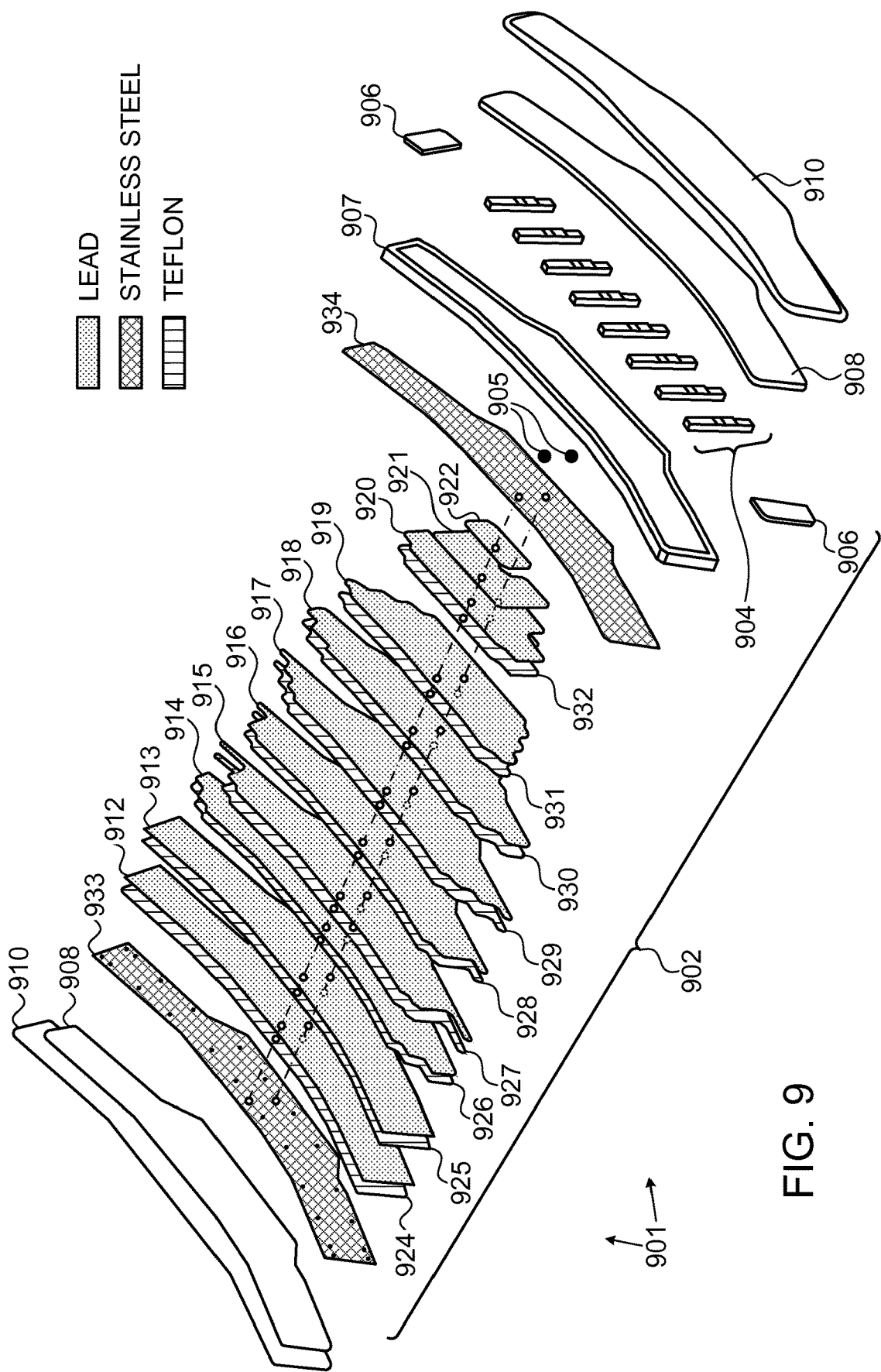
FIG. 9 illustrates an exploded view of a radiation protection device embodied as a belt and containing a core assembly including a layer assembly of a radiation attenuating component as shown in FIG. 7A, friction-minimizing dividers, supporting structure, fastening bands, rigid pockets. The core assembly is covered in sealing pouch and composite fabric.

FIG. 9 illustrates an exploded view of a radiation protection device embodied as belt 901. The belt is comprised of a core assembly 902, fastening bands 904, rigid pockets 906, sealing pouch 908 and composite fabric encasing 910. Core assembly 902 is comprised of a radiation attenuating component in the form of 11 uniquely shaped layers of radiation attenuating material 912-922 (1 mm virgin lead in this example) which when compiled form a distribution of radiation attenuating material inversely correlated to the thickness or/and the radiodensity of the tissue interposed between the radiation protection device and the protected active marrow. While the distribution of radiation attenuating material may be similar to layer assembly 700 (see FIG. 7), dividers of friction-minimizing 924-932 (0.1 mm Teflon in this example) are placed between layers 912-920 to minimize friction between layers and allow relative movement of layers upon wrapping and unwrapping the radiation protection device from around a body part containing active marrow. A supporting frame, comprised of layers 933-934 (in one example, layers 933-934 may be made of 0.4 mm stainless steel), forms the frame portion of core assembly 902. This frame provides mechanical protection to any malleable radiation attenuating material and confers elasticity upon the radiation protection device. Fastening bands 904 together with rivets 905 keep all core assembly components together while allowing layer sliding upon wrapping and unwrapping. Rigid pockets 906 cover the extremities of the core assembly 902 and provide both rigidity to core assembly extremities and also blunt core assembly sharpness which may be destructive. Elastomer 907 (in one example, EPDM) lines the lower and upper edges of core assembly 902 for shock and impact absorbance. Sealing pouch 908 envelopes all components of core assembly 902. Sealing pouch 908 may be water resistant and may be comprised of polymers, silicon or fabric. Core assembly 902 together with sealing pouch 908 is inserted into composite fabric encasing 910. Composite fabric encasing 910 is preferably fire retardant or fire resistant.

Figure 10A:
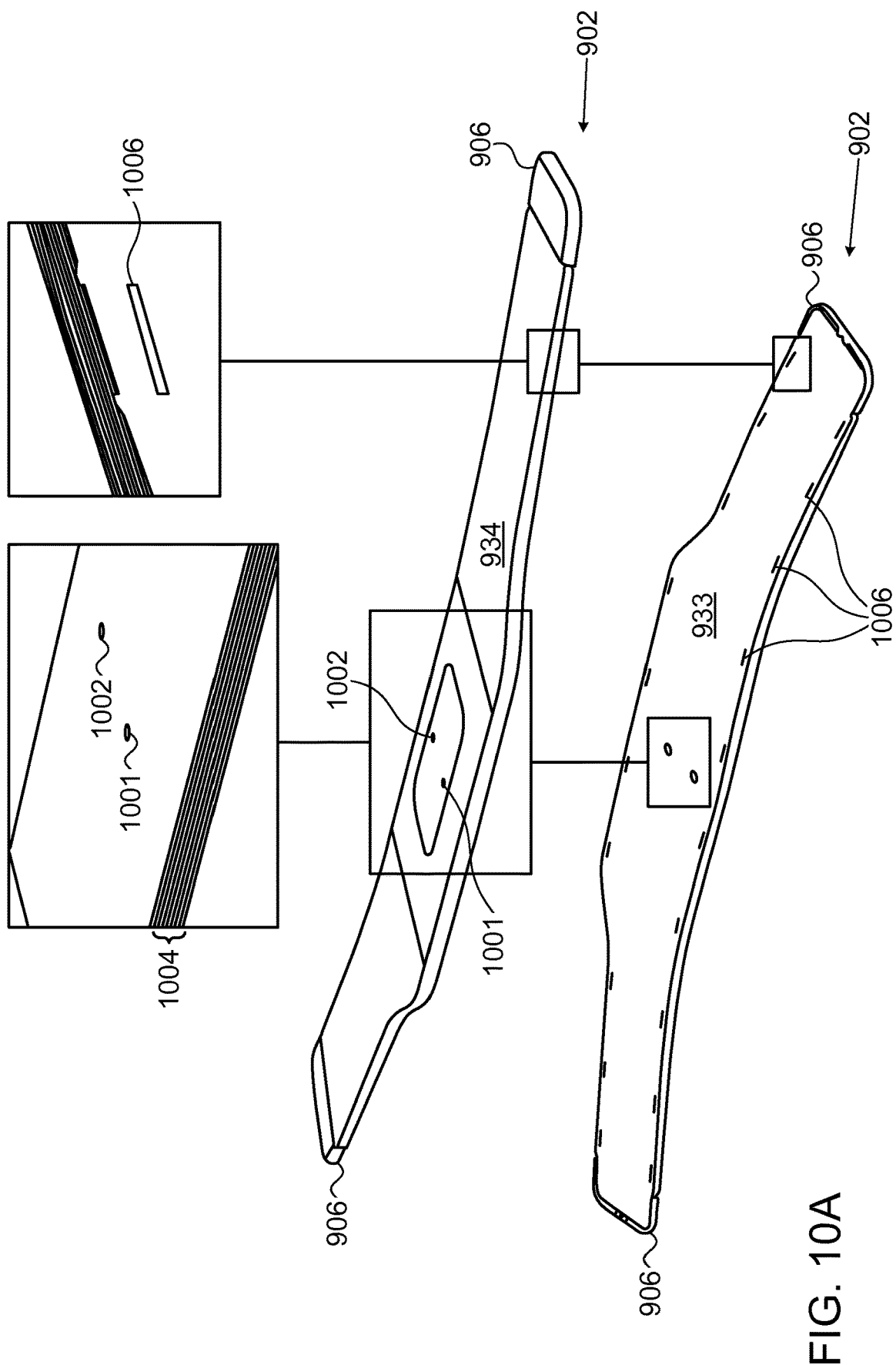
FIG. 10A illustrates how the core assembly of the radiation protection device embodied as a belt as shown in FIG. 9 is held together.

In FIG. 10A, a non-exploded view of core assembly 902 is shown. FIG. 10A illustrates how core assembly 902 of the radiation protection device embodied as a belt is held together. A supporting frame, comprised of layers 933-934 (in one example, layers 933-934 are made from 0.4 mm stainless steel), forms the frame portion of the core assembly 902. This supporting frame provides mechanical protection to any malleable radiation attenuating material and confers elasticity upon the radiation protection device. Fastening bands 904 together with rivets 905 (see FIG. 9) keep all core components together while allowing layer sliding upon wrapping and unwrapping. Rivet holes 1001, 1002 run through layers 933-934 and through the entire radiation attenuating component 1004 which includes layers of radiation attenuating material 912-922 (see FIG. 9) and dividers of friction-minimizing material 924-932 (see FIG. 9). Slots 1006 are present at regular intervals throughout supporting frame layer 933 and allow for the insertion of fastening bands. Slots 1006 may be present in either of layers 933 or 934. Rigid pockets 906 cover the extremities of the core structure 902 and provide both rigidity to core assembly extremities and also blunt core assembly sharpness which may be destructive.

Figure 10B:
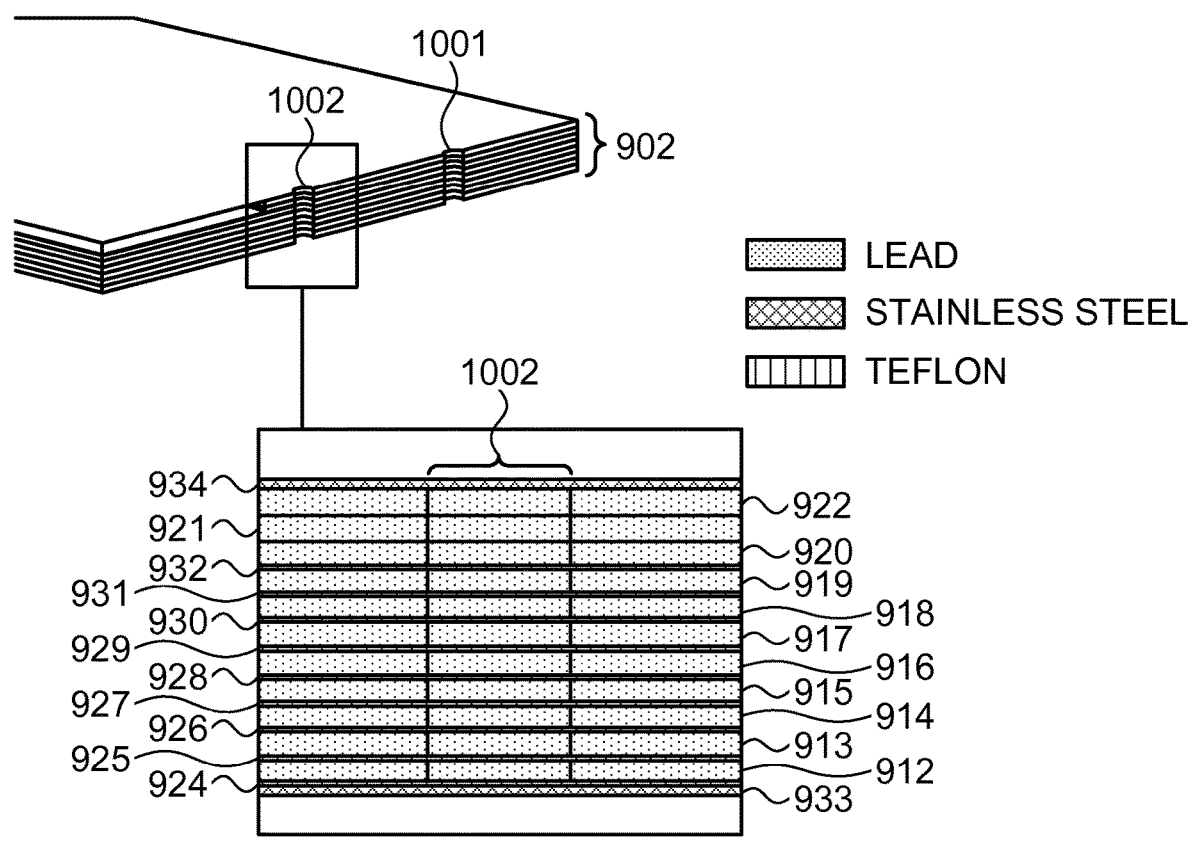
FIG. 10B illustrates the different layers of the core assembly of the radiation protection device embodied as a belt as shown in FIG. 9

In FIG. 10B a cross section of core assembly 902 is shown. Section is through rivet holes 1001, 1002 and shows the different layers comprising core assembly 902. From top to bottom the order of layers is as follows: 1) Supporting frame layer 934; 2) Radiation attenuating material layer 922; 3) Radiation attenuating material layer 921; 4) Radiation attenuating material layer 920; 5) Friction-minimizing divider 932; 6) Radiation attenuating material layer 919; 7) Friction-minimizing divider 931; 8) Radiation attenuating material layer 918; 9) Friction-minimizing divider 930; 10) Radiation attenuating material layer 917; 11) Friction-minimizing divider 929; 12) Radiation attenuating material layer 916; 13) Friction-minimizing divider 928; 14) Radiation attenuating material layer 915; 15) Friction-minimizing divider 927; 16) Radiation attenuating material layer 914; 17) Friction-minimizing divider 926; 18) Radiation attenuating material layer 913; 19) Friction-minimizing divider 925; 20) Radiation attenuating material layer 912; 21) Friction-minimizing divider 924; 22) Supporting frame layer 933.

Figure 11:
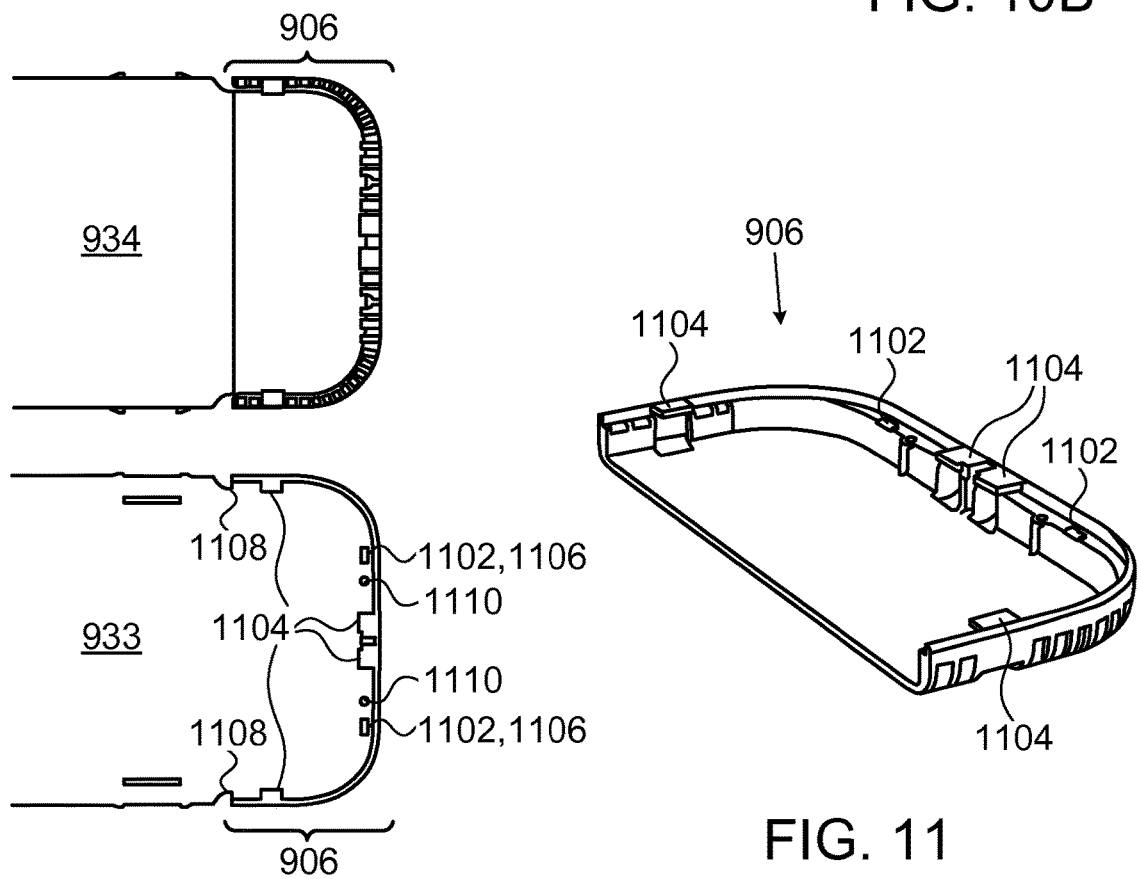
FIG. 11 illustrates the rigid pockets which are placed on the two extremities of the core assembly of the radiation protection device embodied as a belt as shown in FIG. 9

FIG. 11 shows rigid pocket structure and connection mechanism. Rigid pockets 906 cover the extremities of the core assembly 902 (see FIG. 9) and provide both rigidity to core assembly extremities and also blunt core assembly sharpness which may be destructive. Rigid pockets 906 may be manufactured by injection molding of polymers such as nylon and reinforced by glass fiber. Reinforced elastomers, thermoplastic and thermosetting plastic may be used. Rigid pockets 906 attach via snaps 1102 and fixation points 1104 to supporting frame layer 933 via holes 1106 and grooves 1108, respectively. Rigid pockets 906 may be further attached to supporting frame layer 933 with screws via holes 1110. By attaching only to supporting frame layer 933, which is the inner-most layer closest to the protected subject, rigid pockets 906 allow the relative movement of more exterior core assembly layers when wrapping and unwrapping of belt 901. When wrapped around the subject, outer layers of core assembly 902 retreat backwards in the volume formed by the rigid pocket. When unwrapped and flattened outer layers of core assembly 902 move forward in the volume formed by the rigid pocket, approaching the position of the innermost layers.

Figure 12A:
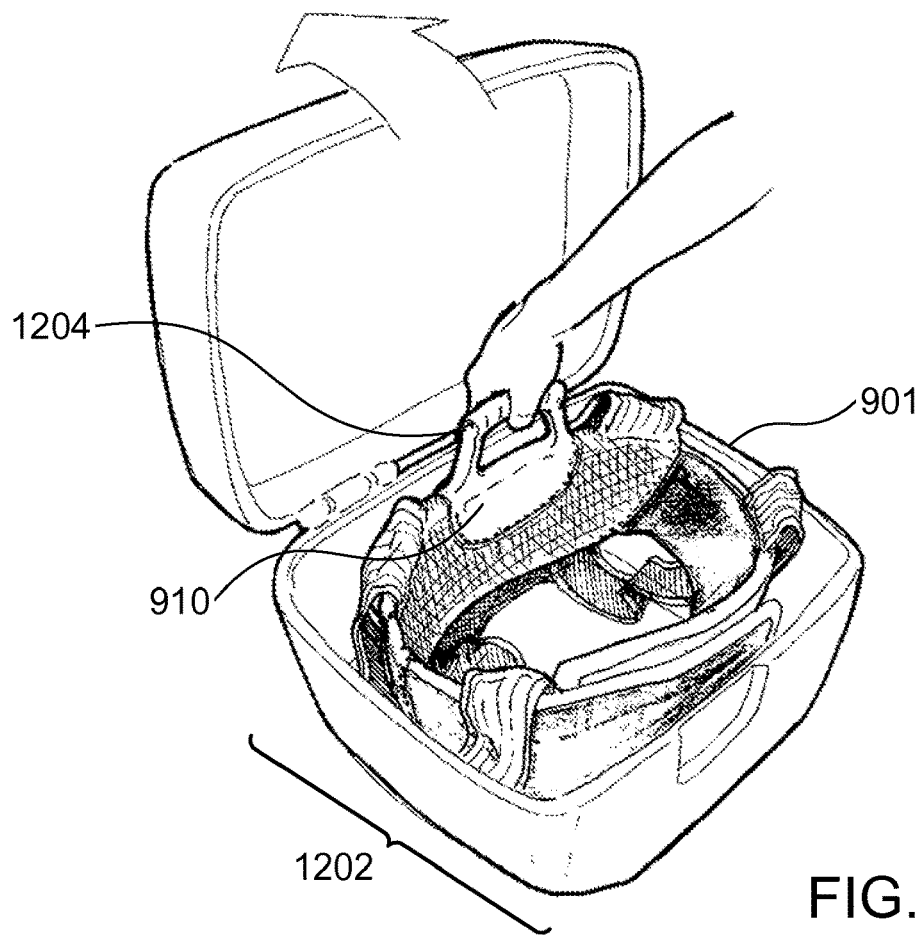
FIG. 12A illustrates removal of the radiation protection device, embodied as a belt as shown in FIG. 9, from storage by use of the carrying handle.

FIG. 12A shows a radiation protection device embodied as belt 901 in a stored position. Belt 901 is stored in portable case 1202 and is removed from storage by grasping carrying handle 1204. Carrying handle 1204 is connected to or is an integral part of composite fabric encasing 910.

Figure 12B:
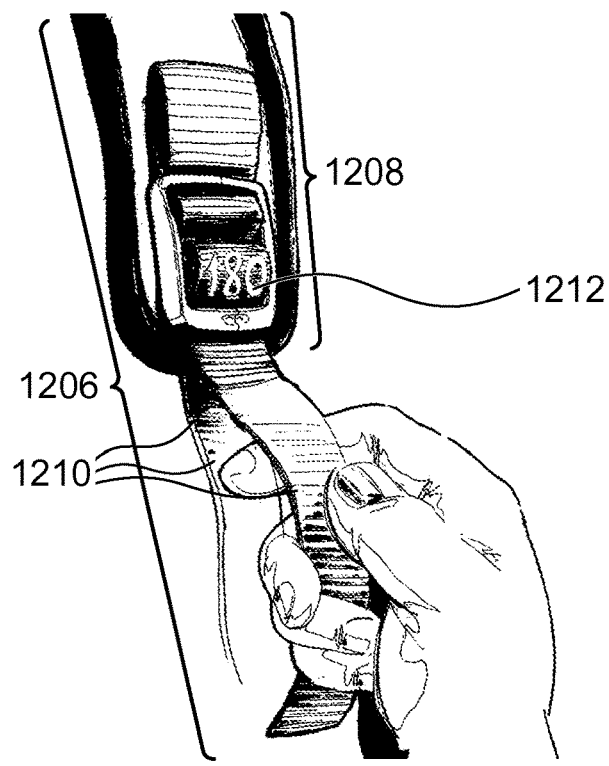
FIG. 12B illustrates use of the height selection system as described herein for proper placement of a radiation protection device as shown in FIG. 9.

In FIG. 12B suspender strap 1206 is shown. Suspender strap 1206 is connected to belt 901 (see FIG. 9), providing weight support. Suspender strap 1206 also determines the height of the belt around the subject's torso. Suspender strap 1206 contains a padded section 1208 which is placed over the subject's shoulder. Suspender strap 1206 contains a non-padded strap 1210 which connects to belt 901 and affects its height in relation to the subject's torso. The subject may adjust the height of belt 901 by pulling on strap 1210 until subject's height (in this example 180 cm) appears in ladder lock 1212. Once subject's height appears in ladder lock this is an indication that belt 901 is at the correct torso height for optimal bone marrow protection.

Figure 12C:
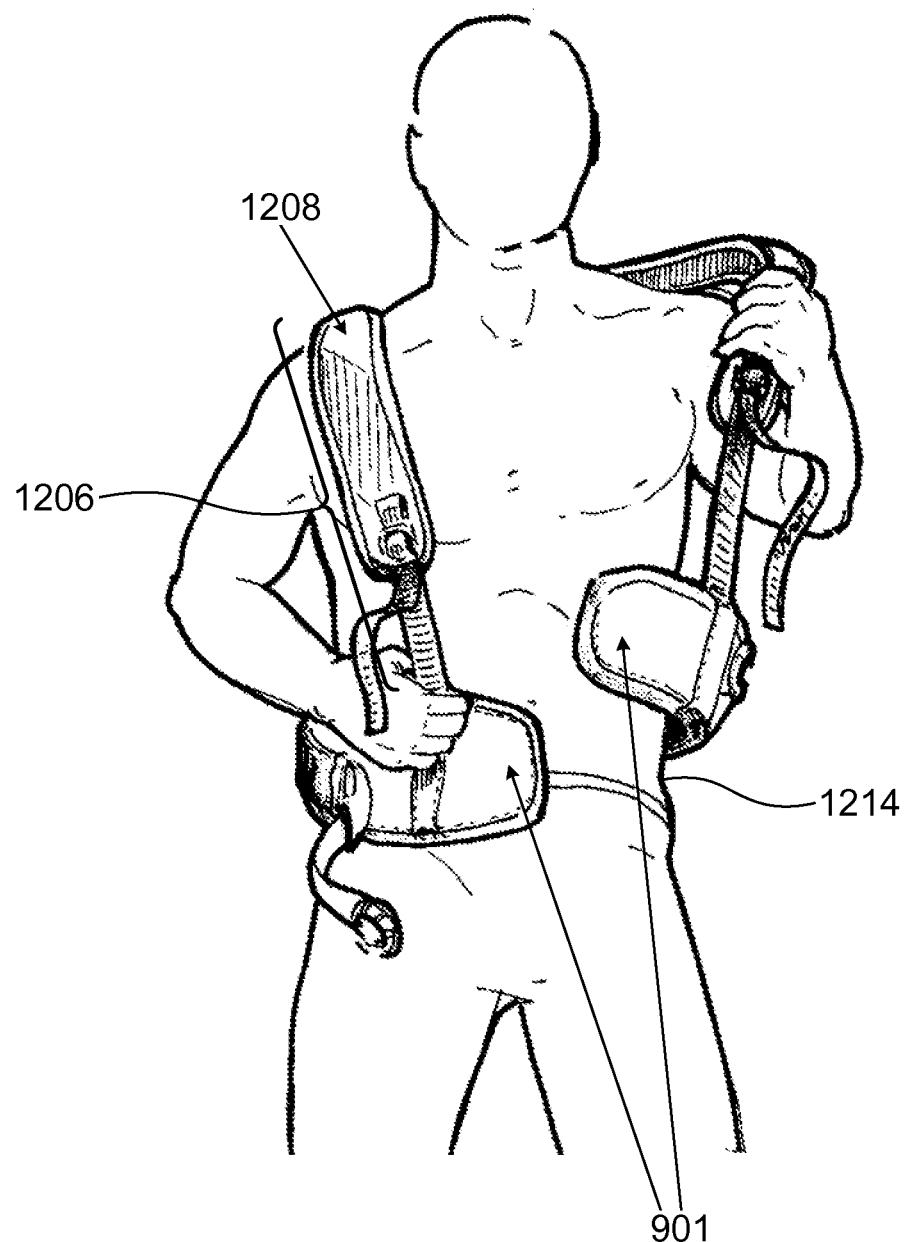
FIG. 12C illustrates wearing of a radiation protection device as shown in FIG. 9 by use of suspenders.
Figure 12D:
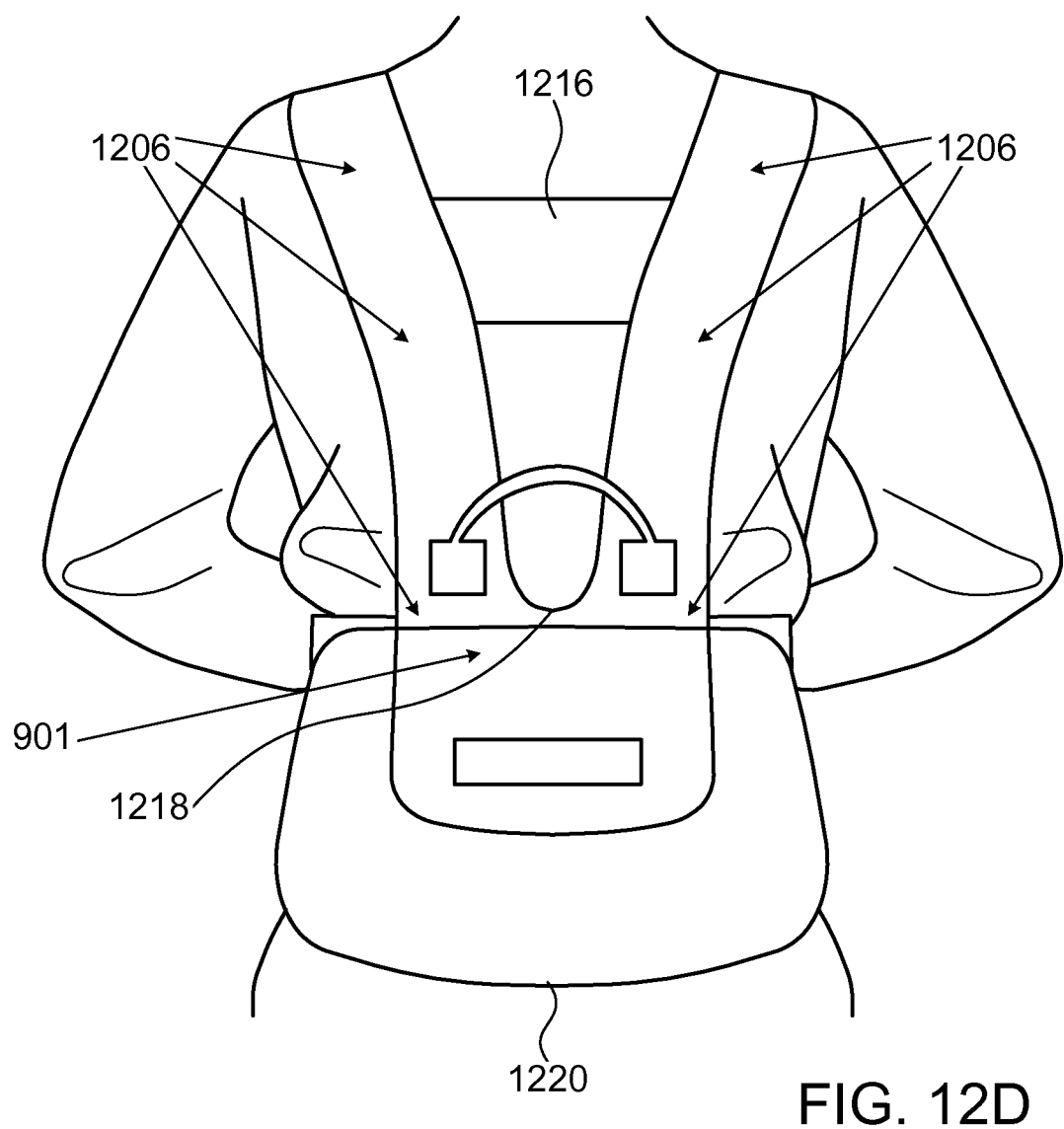
FIG. 12D illustrates a rear view of a radiation protection device as shown in FIG. 9 and worn by a subject.

In FIG. 12C placement of belt 901 on the subject's anterior torso is demonstrated. Padded section 1208 of suspender strap 1206 is placed on subject's shoulder before or after height adjustment as in FIG. 12B is performed. Suspender strap 1206 is connected to belt 901 providing weight support. Once belt is wrapped around subject's hip 1214, belt fastening as in FIGS. 13A and 13B may take place In FIG. 12D, correct placement of belt 901 on subject's dorsal torso is demonstrated. Suspender straps 1206 are interconnected by bridge 1216 to improve stability. Belt is placed at correct torso height so that it is in between the fourth lumbar vertebra 1218 and the lower sacrum 1220.

Figure 13A:
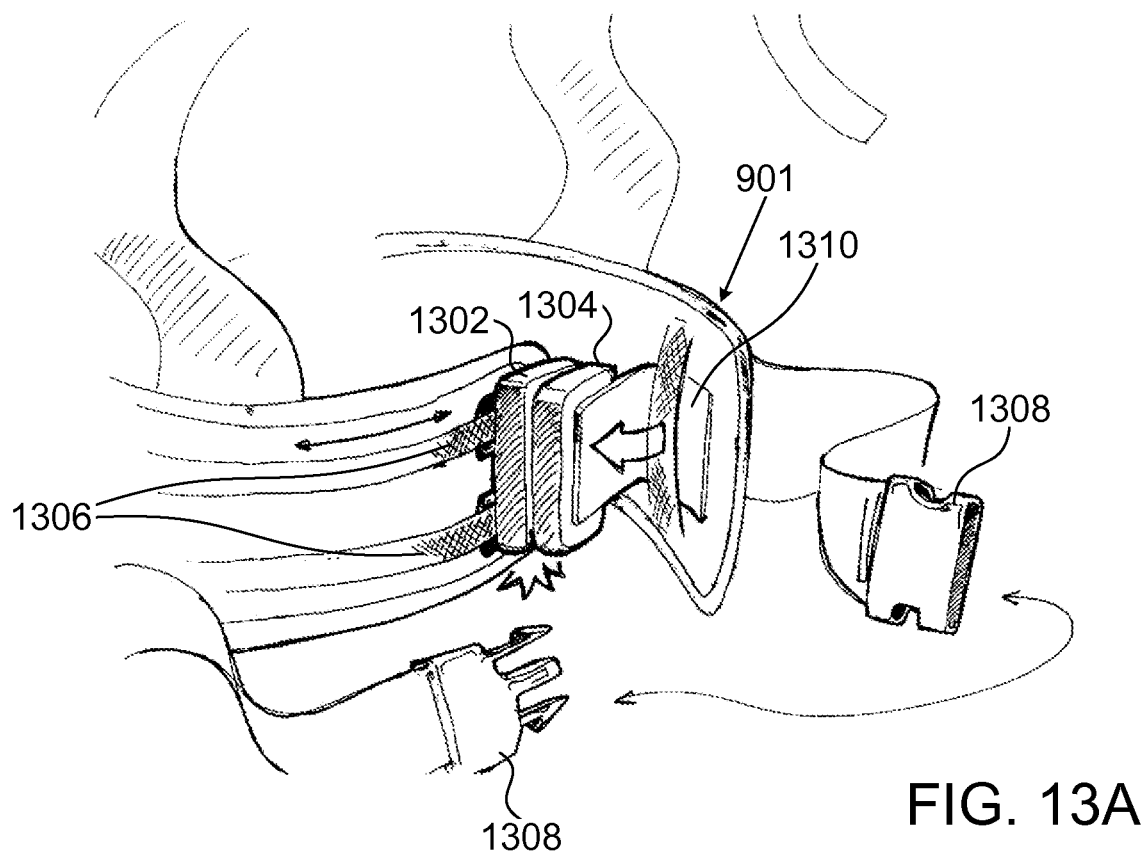
FIG. 13A illustrates the fastening mechanism of a radiation protection device as shown in FIG. 9 by use of magnetic closure coupled with buckling.
Figure 13B:
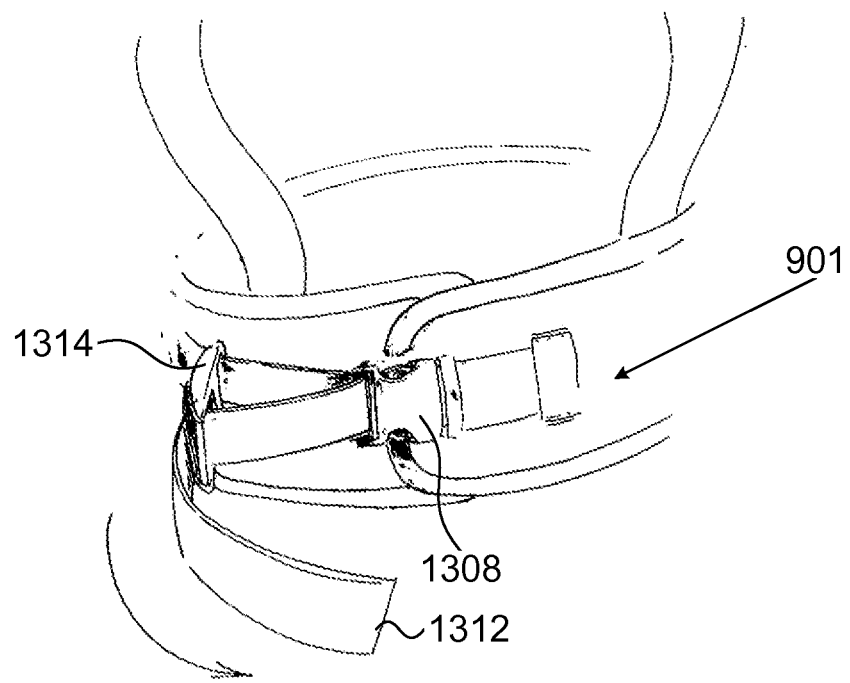
FIG. 13B illustrates tightening of a fastened a radiation protection device as shown in FIG. 9 by use of magnetic closure coupled with buckling.

FIG. 13A shows the first step of the fastening mechanism of belt 901. In the first step, magnetic attraction between magnet 1302 and magnetic material 1304 aids the subject in wrapping belt 901 around torso. Magnet 1302 is connected to tracks 1306 on one end of belt 901, which allow it to slide together with magnetic material 1304 when subject fastens buckle 1308 and tightens belt 901 using force multiplier as shown in FIG. 13B. Magnetic material 1304 is fixed via flexible flap 1310 to the opposite end of belt 901. Magnet 1302 and magnetic material 1304 may be switched in positioning.

FIG. 13B shows the second step of the fastening mechanism of belt 901. In the second step, the two ends of belt 901, which are at this point held together via magnetic force, are secured together by closing of buckle 1308. Next, the subject may pull on strap 1312 until the belt is tight around the subject's torso. Force multiplier 1314 aids in this tightening action. As tightening occurs, magnet 1302 slides together with magnetic material 1304 along tracks 1306 (not shown). Subject must verify that at least 5 centimeters of overlap between belt ends is present to ensure that there are no leaks in the area where belt ends meet. If overlap is less that 5 cm, subject is advised to use a larger size belt 901.

In some embodiments, the device as described herein is used to reduce the radiation dose received in an active (i.e red) bone marrow. In another embodiment, the device as described herein may be used to reduce the dose received in an active bone marrow by at least 10%. In another embodiment, the device as described herein may be used to reduce the dose received in an active bone marrow by at least 20%. In another embodiment, the device as described herein may be used to reduce the dose received in an active bone marrow by at least 30%. In another embodiment, the device as described herein may be used to reduce the dose received in an active bone marrow by at least 40%. In another embodiment, the device as described herein may be used to reduce dose received in an active bone marrow by at least 50%. In another embodiment, the device as described herein may be used to reduce the dose received in an active bone marrow by at least 60%. In another embodiment, the device as described herein may be used to reduce the dose received in an active bone marrow by at least 70%. In another embodiment, the device as described herein may be used to reduce the dose received in an active bone marrow by at least 80%. In another embodiment, the device as described herein may be used to reduce the dose received in an active bone marrow by at least 90%.

In some embodiments, a cell contained within a bone marrow may be a stem cell. In another embodiment, a cell contained within a bone marrow may be a multipotential hematopoietic stem cell (hemocytoblast). In another embodiment, a cell contained within a bone marrow may be a common myeloid progenitor (CMP) cell. In another embodiment, a cell contained within a bone marrow may be a common lymphoid progenitor (CLP) cell. In another embodiment, a cell contained within a bone marrow may be a committed progenitor cell. In another embodiment, a cell contained within a bone marrow may be a thrombocyte. In another embodiment, a cell contained within a bone marrow may be a megakaryoblast. In another embodiment, a cell contained within a bone marrow may be a promegakaryocyte. In another embodiment, a cell contained within a bone marrow may be a megakaryocyte. In another embodiment, a cell contained within a bone marrow may be a proerythroblast. In another embodiment, a cell contained within a bone marrow may be a basophilic erythroblast. In another embodiment, a cell contained within a bone marrow may be a polychromatic erythroblast. In another embodiment, a cell contained within a bone marrow may be an orthochromatic erythroblast. In another embodiment, a cell contained within a bone marrow may be a polychromatic erythrocyte.

In some embodiments, a cell contained within a bone marrow may be a mast cell. In another embodiment, a cell contained within a bone marrow may be a basophil. In another embodiment, a cell contained within a bone marrow may be a myeloblast. In another embodiment, a cell contained within a bone marrow may be a basophilic promyelocyte. In another embodiment, a cell contained within a bone marrow may be a basophilic myelocyte. In another embodiment, a cell contained within a bone marrow may be a basophilic metamyelocyte. In another embodiment, a cell contained within a bone marrow may be a neutrophil. In another embodiment, a cell contained within a bone marrow may be an eosinophil. In another embodiment, a cell contained within a bone marrow may be an eosinophilic promyelocyte. In another embodiment, a cell contained within a bone marrow may be an eosinophilic myelocyte. In another embodiment, a cell contained within a bone marrow may be an eosinophilic metamyelocyte. In another embodiment, a cell contained within a bone marrow may be a monocyte. In another embodiment, a cell contained within a bone marrow may be a promonocyte. In another embodiment, a cell contained within a bone marrow may be a prolymphocyte. In another embodiment, a cell contained within a bone marrow may be a lymphoblast. In another embodiment, a cell contained within a bone marrow may be a B cell. In another embodiment, a cell contained within a bone marrow may be a T cell. In another embodiment, a cell contained within a bone marrow is a Natural Killer cell.

In some embodiments, a cell contained within a bone marrow may be derived from one of the following lineages: Thrombopoiesis, Erythropoiesis, Granulopoiesis, Monocytopoiesis, or Lymphopoiesis. In another embodiment, a cell contained within a bone marrow may be radiosensitive.

In some embodiments, a cell protected by the device may have an enhanced survival rate under radioactive conditions. In another embodiment, a cell protected by the device and having an enhanced survival rate under radioactive condition may be a progenitor cell. In another embodiment, a cell protected by the device and having an enhanced survival rate under radioactive conditions may be a stem cell. In another embodiment, protecting a cell under radioactive conditions may comprise minimizing mutations caused by radiation.

In some embodiments, provided herein is a method of protecting a cell contained within a bone marrow of a subject against radiation, comprising the step of placing a radiation protection device on a body organ of a subject, wherein the body organ comprises an active or red bone marrow, wherein the device comprises at least a single layer of a radiation shielding material, thereby protecting a cell contained within a bone marrow of a subject against radiation.

In some embodiments, provided herein is a method of protecting a cell contained within a bone marrow of a subject against radiation, comprising the step of placing a radiation protection device on a body organ of a subject, wherein the body organ comprises an active or red bone marrow, wherein the device comprises at least a single layer of a radiation shielding material and a fallout dispersal mechanism, thereby protecting a cell contained within a bone marrow of a subject against radiation.

In another embodiment, provided herein is a method of protecting a cell contained within a bone marrow of a subject against radiation, comprising the step of placing a radiation protection device on a body organ of a subject, wherein the body organ comprises an active or red bone marrow, wherein the device comprises a fallout dispersal mechanism, thereby protecting a cell contained within a bone marrow of a subject against radiation.

In another embodiment, provided herein is a method of enhancing the survival rate of a subject exposed to radiation, comprising the step of placing a radiation protection device on a body organ in a subject, wherein the body organ comprises an active or red bone marrow, wherein the device comprises at least a single layer of a shielding material, thereby enhancing the survival rate of a subject exposed to radiation.

In another embodiment, provided herein is a method of enhancing the survival rate of a subject exposed to radiation, comprising the step of placing a radiation protection device on a body organ in a subject, wherein the body organ comprises an active or red bone marrow, wherein the device comprises at least a single layer of a shielding material and a fallout dispersal mechanism, thereby enhancing the survival rate of a subject exposed to radiation.

In another embodiment, provided herein is a method of enhancing the survival rate of a subject exposed to radiation, comprising the step of placing a radiation protection device on a body organ in a subject, wherein the body organ comprises an active or red bone marrow, wherein the device comprises a fallout dispersal mechanism for clearing radioactive particles from the vicinity of said body organ, thereby enhancing the survival rate of a subject exposed to radiation.

In another embodiment, a method as described herein further provides the step of administering to a subject a compound that induces the proliferation of a cell contained within a bone marrow. In another embodiment, a method as described herein further provides the step of administering to a subject a compound that maintains the stemness of hematopoietic stem cells contained within a bone marrow. In another embodiment, a method as described herein further provides the step of administering to a subject a compound that induces the maturation of a hematopoietic stem to a specific progenitor cell. In another embodiment, a method as described herein further provides the step of administering to a subject a compound that maintains a certain lineage within the bone marrow. In another embodiment, a method as described herein further provides the step of administering to a subject a stem cell factor, Flt3-ligand, thrombopoietin/megakaryocyte growth and development factor (MGDF), interleukin 3, SDF1, G-CSF, GM-CSF, Interleukin 1, Interleukin 11, glycosylated erythropoietin, keratinocyte growth factor (KGF), Interleukin 2, Interleukin 4, Interleukin 6, Interlrukin-7, Interlrukin-8, Interlrukin-9. Interlrukin-15, TGFβ, MPL receptor agonists, Promegapoietin-1α (PMP-1α), hyaluronic acid, PTH and active PTH fragments, PTH analogues, or a PTH/PTHrP receptor agonists or any combination thereof.

In another embodiment, a method as described herein further provides the step of intraosseous administration of substances into bones shielded by the device described herein. In another embodiment, a method as described herein further provides the step of intraosseous administration of a compound into bones shielded by the device described herein that induces the proliferation of a cell contained within a shielded bone marrow. In another embodiment, a method as described herein further provides the step of intraosseous administration into bones shielded by the device described herein of a compound that maintains the stemness of hematopoietic stem cells contained within a shielded bone marrow. In another embodiment, a method as described herein further provides the step of intraosseous administration into bones shielded by the device described herein of a compound that induces the maturation of a hematopoietic stem cell to a specific progenitor cell within a shielded marrow. In another embodiment, a method as described herein further provides the step of intraosseous administration into bones shielded by the device described herein of a compound that maintains a certain lineage within the shielded bone marrow. In another embodiment, a method as described herein further provides the step of intraosseous administration into bones shielded by the device described herein of a stem cell factor, Flt3-ligand, thrombopoietin/megakaryocyte growth and development factor (MGDF), interleukin 3, SDF1, G-CSF, GM-CSF, Interleukin 1, Interleukin 11, glycosylated erythropoietin, keratinocyte growth factor (KGF), Interleukin 2, Interleukin 4, Interleukin 6, Interlrukin-7, Interlrukin-8, Interlrukin-9. Interlrukin-15, TGFβ, MPL receptor agonists, Promegapoietin-1α (PMP-1α), hyaluronic acid, PTH and active PTH fragments, PTH analogues, or PTH/PTHrP receptor agonists or any combination thereof.

In another embodiment, a method as described herein further provides the step of administering to a subject that had been exposed to radiation a compound that induces the entry of shielded HSCs and progenitor cells into the blood stream for replenishment of unshielded marrows. Such substances include but are not limited to G-CSF, SDF-1 and AMD3100.

In another embodiment, a method as described herein further provides the step of administering to a subject a compound that protects and/or restores bone marrow function. In another embodiment, a method as described herein further provides the step of administering to a subject a compound that reduces the harmful effects of radiation. In another embodiment, a method as described herein further provides the step of administering to a subject a compound that protects against the harmful effects of radiation. In another embodiment, a method as described herein further provides the step of administering to a subject a compound that protects bone marrow cells from radiation. In another embodiment, a method as described herein further provides the step of administering to a subject a compound that reduces the harmful effects of radiation on bone marrow cells. In another embodiment, a method as described herein further provides the step of administering to a subject a drug that protects healthy cells from the damage caused by radiation. In another embodiment, a method as described herein further provides the step of administering to a subject a drug that protects healthy bone marrow cells from the damage caused by radiation. In another embodiment, a method as described herein further provides the step of administering to a subject a drug that protects healthy bone marrow cells from the damage caused by radiation even while killing off cancerous cells. In another embodiment, a method as described herein further provides the step of administering to a subject a compound that inhibits apoptosis. In another embodiment, a method as described herein further provides the step of administering to a subject a compound that inhibits apoptosis of bone marrow cells. In another embodiment, a method as described herein further provides the step of administering to a subject a compound that induces differentiation. In another embodiment, a method as described herein further provides the step of administering to a subject a compound that induces nuclear factor-Kappa B. In another embodiment, a method as described herein further provides the step of administering to a subject flagellin. In another embodiment, a method as described herein further provides the step of administering to a subject vitamin C. In another embodiment, a method as described herein further provides the step of administering to a subject a "radioprotector", such as WR-2721 and WR-1065 (Walter Reed Army Institute of Research, Washington, D.C.) or CBLB502 (Cleveland BioLabs).

In another embodiment, a method as described herein further provides the step of administering to a subject a compound or a drug before exposure to radiation. In another embodiment, a method as described herein further provides the step of administering to a subject a compound or a drug after exposure to radiation. In another embodiment, a method as described herein further provides the step of administering to a subject a compound or a drug during exposure to radiation.

In another embodiment, a method as described herein further provides the step of intraosseous administration into bones shielded by the device described herein of a compound that inhibits cells contained within a shielded bone marrow from moving out of the shielded marrow. In another embodiment, a method as described herein further provides the step of intraosseous administration into bones shielded by the device described herein of a compound that induces the entrapment of cells contained within a shielded bone marrow. In another embodiment, a method as described herein further provides the step of intraosseous administration into bones shielded by the device described herein of a compound that inhibits cells contained within a shielded bone marrow from entering the blood stream. In another embodiment, a method as described herein further provides the step of intraosseous administration of a compound into bones shielded by the device described herein that inhibits chemotaxis of cells out of the shielded marrow. In another embodiment, a method as described herein further provides the step of intraosseous administration of a compound into bones shielded by the device described herein that inhibits chemotaxis of cells out of the shielded marrow and into the blood stream. In another embodiment, a method as described herein further provides the step of intraosseous administration of a compound into bones shielded by the device described herein that inhibits chemotaxis of cells out of the shielded marrow and into the blood stream where said cells are hematopoietic stem cells. In another embodiment, a method as described herein further provides the step of intraosseous administration of a compound into bones shielded by the device described herein that inhibits chemotaxis of cells out of the shielded marrow and into the blood stream where said cells are hematopoietic progenitor cells. In another embodiment, a method as described herein further provides the step of intraosseous administration into bones shielded by the device described herein of a compound that induces the immobilization of hematopoietic stem cells or/and hematopoietic progenitor cells within a shielded marrow. In another embodiment, a method as described herein further provides the step of intraosseous administration into bones shielded by the device described herein of SDF-1 (CXCL12) or an analog, fusion protein, variant, functional derivative or fragment thereof having the activity of SDF-1 and/or an agent capable of inducing expression of said chemokine SDF-1. In another embodiment, a method as described herein further provides the step of intraosseous administration into bones shielded by the device described herein of SDF-1 (CXCL12) or an analog, fusion protein, variant, functional derivative or fragment thereof having the activity of SDF-1 in soluble form, encapsulated form or matrix-bound form. In another embodiment, a method as described herein further provides the step of intraosseous administration into bones shielded by the device described herein of anti MMP-9 (anti matrix metalloproteinase-9) antibody, neutrophil elastase (NE) inhibitor, Migrastatin or its analogues including but not limited to core macroketone and core macrolactam, TGF-β, IL-8 inhibitors, anti Groβγ antibody, anti Gr1 antibody, anti LFA-1 antibody, anti Mac-1 (CD11b) antibody, cathapsin G inhibitors, anti SDF-1 blocking antibody, soluble CXCR4, soluble CCR2, MCP-1 (CCL2) and MCP-3 (CCL7) inhibitors, G-CSF inhibitors, GM-CSF inhibitors, soluble VLA-4, anti MMP-2 antibody CB2 agonists including but not limited to AM1241 or any combination thereof.

In another embodiment, a method as described herein further provides the step of administering to a subject a compound that inhibits recruitment of hematopoietic stem cells and/or hematopoietic progenitor cells from the bone marrow into the blood. In another embodiment, a method as described herein further provides the step of administering to a subject a compound that inhibits or reduces mobilization of hematopoietic stem cells and/or hematopoietic progenitor cells. In another embodiment, a method as described herein further provides the step of intravenous, intraperitoneal, intramuscular, subcutaneous or intraosseous administration of anti SDF-1 blocking antibody, soluble CXCR4, TGF-β, anti MMP-9 (anti matrix metalloproteinase-9) antibody, neutrophil elastase (NE) inhibitor, Migrastatin or analogues including but not limited to core macroketone and core macrolactamIL-8 inhibitors, anti Groβγ antibody, anti Gr1 antibody, anti LFA-1 antibody, anti Mac-1 (CD11b) antibody, cathapsin G inhibitors, G-CSF inhibitors, GM-CSF inhibitors, soluble VLA-4, anti MMP-2 antibody or any combination thereof.

In another embodiment, a method as described herein further provides the step of intraosseous administration into bones shielded by the device described herein of a compound that draws hematopoietic stem cells and/or hematopoietic progenitor cells contained within an unshielded bone marrow into the shielded marrow. In another embodiment, a method as described herein further provides the step of intraosseous administration into bones shielded by the device described herein of a chemo-attractant that induces the chemotaxis of hematopoietic stem cells and/or hematopoietic progenitor cells contained within an unshielded bone marrow towards the shielded marrow. In another embodiment, a method as described herein further provides the step of intraosseous administration of a compound into bones shielded by the device described herein that induces migration of hematopoietic stem cells and/or hematopoietic progenitor cells out of the blood stream and into the shielded marrow. In another embodiment, a method as described herein further provides the step of intraosseous administration of a compound into bones shielded by the device described herein that induces homing of blood-borne hematopoietic stem cells and/or hematopoietic progenitor cells into the shielded marrow. In another embodiment, a method as described herein further provides the step of intraosseous administration into bones shielded by the device described herein of SDF-1 (CXCL12) or an analog, fusion protein, variant, functional derivative or fragment thereof having the activity of SDF-1 and/or an agent capable of inducing expression of said chemokine SDF-1. In another embodiment, a method as described herein further provides the step of intraosseous administration into bones shielded by the device described herein of SDF-1 (CXCL12) or an analog, fusion protein, variant, functional derivative or fragment thereof having the activity of SDF-1 in soluble form, encapsulated form or matrix-bound form. In another embodiment, a method as described herein further provides the step of intraosseous administration into bones shielded by the device described herein of agonists or partial agonists of CXCR4 and/or CXCR7, CCR2 ligands including but not limited to MCP-1 (CCL2) and MCP-3 (CCL7), CB2 agonists including but not limited to AM1241 or any combination thereof. Any substance that positively affects the migration of hematopoietic stem cells and/or hematopoietic progenitor cells into the shielded marrow is contemplated according to this invention.

In another embodiment, a method as described herein further provides the steps of bone marrow extraction from the shielded marrow of a subject that had been exposed to radiation, expansion of surviving HSCs and progenitors in-vitro by use of cytokines and reintroduction of expanded cells into the subject.

In another embodiment, a method as described herein further provides the step of administering to a subject a compound that stimulates the immune system. In another embodiment, a method as described herein further provides the step of administering to a subject an immune-stimulating cytokine such as but not limited to Neupogen In another embodiment, a method as described herein further provides the step of administering to a subject Filgrastim. In another embodiment, a method as described herein further provides the step of administering to a subject a granulocyte colony-stimulating factor (G-CSF). In another embodiment, a method as described herein further provides the step of administering to a subject an interleukin 2, interleukin 4, interleukin 11.

In another embodiment, a method as described herein further provides the step of administering to a subject a detoxifying agent. In another embodiment, a method as described herein further provides the step of administering to a subject a radioactive detoxifying agent. In another embodiment, a method as described herein further provides the step of administering to a subject potassium iodide, pentetate calcium trisodium, pentetate zinc sodium, or any combination thereof.

EXAMPLES

Example 1

Method for Determining Desired Total Attenuation ($A_D$):

The Desired Total Attenuation ($A_D$) may vary according to the use for which the radiation protection device is intended. If it is intended for continued use involving lengthy exposure to radiation, $A_D$ may be relatively high. Such a configuration may be applicable to first responders who remain in disaster zones. If it is intended for short term use, $A_D$ may be relatively low. Such a configuration may be applicable to individuals evacuating from disaster zones. Whatever the intended use, $A_D$ should be such that the surviving volume of active bone marrow is sufficient to allow for hematopoietic reconstitution after exposure. Based on numerous bone marrow transplantations this volume ranges between 23 and 58 $cm^3$ of active marrow, depending on the size of the individual. From knowledge of the radiosensitivity of human hematopoietic stem cells and progenitors (for example, see J. S. Senn and E. A. McCulloch, Blood Jan. 1, 1970 vol. 35 no. 1 56-60) and the volume of active marrow that is selected for protection by the radiation protection device, one can deduce what $A_D$ is sufficient to secure a volume of active marrow needed for hematopoietic reconstitution after exposure. The following formula may be used for this purpose:

$$A_D \geq \frac{D_U}{D_V}$$

$A_D$=Desired Total Attenuation
$D_U$=Unprotected Radiation Dose
$D_V$=Dose at which the percent viability of BM cells (as in chart below) is equal to percent viability of active bone marrow necessary for hematopoietic reconstitution ($P_R$).

$$P_R = \frac{V_N}{V_P} \times 100$$

$P_R$=Percent Viability of Active Bone Marrow Necessary for Reconstitution
$V_N$=Volume Necessary for Reconstitution (23 to 58 $cm^3$, size dependent)
$V_P$=Volume of Protected Active Bone Marrow For example, if the intended use is for one to remain in conditions of 1000 rad/hour for one hour and the radiation protection device protects in a substantially uniform manner 150 $cm^3$ of active bone marrow, the percent viability of active bone marrow necessary for hematopoietic reconstitution ($P_R$) is 23 to 58 $cm^3$ divided by 150 $cm^3$. Assuming an average size individual, $P_R$ equals 41/150*100=27.3%. From studying a human hematopoietic stem cell and progenitor radiosensitivity chart as appears in the literature (for example, see J. S. Senn and E. A. McCulloch, Blood Jan. 1, 1970 vol. 35 no. 1 56-60), the approximate radiation dose in which 27.3% of HSCs and progenitors remain viable is 200 rad ($D_V$). Thus, the desired total attenuation ($A_D$) in this case is 5[1000 rad ($D_U$) divided by 200 rad ($D_V$)]

Example 2

Method for Determining Tissue Attenuation ($A_T$) and Required Radiation Attenuation ($A_R$):

We employed the Visible Human Data set for this purpose. The Visible Human Project is the creation of complete, anatomically detailed, three-dimensional representations of the normal male and female human bodies. The data set includes transverse CT, MR and cryosection images of representative male and female cadavers. The male was sectioned at one millimeter intervals, the female at one-third of a millimeter intervals. This powerful tool allowed us to study the tissues surrounding select bone marrow concentrations, measure their thickness and determine their overall radio density.

In an example our goal was to create a belt like shield such as appears in FIG. 7A that will protect the iliac bones. By studying hundreds of slices of the pelvic area and complementing these studies by CT scans, we have mapped the tissue type and thickness present between the selected bone marrow centers and radiation entry points for hundreds of points around the waist area. Combining this knowledge with advanced radiation shielding formulas which include variables such as build up factors, we have arrived at the true tissue attenuation surrounding the bone marrow center selected for shielding. A similar calculation may be performed based on anatomical data from specific subjects selected for protection. Such data may be derived from CT scans. Alternatively, anatomical data from representative subjects such as the Visible Human data set may serve as a basis by which a radiation protection device is configured.

Such configurations based on representative individuals may be used as a basis for size extrapolation for adaptation to a larger population segment.

Knowledge of tissue attenuation allowed us to calculate the shield attenuation required to arrive at the desired total attenuation (tissue+shield) by the following formula:

$$A_R(x, y, z) = \frac{A_D}{A_T}$$

$A_R$=Required Radiation Attenuation at Point x,y,z; $A_D$=Total Desired Radiation Attenuation; $A_T$=Tissue Radiation Attenuation (between point x,y,z and the bone marrow concentration).

For example, if the $A_D$ is calculated to be 5 as in Example 1, and the $A_T$ is determined to be 2, then $A_R$ must be 2.5 to meet performance expectations.

Assuming that the approach in producing a radiation attenuation component is to provide one radiation attenuating material in varying thickness across the radiation attenuating component, the device thickness at point (x,y,z) is calculated by the following formula:

Thickness$(x,y,z) = \ln(b * A_R)/\mu$ where, $\mu$ is the linear attenuation coefficient of the radiation attenuating material used (in cm) and b is the buildup factor for one energy at thickness of material used.

In the case of the example above, where the required attenuation ($A_R$) equals 2.5, if lead (Pb) was the radiation attenuating material used, the energy of the source was 0.6 Mev and the buildup factor was 1.37, the thickness at point (x,y,z) would be:

Thickness=ln(1.37*2.5)/1.4152=0.87 cm

Following this methodology one may create a radiation attenuating component which takes into account the natural shielding properties of the subject tissue surrounding the active marrow site chosen for protection. In this example, the natural shielding properties of the subject's tissue was accounted for by varying the thickness across the radiation attenuating component. The same effect may be accomplished by use of a single thickness of multiple radiation attenuating materials of different attenuation coefficients. The same effect may also be achieved by employing both variable thickness and materials with variable attenuation coefficients.

Following the methods of Examples 1 and 2, the radiation attenuating component of exemplary belt-like radiation protection device 901 (FIG. 9-11) may be created. Such a radiation attenuating component may be comprised of layers which when compiled relate to the underlying tissue radiation attenuating properties such as demonstrated in FIG. 7A. Taking into account the natural radiation attenuation properties of the subject's tissue allows a significant reduction in the weight of the radiation attenuation component without compromising protection. Device 901 (FIG. 9-11) in combination with the individual's tissue is configured to provide a substantially uniform 4-fold total radiation attenuation ($A_D$) to 140 cm³ of active marrow in the posterior pelvis, assuming an average radionuclide energy of 0.6 Mev. Device 901 may be comfortably worn by an individual without limiting mobility. Comfort may be further increased by use of suspenders or a suspending vest.

Example 3

Direct Measurement of the Radiation Attenuation of a Radiation Protection Device and its Ability to Protect its Carrier from Gamma Radiation Emitted by Radioisotopes Measurements are carried out using TLD 3×3×1 mm Harshaw TLD LiF dosimeters (and Harshaw 3500 TLD reader. A sealed 0.5 milliCurie Cs-137 point source is used as the radiation source. The source emits 0.662 Mev Ba 137m gamma radiation (89%). A life size human phantom with a radiodensity similar to that of human tissue is employed. The dosimeters are placed at different points inside of the human phantom model at points corresponding with a bone marrow selected for protection. The radiation source is placed at an orthogonal distance of 40 cm from the phantom's surface at 3 different heights from a plane parallel to the phantom's center (to learn about the influence of the angle of incidence of the photon beam on the device). The phantom is irradiated once with the dosimeters behind a radiation protection device as embodied in FIG. 7A, and once again in the same conditions only in the absence of the device as control. The ratio between the two results indicates the percentage attenuation caused by the shield.

Example 4

Verification of the Ability of the Radiation Protection Device to Rescue Bone Marrow from Radiation A life size human model is employed. Human bone marrow specimens are obtained from hospitals and placed in vials. Several vials are placed inside pelvic area of human model in a manner reflecting the distribution of bone marrow in a live human. The bone marrow containing model is then subjected to radiation from several angles with or without the protection of a radiation protection device as described herein (e.g the device as described in FIG. 7A). The radiation dose is the maximal dose that may be sustained without suffering from serious gastrointestinal complications (1000-1200 rad). After irradiation, vials are collected and their bone marrow content evaluated for viability of hematopoietic stem cells by fluorocytometry. Each vial is evaluated separately to allow pinpointing of any site in the radiation protection device that may not be providing adequate protection. We conclude as to the efficacy of our prototype in protecting bone marrow by comparing stem cell viability in three different groups: 1) irradiated without protection; 2) irradiated with protection; 3) not irradiated.

Employing an alternative approach, mouse bone marrow is harvested from the hip area of 6-8 week old mice and placed in vials. In a manner similar to the described above, vials are embedded at different points in a life size human model and irradiated with or without protection. After irradiation, bone marrow is collected and placed in aliquots equivalent in quantity to what would be the protected marrow in a single mouse. Aliquots are then transplanted into lethally irradiated mice. Here too, each vial is evaluated separately to be able to pinpoint any problematic areas in the device. We conclude as to the efficacy of said device by comparing survival of mice in three different groups: 1) those receiving bone marrow that was irradiated without protection (mice are expected to die as if no transplantation occurred); 2) those receiving bone marrow that was irradiated with protection (mice are expected to survive as if they hadn't been irradiated); 3) those receiving bone marrow that was not irradiated (mice are expected to survive as if they hadn't been irradiated).

Animals:

Adult 12-week-old female C57 mice are used in the tests. Mice are obtained from the Jackson Laboratory (Bar Harbor, Me.). All mice are kept in small cages (5 animals in each cage) and fed sterile food and acid water.

Irradiation:

Mice are placed in and along the circumference of a single-chamber circular container with rotary covers and exposed to a single dose of total body irradiation from a 137Cs γ-irradiation source with a focal skin distance of 30 cm at a 0.5 Gy/minute dose rate. Mice are exposed to a lethal dose (8 Gy).

Bone Marrow Transplantation:

Bone marrow cells irradiated either in the presence of the radiation protection device or in its absence, are enumerated and infused intravenously into the tail veins of recipients about 6 h after irradiation.

Example 5

Radiation Protection Device Adaptation and Usage in a Non Human Primate Model.

Device configuration: Eight non human primates are subjected to CT scans of their pelvic area and the $A_T$ is determined as described in example 2. Based on $A_T$, the $A_R$ is determined for hundreds of coordinates of a radiation protection device intended to provide an $A_D$ of 4. Using lead as the radiation attenuation material and Cs-137 as the source off radiation, the lead thickness at the different coordinates is determined. The radiation protection device is configured in a similar way to the device in FIG. 7A.

Experimental Set-up: Primates are divided into two groups of 4 animals each, one group equipped with the radiation protection device and one without protection. Primates are subjected to radiation with a Cs-137 γ-irradiation source with an average focal skin distance of 100 cm at a 0.5 Gy/minute dose rate for 16 minutes for a total of 8 Gy (800 rad). Primates are allowed to move freely during irradiation to guarantee uniform exposure. Movement of primates is closely monitored to make sure that mobility is not hindered by device.

Following irradiation, animals are closely monitored. Monitoring includes alertness tests, weight measurements and complete blood counts. After 50 days survival is assessed.

Results: The group of primates protected by the radiation protection device exhibits significantly improved survival, blood counts and alertness. The radiation protection device does not hinder animal mobility as demonstrated in terms of distance walked per unit time.

Example 6

Direct Measurement of the Radiation Attenuation of a Radiation Protection Device and its Ability to Protect its Carrier from Gamma Radiation Emitted by Radioisotopes Surrounding the Subject.

To be able to determine the ability of the radiation protection device to protect its human carrier from a fallout source, radiation penetration into select pelvic bone marrow concentrations from multiple gamma-emitting radioisotope sources placed in a uniform pattern around an anatomically accurate human phantom is assessed. Dosages received at these concentrations in the presence vs. in the absence of the radiation protection device are determined. To come as close as possible to real life conditions, a human skeleton with embedded TLDs in bone marrow centers is employed as a phantom model. The phantom is subjected to irradiation with gamma radiation from several gamma-emitting radioisotopes from several points around the phantom. The placement of radioisotopes is configured to be such that the phantom is present throughout the duration of exposure in a substantially uniform radiation field (i.e. spherical). Dosimeter readings are compared to readings in the absence of shielding. The results altogether serve as an empirical assessment of the shielding provided by the belt, thus allowing us to determine the level of protection from a fallout-like source conferred to the underlying bone marrow. Knowing the dose received in the bone marrow allows us to calculate the quantity of surviving bone marrow and to see how it compares with the minimal quantity of bone marrow needed to reconstitute the hematopoietic system of a subject corresponding to the phantom's measurements.

Materials and Methods:

Water served as human tissue equivalent in the phantom used. Belt 901 is placed on the phantom in a manner akin to what is intended for humans. Several TLD dosimeters are placed in the scaffold at different strategic locations and the scaffold was submerged in water. Radioisotopes are placed at several predetermined locations around the phantom so that the exposure level was equivalent to +/−5% 100 mili roentgen over 10 cm by 10 cm squares. The dose delivered is determined by the dosimeters and recorded. A reference experiment is carried out with the same irradiation setup but in the absence of belt 901 to deduce dose reduction.

The invention claimed is:

1. A radiation protection device comprising:
    a radiation attenuation component comprising a radiation attenuating material configured to provide varying radiation attenuation levels at different points across the radiation attenuating component,
    wherein the radiation attenuation component configured to be placed adjacent to and externally covering a body part that includes active bone marrow so as to reduce a radiation dose absorbed by the bone marrow in that body part,
    wherein the radiation attenuation component has a body part side and the sheets of radiation attenuating material are layered in increasing at least one of thickness and density orthogonal to the body part side to an external side, and
    wherein the varying radiation attenuation levels across the radiation attenuating component are substantially inversely related to radiation attenuation levels of tissue present between a given point of the radiation attenuating component and the active bone marrow.

2. The device of claim 1, wherein the body part that includes active bone marrow includes a bone selected from the group of bones consisting of: skull, sternum, ribs, vertebrae, humerus, pelvis and femur.

3. The device of claim 1, further comprising friction minimizing material provided between the layers.

4. The device of claim 3, wherein the friction minimizing material is selected from the group of materials consisting of Polytetrafluoroethylene (PTFE, Teflon), polyamide-imide (PAI), Nylon 6-6, Nylon 4-6, graphite, graphite powder, acetal homopolymer or carbon fiber, and a lubricant.

5. The device of claim 1, wherein the layers are interconnected so as to allow relative movement between the layers when subjected to bending.

6. The device of claim 1, wherein the radiation attenuating component is supported by a support structure.

7. The device of claim 6, wherein the support structure comprises a resilient material.

8. The device of claim 6, wherein the support structure is configured to prevent buckling of the radiation attenuation component when the radiation attenuation component is subjected to bending.

9. The device of claim 1, wherein the radiation attenuating component comprises one or more materials selected from the group of materials consisting of barium compounds, barium sulfate, barium chloride, tungsten compounds, tungsten carbide, tungsten oxide, tungsten, bismuth compounds, bismuth, lead, tantalum compounds, titanium, titanium compounds, diatrizoate meglumine, acetrizoate sodium, boron, boric acid, boron oxide, boron salts, other boron compounds, beryllium, beryllium compounds, bunamiodyl sodium, diatrizoate sodium, ethiodized oil, gold, lobenzamic acid, locarmic acid, locetamic acid, Iodipamide, Iodixanol, Iodized oil, Iodoalphionic acid, o-Iodohippurate sodium, Iodophthalein sodium, Iodopyracet, loglycamic acid, Iohexol, lomeglamic acid, Iopamidol, lopanoic acid, Iopentol, Iophendylate, lophenoxic acid, water, Iopromide, lopronic acid, lopydol, lopydone, lothalamic acid, Iotrolan, Ioversol, loxaglic acid, Ioxilan, Ipodate, meglumine acetrizoate, meglumine ditrizoate methiodal sodium, metrizamide, metrizoic acid, phenobutiodil, phentetiothalein sodium, platinum, propryliodone, silver, sodium Iodomethamate, sozoiodolic acid, thorium oxide, trypanoate sodium, uranium and depleted uranium.

10. The device of claim 1, wherein the radiation attenuating component is incorporated in a wearable item selected from the groups of items consisting of a helmet, a bifurcated garment and a belt.

11. The device of claim 1, further comprising a sealable opening for intraosseous injection of a substance into an underlying bone within the body part.

12. A method for protecting bone marrow of a subject from radiation, the method comprising:
placing a radiation protection device that includes a radiation attenuation component comprising a radiation attenuating material providing varying radiation attenuation levels at different points across the radiation attenuating component, adjacent to and externally covering a body part that includes active bone marrow so as to reduce a radiation dose absorbed by the bone marrow in that body part,
forming the radiation protection device to comprise a body part side and layering the sheets of radiation attenuating material in at least one of increasing thickness and density orthogonal to the body part side, and
varying radiation attenuation levels across the radiation attenuating component by substantially inversely relating to radiation attenuation levels of tissue present between a given point of the radiation attenuating component and the active bone marrow.

13. The method of claim 12, further comprising administering a substance to the subject for enhancing hematopoietic reconstitution or inducing proliferation of hematopoietic stem cells or progenitors.

14. The method of claim 13, wherein the substance is selected from the group of substances consisting of G-CSF, PEGylated G-CSF, GM-CSF, M-CSF (CSF-1), AMD3100, Filgrastim (Neupogen), Pegfilgrastim, Stem cell factor (c-kit ligand or Steel Factor), Interleukin 11, Interleukin 3, Interleukin 7, Interleukin 6, Interleukin 12, Interleukin 1, Interleukin 2, Interleukin 4, Interleukin 8, Interleukin 9 Interleukin 15, Erythropoietin (EPO), Epoetin alfa (Epogen), Darbepoetin alfa (Aranesp), Omontys (peginesatide), SDF-1, friend of GATA-1 (FOG-1), PTH and active PTH fragments or PTH/PTHrP receptor agonists, leukemia inhibitory factor (LIF), Platelet-derived growth factor (PDGF), Angiotensin-(1-7), Leridistimor, Flt3-ligand, thrombopoietin, Keratinocyte growth factor (KGF), TGF β, MPL receptor agonists, Promegapoietin-1 α (PMP-1 α), hyaluronic acid and K-7/D-6.

15. The method of claim 12, further comprising administering a substance to the subject for inhibiting apoptosis of hematopoietic stem cells or progenitors.

16. The method of claim 15, wherein the substance is selected from the group of substances consisting of G-CSF, PEGylated G-CSF, GM-CSF, M-CSF (CSF-1), AMD3100, Filgrastim (Neupogen), Pegfilgrastim, Stem cell factor (c-kit ligand or Steel Factor), Interleukin 11, Interleukin 3, Interleukin 7, Interleukin 6, Interleukin 12, Interleukin 1, Interleukin 2, Interleukin 4, Interleukin 8, Interleukin 9 Interleukin 15, Erythropoietin (EPO), Epoetin alfa (Epogen), Darbepoetin alfa (Aranesp), Omontys (peginesatide), SDF-1, friend of GATA-1 (FOG-1), PTH and active PTH fragments or PTH/PTHrP receptor agonists, leukemia inhibitory factor (LIF), Platelet-derived growth factor (PDGF), Angiotensin-(1-7), Leridistimor, Flt3-ligand, thrombopoietin, Keratinocyte growth factor (KGF), TGF β, MPL receptor agonists, Promegapoietin-1 α (PMP-1 α), hyaluronic acid and K-7/D-6, δ Tocotrienol (DT3), Angiotensin-(1-7), Inducers of nuclear factor-Kappa B, Flagellin, vitamin C, WR-2721 and WR-1065, CBLB502.

17. The method of claim 12, further comprising administering a substance to the subject to prevent hematopoietic stem cells or progenitors within the active bone marrow from leaving the protected active bone marrow and circulating.

18. The method of claim 17, wherein the substance is selected form the group of substances consisting of SDF-1 (CXCL12) or an analog, fusion protein, variant, functional derivative or fragment thereof having the activity of SDF-1 and/or an agent capable of inducing expression of said chemokine SDF-1, PDGF, Somatostatin, c-kit, Hepatocyte growth factor (HGF), anti MMP-9 (anti matrix metalloproteinase-9) antibody, neutrophil elastase (NE) inhibitor, Migrastatin or its analogues including but not limited to core macroketone and core macrolactam, TGF-β, IL-8 inhibitors, anti Gro βγ antibody, anti Gr1 antibody, anti LFA-1 antibody, anti Mac-1 (CD11b) antibody, cathapsin G inhibitors, anti SDF-1 blocking antibody, soluble CXCR4, soluble CCR2, MCP-1 (CCL2) and MCP-3 (CCL7) inhibitors, G-CSF inhibitors, GM-CSF inhibitors, soluble VLA-4, anti MMP-2 antibody CB2 agonists including but not limited to AM1241.

19. The method of claim 12, further comprising administering a substance to the subject to attract hematopoietic stem cells or progenitors into the protected active bone marrow.

20. The method of claim 19, wherein the substance is selected from the group of substances consisting of SDF-1 (CXCL12) or an analog, fusion protein, variant, functional derivative or fragment thereof having the activity of SDF-1 and/or an agent capable of inducing expression of said chemokine SDF-1, agonists or partial agonists of CXCR4 and/or CXCR7, CCR2 ligands including but not limited to MCP-1 (CCL2) and MCP-3 (CCL7), CB2 agonists including but not limited to AM1241, PDGF, Somatostatin, c-kit, Hepatocyte growth factor (HGF).

21. The method of claim 12, further comprising administering a substance to the subject before, during or after the exposure to ionizing radiation.

22. The device of claim 1, wherein a thickness or density of the radiation attenuating material at each point x,y,z, on the radiation attenuating component is varied so as to provide a required attenuation level $A_R$ that is determined by the formula $A_R(x, y, z) = A_D/A_T$, $A_D$ is a radiation attenuation level needed to reduce the radiation dose absorbed in the active bone marrow contained within the body part that is covered by the point x,y,z, on the radiation attenuating component to a desired level, and $A_T$ is the tissue radiation attenuation level between the point x,y,z and the active bone marrow contained within the body part that is covered by the point x,y,z, on the radiation attenuating component.

23. The device of claim 1, wherein the radiation attenuating material comprises a gamma radiation attenuating component.

24. The device of claim 1, wherein the radiation attenuation component maintains the viability of at least 20% of the cells in 300 cm³ of active marrow.

25. The device of claim 1, wherein at least two of the sheets of radiation attenuating material vary in density.

26. The device of claim 1, wherein the sheets of radiation attenuating material are layered on top of each other in the orthogonal direction.

27. The method of claim 12, wherein a thickness or density of the radiation attenuating material at each point x,y,z, on the radiation attenuating component is varied so as to provide a required attenuation level $A_R$ that is determined by the formula $A_R$ (x, y, z)=$A_D/A_T$ where $A_D$ is a radiation attenuation level needed to reduce the radiation dose absorbed in the active bone marrow contained within the body part that is covered by the point x,y,z, on the radiation attenuating component to a desired level, and $A_T$ is the tissue radiation attenuation level between the point x,y,z and the active bone marrow contained within the body part that is covered by the point x,y,z, on the radiation attenuating component.

28. The method of claim 12, wherein the radiation attenuating material comprises a gamma radiation attenuating component.

29. The method of claim 12, further comprising the step of maintaining the viability of at least 20% of the cells in 300 cm³ of active marrow.

30. The method of claim 12, wherein the forming step further comprising the step of varying the density of at least two of the sheets of radiation attenuating material.

31. The method of claim 12, wherein the forming step further comprises the step of layering the sheets of radiation attenuating material on top of each other in the orthogonal direction.

32. A radiation protection belt providing protection of active bone marrow from external ionizing radiation, comprising:
   a gamma radiation attenuating component configured to be placed adjacent to and externally cover at least one of the waist and the pelvis of a user so as to reduce a radiation dose absorbed in the active bone marrow in the pelvis, comprising radiation attenuating material of at least one of varying thickness and density to provide varying radiation levels across the gamma radiation attenuating component, such that the varying radiation attenuation level at each point on the radiation attenuating component is inversely related to radiation attenuation levels of tissue present between the point of the radiation attenuating component and the active bone marrow in the pelvis.

33. The belt of claim 32, wherein the gamma radiation attenuating component comprises layers of radiation attenuating material.

34. The belt of claim 32, wherein a portion of the active bone marrow being protected is in the iliac crest of the pelvis.

35. The device of claim 1, wherein the radiation attenuating component comprises sheets of radiation attenuating material configured in layers.

36. The method of claim 12, wherein the radiation attenuating component comprises sheets of radiation attenuating material configured in layers.

* * * * *